(12) United States Patent
Nguyen et al.

(10) Patent No.: US 9,744,024 B2
(45) Date of Patent: Aug. 29, 2017

(54) AXIAL LENGTHENING THROMBUS CAPTURE SYSTEM

(71) Applicant: KP Medcure, Inc., Anaheim, CA (US)

(72) Inventors: Thanh Van Nguyen, Anaheim, CA (US); Duy Nguyen, Anaheim, CA (US); Tung Hoang Ngo, Anaheim, CA (US)

(73) Assignee: KP Medcure, Inc., Anaheim, CA (US)

( * ) Notice: Subject to any disclaimer, the term of this patent is extended or adjusted under 35 U.S.C. 154(b) by 0 days.

(21) Appl. No.: 15/428,076

(22) Filed: Feb. 8, 2017

(65) Prior Publication Data

US 2017/0143359 A1 May 25, 2017

Related U.S. Application Data

(63) Continuation-in-part of application No. 15/230,109, filed on Aug. 5, 2016, now Pat. No. 9,579,116.
(Continued)

(51) Int. Cl.
*A61B 17/221* (2006.01)
*A61M 29/00* (2006.01)
(Continued)

(52) U.S. Cl.
CPC ............ *A61F 2/013* (2013.01); *A61B 17/221* (2013.01); *A61B 17/320758* (2013.01); *A61B 2017/00867* (2013.01); *A61B 2017/00871* (2013.01); *A61B 2017/00938* (2013.01); *A61B 2017/00942* (2013.01); *A61B 2017/2212* (2013.01); *A61B 2017/2217* (2013.01); *A61B 2017/22038* (2013.01); *A61B 2017/22079* (2013.01); *A61B 2017/22081* (2013.01); *A61B 2017/22084* (2013.01); *A61B 2017/320052* (2013.01); *A61B 2017/320716* (2013.01); *A61B 2017/320775* (2013.01); *A61F 2002/011* (2013.01); *A61F 2002/016* (2013.01)

(58) Field of Classification Search
CPC .......... A61B 17/221; A61B 17/320758; A61B 2017/320064; A61B 2017/320775; A61B 2017/2212; A61B 2017/00867; A61B 2017/00893; A61B 2017/320716
See application file for complete search history.

(56) References Cited

U.S. PATENT DOCUMENTS 3,506,011 A 4/1970 Silverman
5,011,488 A 4/1991 Ginsburg
(Continued)

FOREIGN PATENT DOCUMENTS

WO WO 2008/070996 A1 6/2008
WO WO 2015079401 A2 6/2015

OTHER PUBLICATIONS

US 8,668,714, 03/2014, Cully et al. (withdrawn)
(Continued)

*Primary Examiner* — Julian W Woo
(74) *Attorney, Agent, or Firm* — Knobbe, Martens, Olson & Bear, LLP

(57) ABSTRACT

Systems and methods can remove material of interest, including blood clots, from a body region, including but not limited to the circulatory system for the treatment of pulmonary embolism (PE), deep vein thrombosis (DVT), cerebrovascular embolism, and other vascular occlusions.

24 Claims, 69 Drawing Sheets

Related U.S. Application Data

(60) Provisional application No. 62/202,074, filed on Aug. 6, 2015, provisional application No. 62/273,418, filed on Dec. 30, 2015, provisional application No. 62/345,863, filed on Jun. 6, 2016.

(51) Int. Cl.

| | | |
|---|---|---|
| *A61B 17/3207* | (2006.01) | |
| *A61F 2/01* | (2006.01) | |
| *A61B 17/22* | (2006.01) | |
| *A61B 17/00* | (2006.01) | |
| *A61B 17/32* | (2006.01) | |

(56) References Cited

U.S. PATENT DOCUMENTS

| | | | |
|---|---|---|---|
| 5,102,415 | A | 4/1992 | Guenther et al. |
| 5,135,484 | A | 8/1992 | Wright |
| 5,846,251 | A | 12/1998 | Hart |
| 5,895,398 | A | 4/1999 | Wensel et al. |
| 5,935,139 | A | 8/1999 | Bates |
| 5,947,985 | A | 9/1999 | Imran |
| 6,066,149 | A | 5/2000 | Samson et al. |
| 6,126,635 | A | 10/2000 | Simpson et al. |
| 6,165,196 | A | 12/2000 | Stack et al. |
| 6,179,859 | B1 * | 1/2001 | Bates ................ A61F 2/013 606/114 |
| 6,210,370 | B1 | 4/2001 | Chi-Sing et al. |
| 6,221,006 | B1 | 4/2001 | Dubrul et al. |
| 6,264,663 | B1 | 7/2001 | Cano |
| 6,270,477 | B1 | 8/2001 | Bagaoisan et al. |
| 6,391,044 | B1 | 5/2002 | Yadav et al. |
| 6,432,122 | B1 | 8/2002 | Gilson et al. |
| 6,569,181 | B1 | 5/2003 | Burns |
| 6,605,102 | B1 | 8/2003 | Mazzocchi et al. |
| 6,620,182 | B1 * | 9/2003 | Khosravi ................ A61F 2/01 606/194 |
| 6,635,070 | B2 | 10/2003 | Leeflang et al. |
| 6,645,224 | B2 | 11/2003 | Gilson et al. |
| 6,663,650 | B2 | 12/2003 | Sepetka et al. |
| 6,824,545 | B2 | 11/2004 | Sepetka et al. |
| 6,840,950 | B2 | 1/2005 | Stanford et al. |
| 6,945,977 | B2 | 9/2005 | Demarais et al. |
| 7,094,249 | B1 * | 8/2006 | Broome ............... A61B 17/221 606/200 |
| 7,220,271 | B2 | 5/2007 | Clubb et al. |
| 7,621,870 | B2 | 11/2009 | Berrada et al. |
| 7,662,165 | B2 | 2/2010 | Gilson et al. |
| 7,766,921 | B2 | 8/2010 | Sepetka et al. |
| 7,780,696 | B2 | 8/2010 | Daniel et al. |
| 7,785,342 | B2 | 8/2010 | Gilson et al. |
| 7,901,426 | B2 | 3/2011 | Gilson et al. |
| 8,070,769 | B2 | 12/2011 | Broome |
| 8,092,486 | B2 | 1/2012 | Berrada et al. |
| 8,236,024 | B2 | 8/2012 | Stanford et al. |
| 8,252,017 | B2 | 8/2012 | Paul, Jr. et al. |
| 8,255,193 | B2 | 8/2012 | Humphrey et al. |
| 8,298,252 | B2 | 10/2012 | Krolik et al. |
| 8,313,503 | B2 | 11/2012 | Cully et al. |
| 8,337,520 | B2 | 12/2012 | Cully et al. |
| 8,388,644 | B2 | 3/2013 | Parker |
| 8,460,335 | B2 | 6/2013 | Carpenter |
| 8,475,487 | B2 | 7/2013 | Bonnette et al. |
| 8,491,623 | B2 | 7/2013 | Vogel et al. |
| 8,545,526 | B2 | 10/2013 | Martin et al. |
| 8,613,717 | B2 | 12/2013 | Aklog et al. |
| 8,657,849 | B2 | 2/2014 | Parker |
| 8,734,374 | B2 | 5/2014 | Aklog et al. |
| 8,771,289 | B2 | 7/2014 | Mohiuddin et al. |
| 8,777,976 | B2 | 7/2014 | Brady et al. |
| 8,795,305 | B2 | 8/2014 | Martin et al. |
| 8,795,322 | B2 | 8/2014 | Cully et al. |
| 8,801,748 | B2 | 8/2014 | Martin |
| 8,926,642 | B2 | 1/2015 | Nelson |
| 8,932,319 | B2 | 1/2015 | Martin et al. |
| 8,948,848 | B2 | 2/2015 | Merhi |
| 8,956,384 | B2 | 2/2015 | Berrada et al. |
| 8,968,330 | B2 * | 3/2015 | Rosenbluth .... A61B 17/320725 606/127 |
| 8,998,944 | B2 | 4/2015 | Thornton |
| 9,254,371 | B2 | 2/2016 | Martin et al. |
| 9,283,066 | B2 * | 3/2016 | Hopkins ................ A61F 2/01 |
| 9,301,769 | B2 | 4/2016 | Brady |
| 9,308,007 | B2 | 4/2016 | Cully et al. |
| 9,526,864 | B2 * | 12/2016 | Quick ................ A61B 17/221 |
| 9,579,116 | B1 | 2/2017 | Nguyen et al. |
| 2002/0169474 | A1 | 11/2002 | Kusleika et al. |
| 2003/0176884 | A1 | 9/2003 | Berrada et al. |
| 2004/0039411 | A1 | 2/2004 | Gilson et al. |
| 2004/0073198 | A1 | 4/2004 | Gilson et al. |
| 2004/0098025 | A1 | 5/2004 | Sepetka et al. |
| 2004/0098033 | A1 | 5/2004 | Leeflang et al. |
| 2006/0025804 | A1 | 2/2006 | Krolik et al. |
| 2006/0155305 | A1 | 7/2006 | Freudenthal et al. |
| 2007/0010702 | A1 | 1/2007 | Wang et al. |
| 2007/0088382 | A1 | 4/2007 | Bei et al. |
| 2007/0282303 | A1 | 12/2007 | Nash et al. |
| 2008/0167678 | A1 * | 7/2008 | Morsi ............ A61B 17/320725 606/200 |
| 2009/0292307 | A1 | 11/2009 | Razack |
| 2010/0211095 | A1 | 8/2010 | Carpenter |
| 2010/0268264 | A1 | 10/2010 | Bonnette et al. |
| 2011/0166586 | A1 | 7/2011 | Sepetka et al. |
| 2012/0197285 | A1 | 8/2012 | Martin et al. |
| 2012/0310251 | A1 | 12/2012 | Sepetka et al. |
| 2012/0330346 | A1 | 12/2012 | Frimerman |
| 2012/0330350 | A1 | 12/2012 | Jones et al. |
| 2013/0102996 | A1 | 4/2013 | Strauss |
| 2013/0178891 | A1 | 7/2013 | Russell et al. |
| 2013/0184738 | A1 | 7/2013 | Laroya et al. |
| 2013/0184741 | A1 | 7/2013 | Laroya et al. |
| 2013/0197567 | A1 | 8/2013 | Brady et al. |
| 2013/0238009 | A9 | 9/2013 | Hopkins et al. |
| 2013/0267993 | A1 | 10/2013 | Carpenter |
| 2013/0338703 | A1 | 12/2013 | Hansen et al. |
| 2014/0005712 | A1 | 1/2014 | Martin |
| 2014/0005717 | A1 | 1/2014 | Martin et al. |
| 2014/0046358 | A1 | 2/2014 | Cully et al. |
| 2014/0052103 | A1 | 2/2014 | Cully et al. |
| 2014/0128894 | A1 | 5/2014 | Sepetka et al. |
| 2014/0249568 | A1 | 9/2014 | Adams et al. |
| 2014/0276403 | A1 | 9/2014 | Follmer et al. |
| 2014/0276922 | A1 | 9/2014 | McLain et al. |
| 2014/0277013 | A1 | 9/2014 | Sepetka et al. |
| 2014/0350593 | A1 | 11/2014 | Laroya et al. |
| 2014/0371781 | A1 | 12/2014 | Morgan |
| 2015/0005781 | A1 | 1/2015 | Lund-Clausen et al. |
| 2015/0018929 | A1 | 1/2015 | Martin et al. |
| 2015/0088190 | A1 | 3/2015 | Jensen |
| 2015/0196380 | A1 | 7/2015 | Berrada et al. |
| 2015/0265299 | A1 | 9/2015 | Cooper et al. |
| 2015/0306311 | A1 | 10/2015 | Pinchuk et al. |
| 2016/0022290 | A1 | 1/2016 | Johnson et al. |
| 2016/0022291 | A1 | 1/2016 | Johnson et al. |
| 2016/0038271 | A1 | 2/2016 | Johnsen et al. |

OTHER PUBLICATIONS

U.S. Appl. No. 15/376,448, filed Dec. 12, 2016, Nguyen et al.
International Search Report and Written Opinion in PCT Application No. PCT/US2016/045862 mailed Dec. 1, 2016 in 8 pages.
Notice of Allowance in U.S. Appl. No. 15/376,448 dated Mar. 8, 2017 in 9 pages.

* cited by examiner

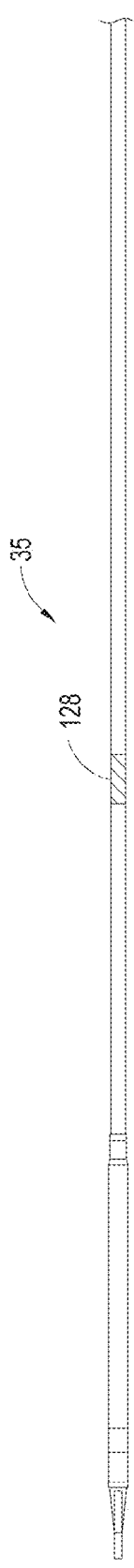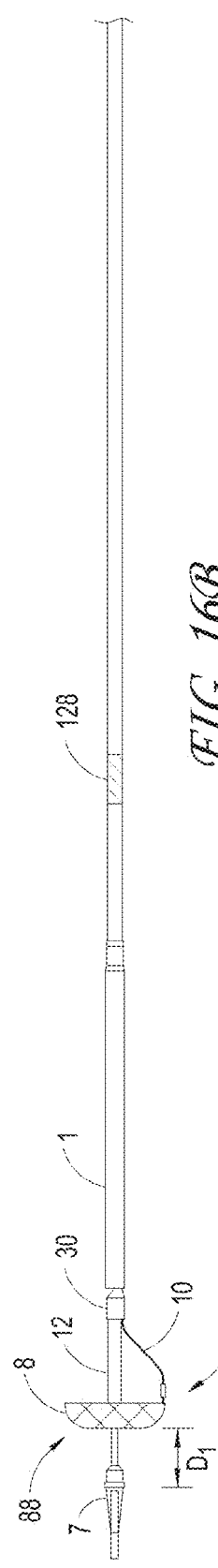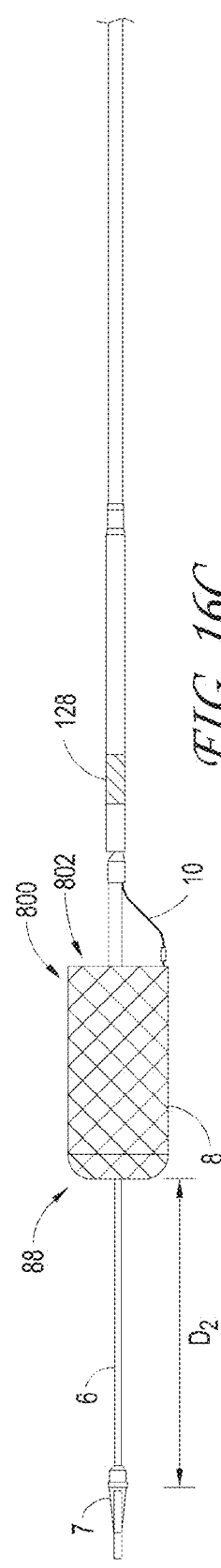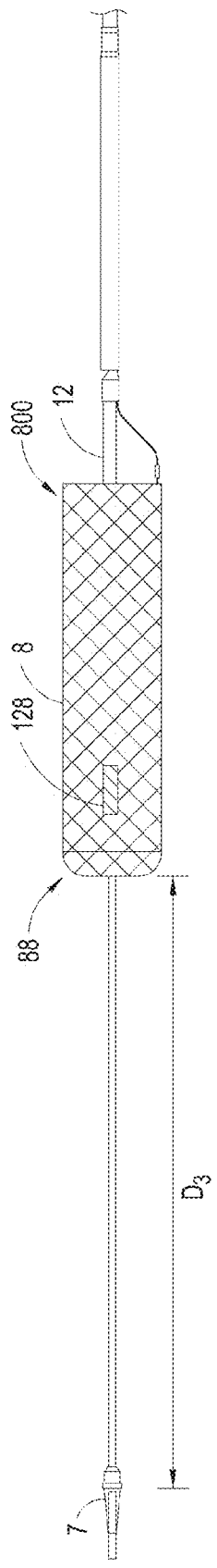

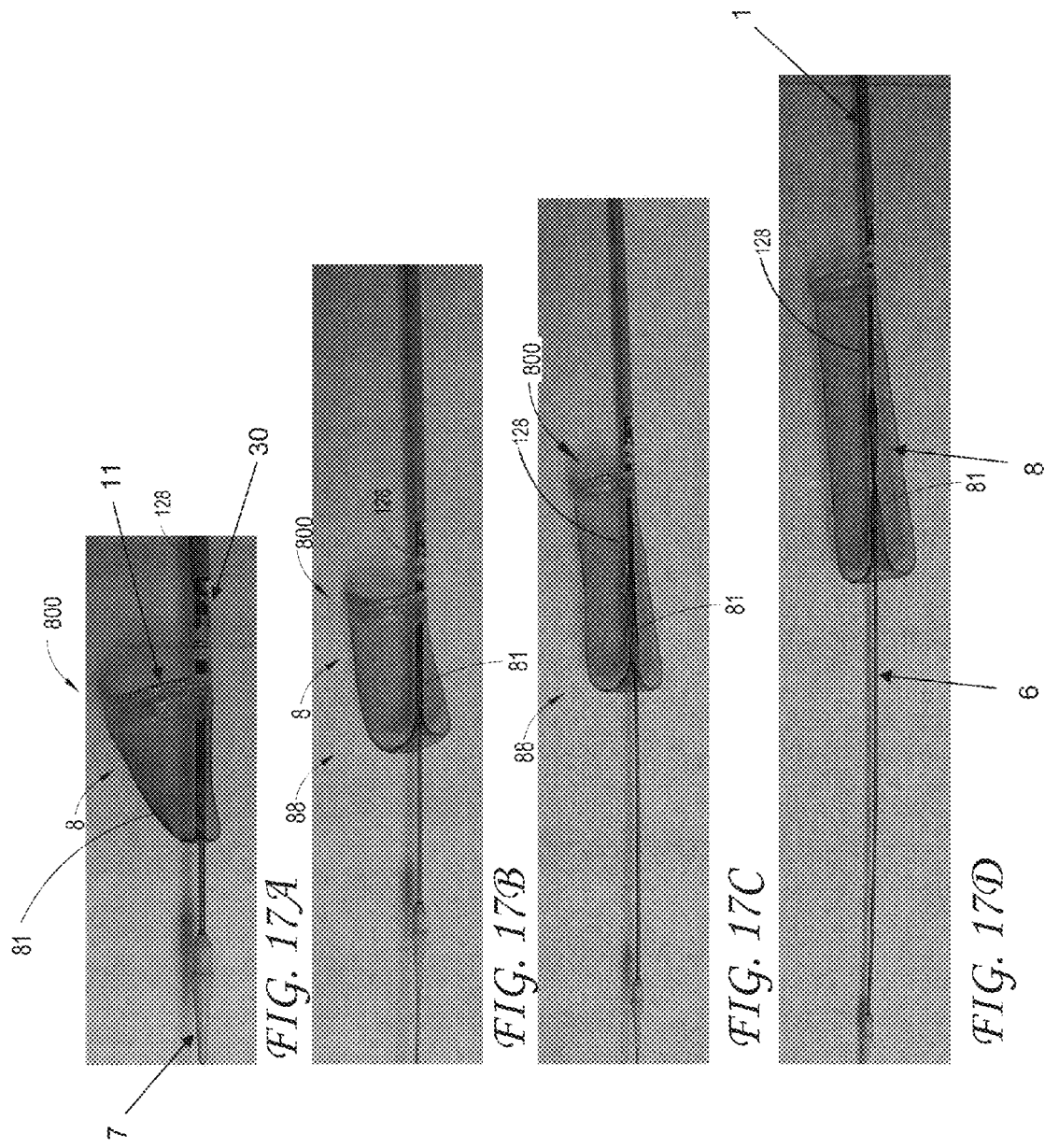

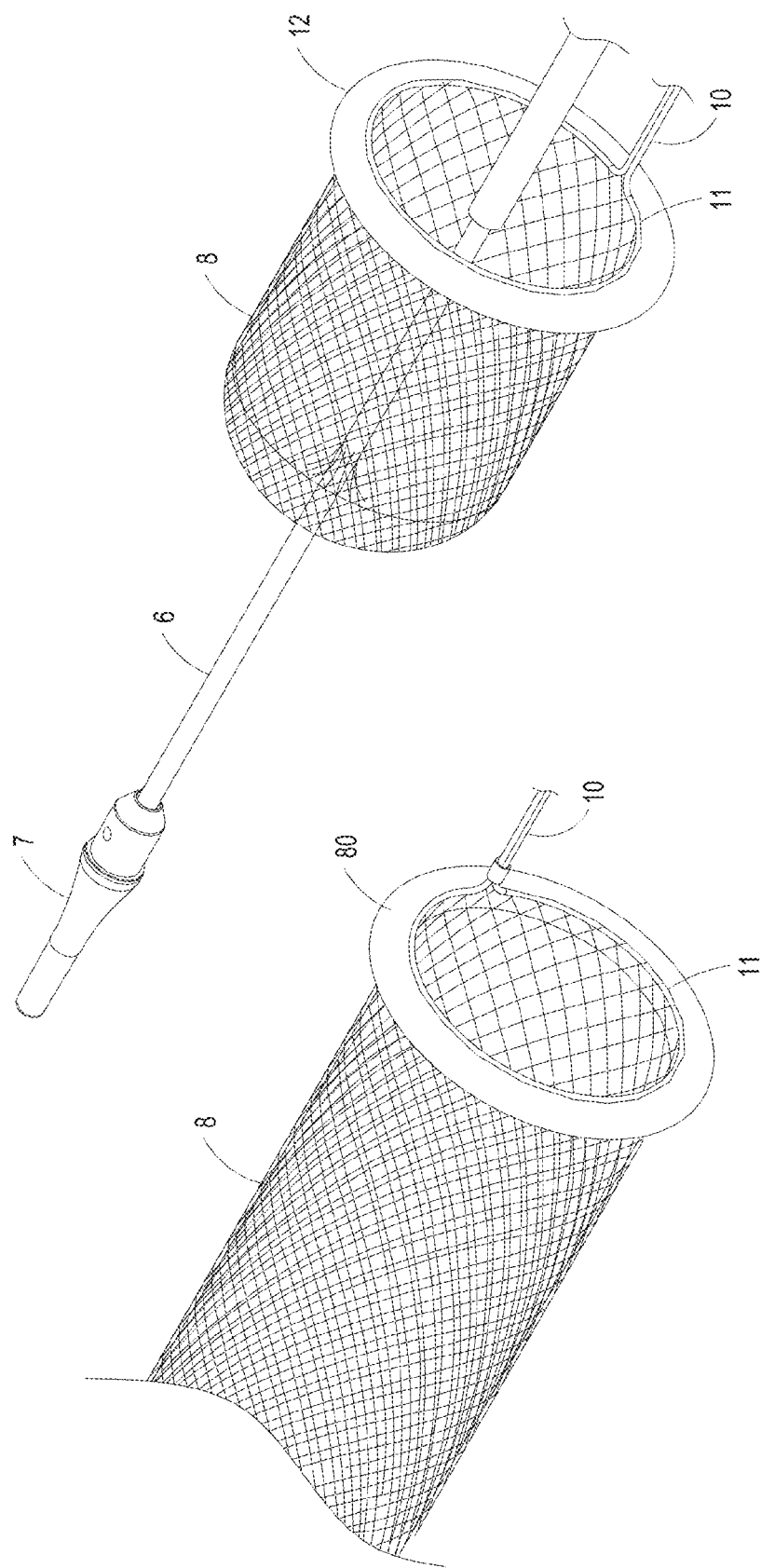

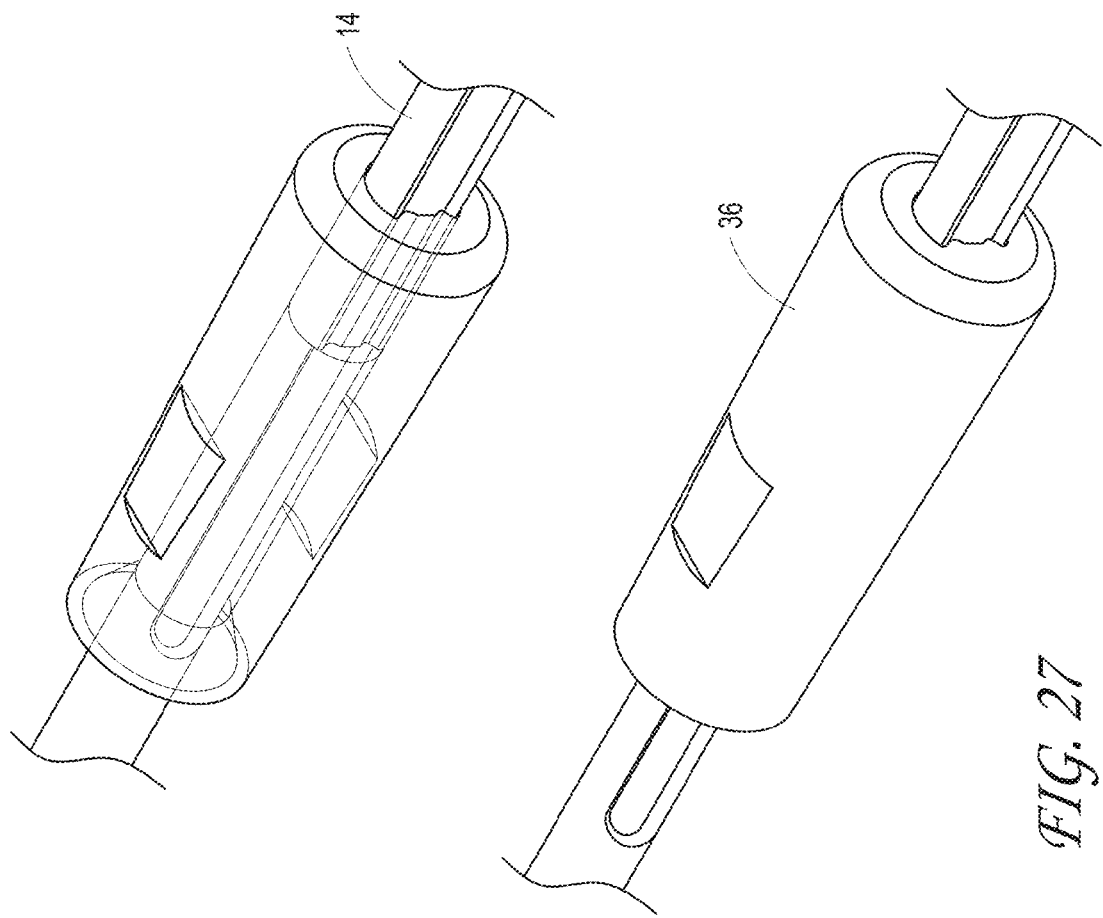
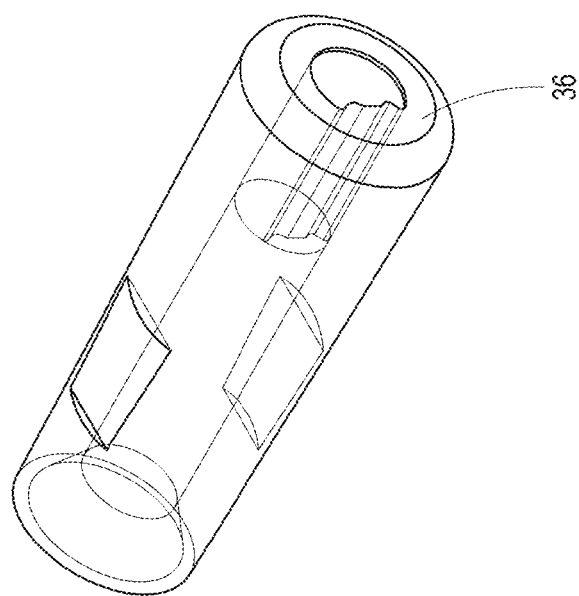
FIG. 27

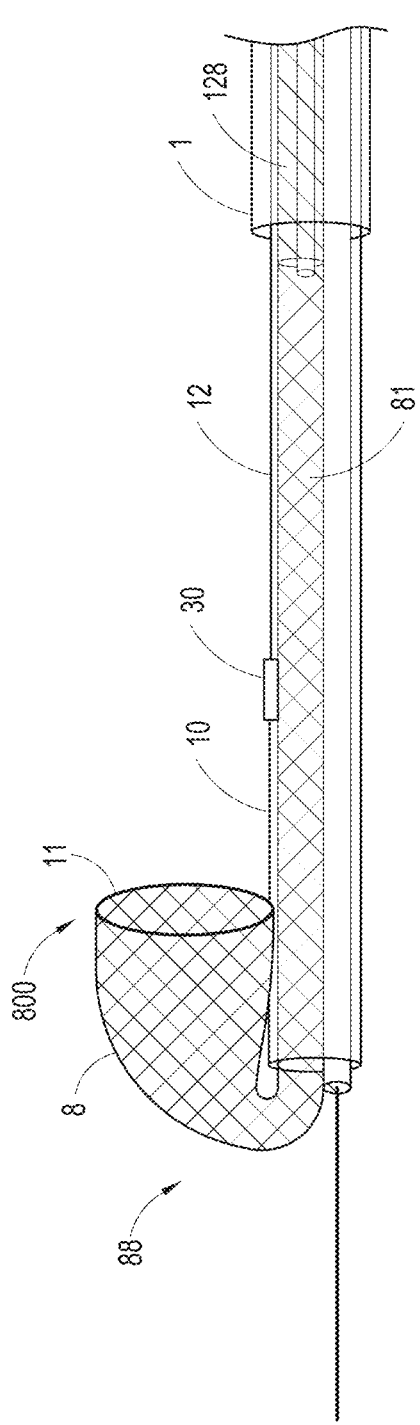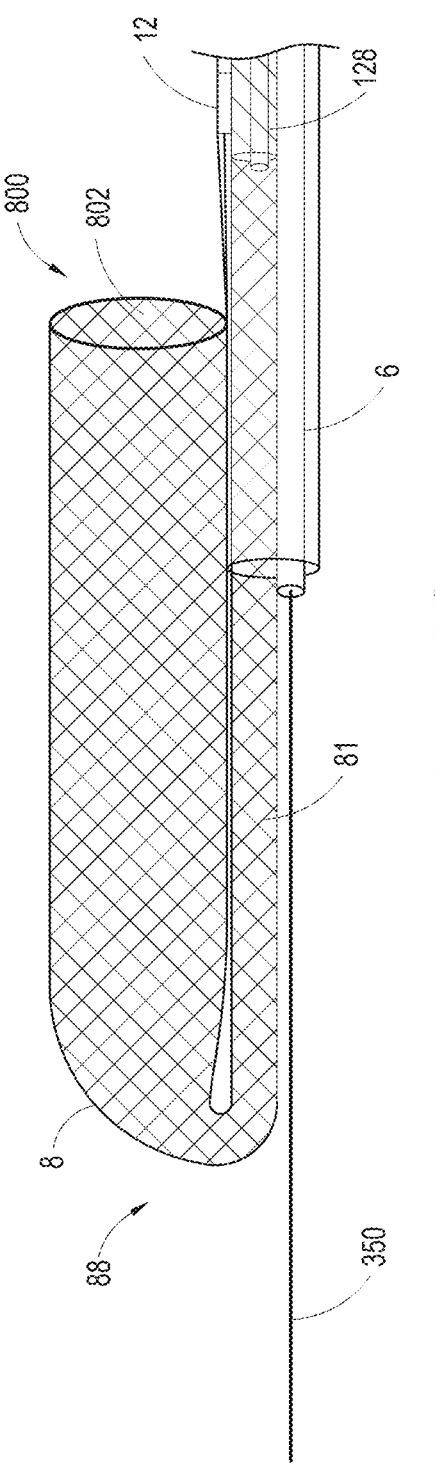

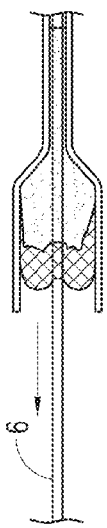
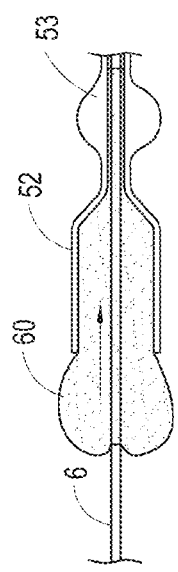
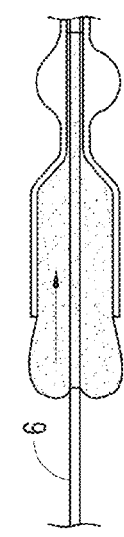

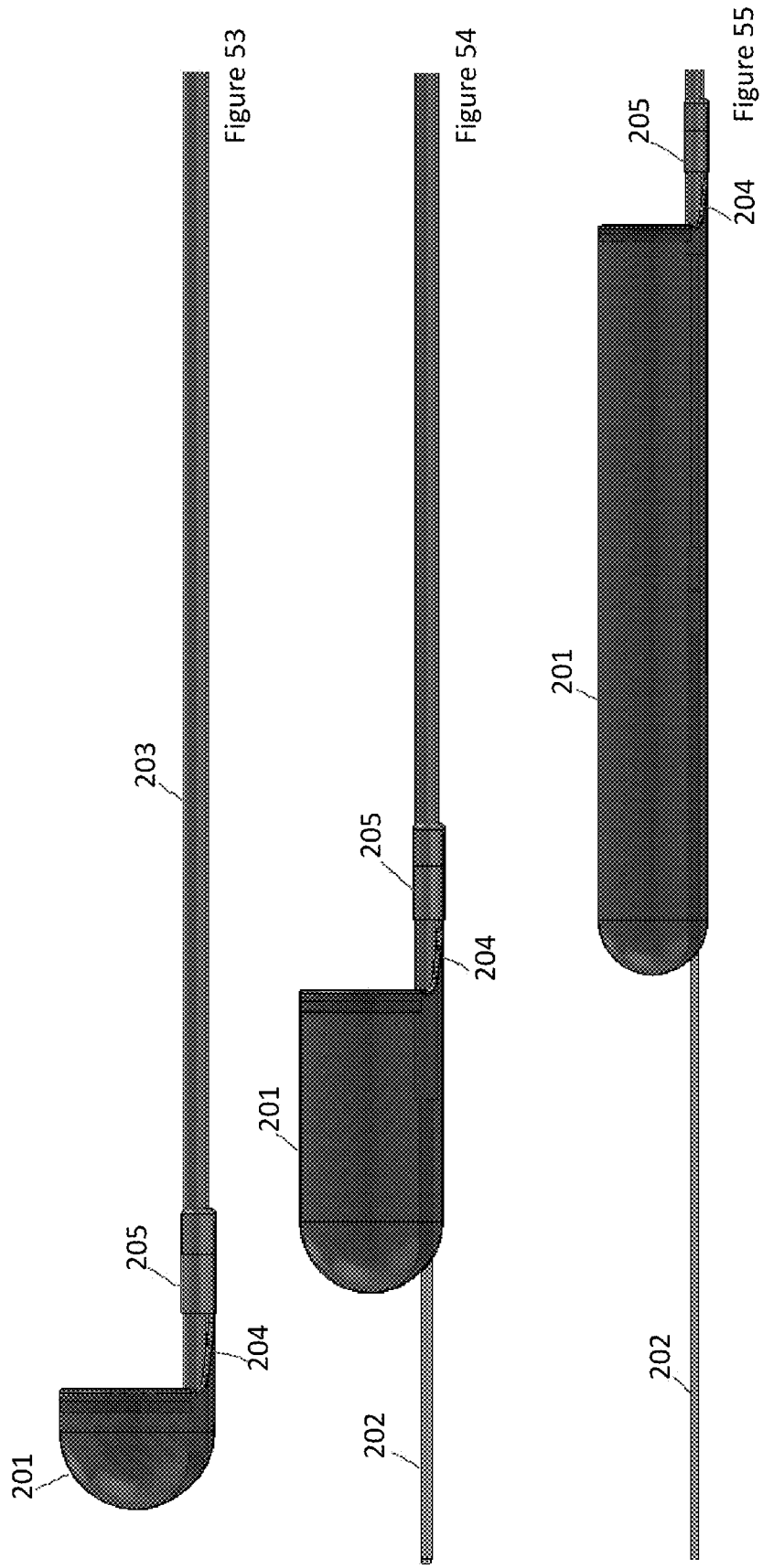

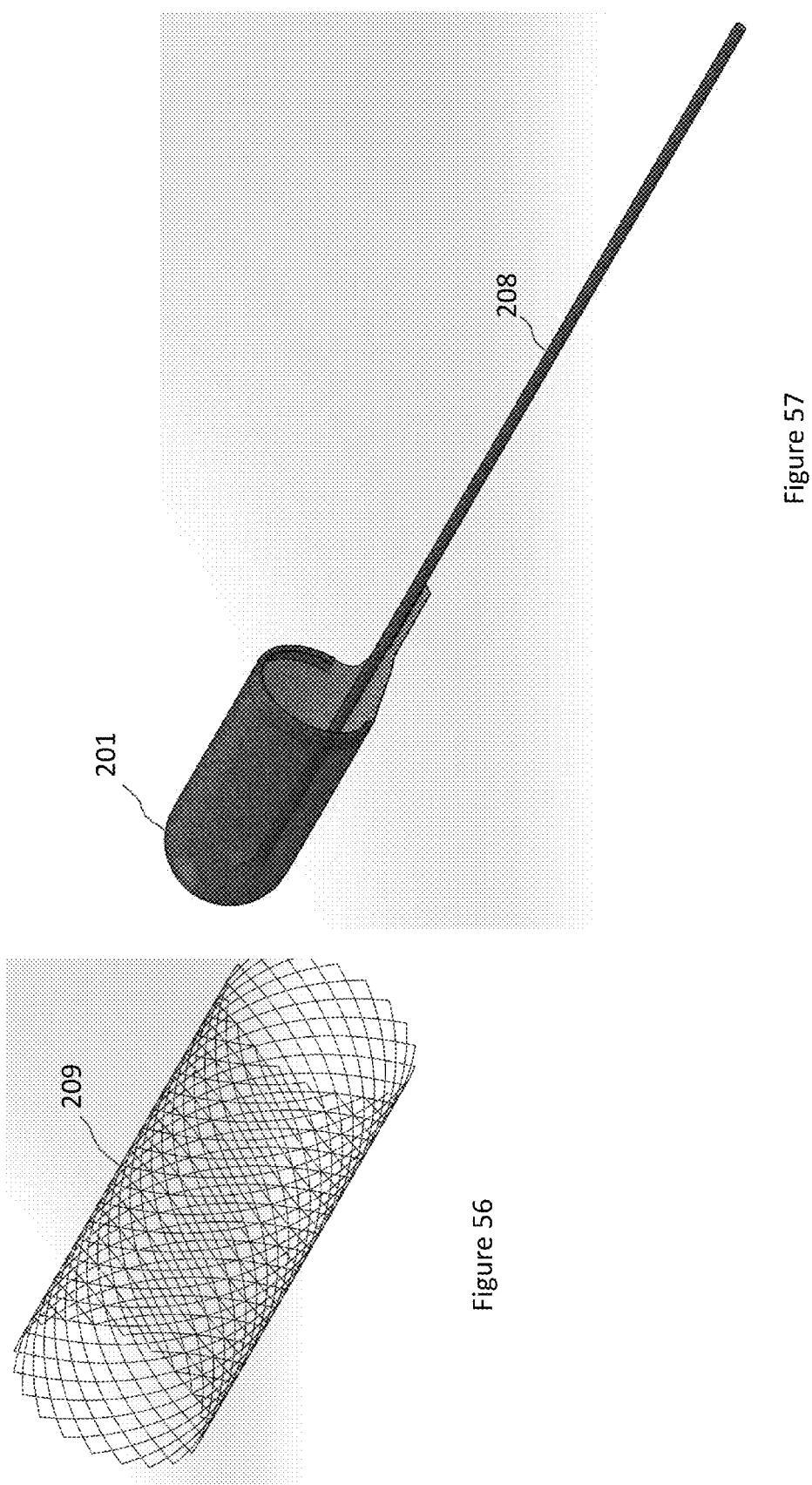

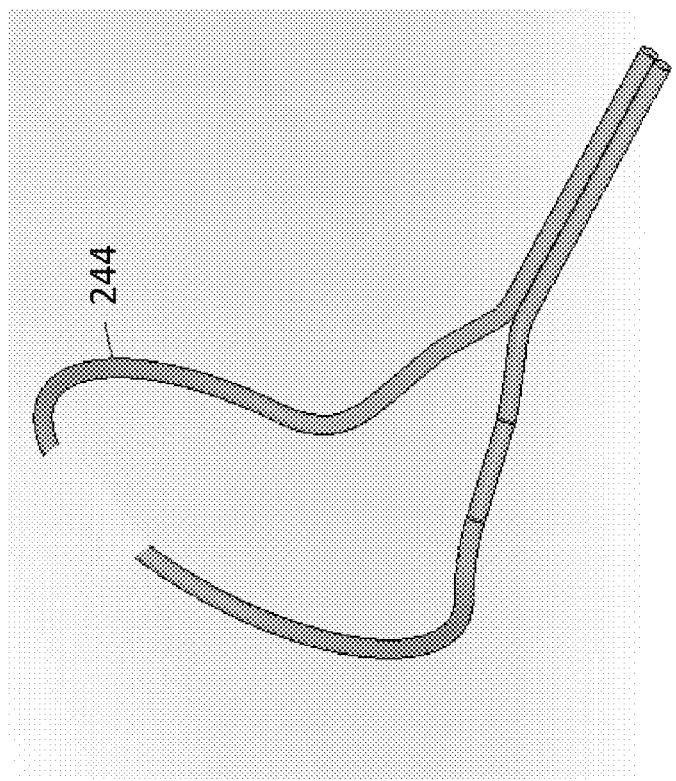
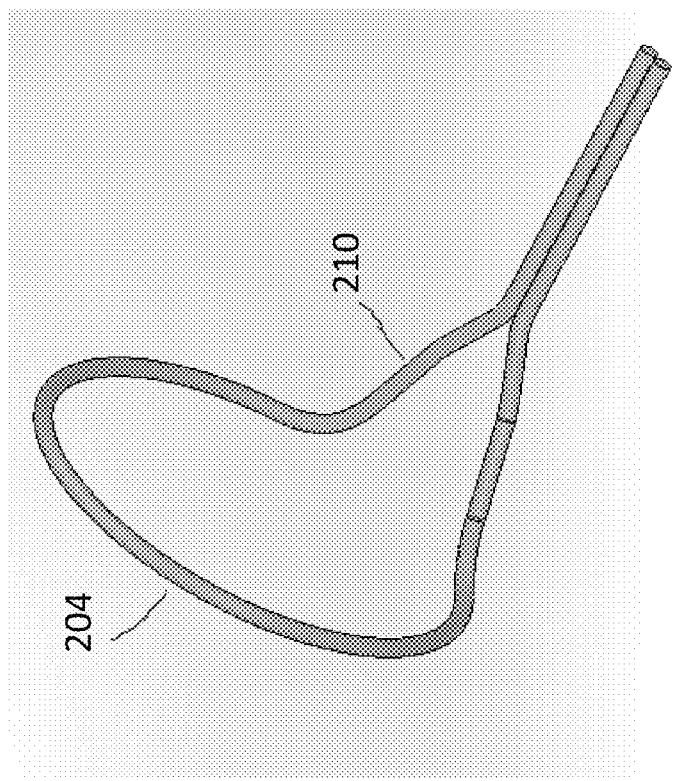

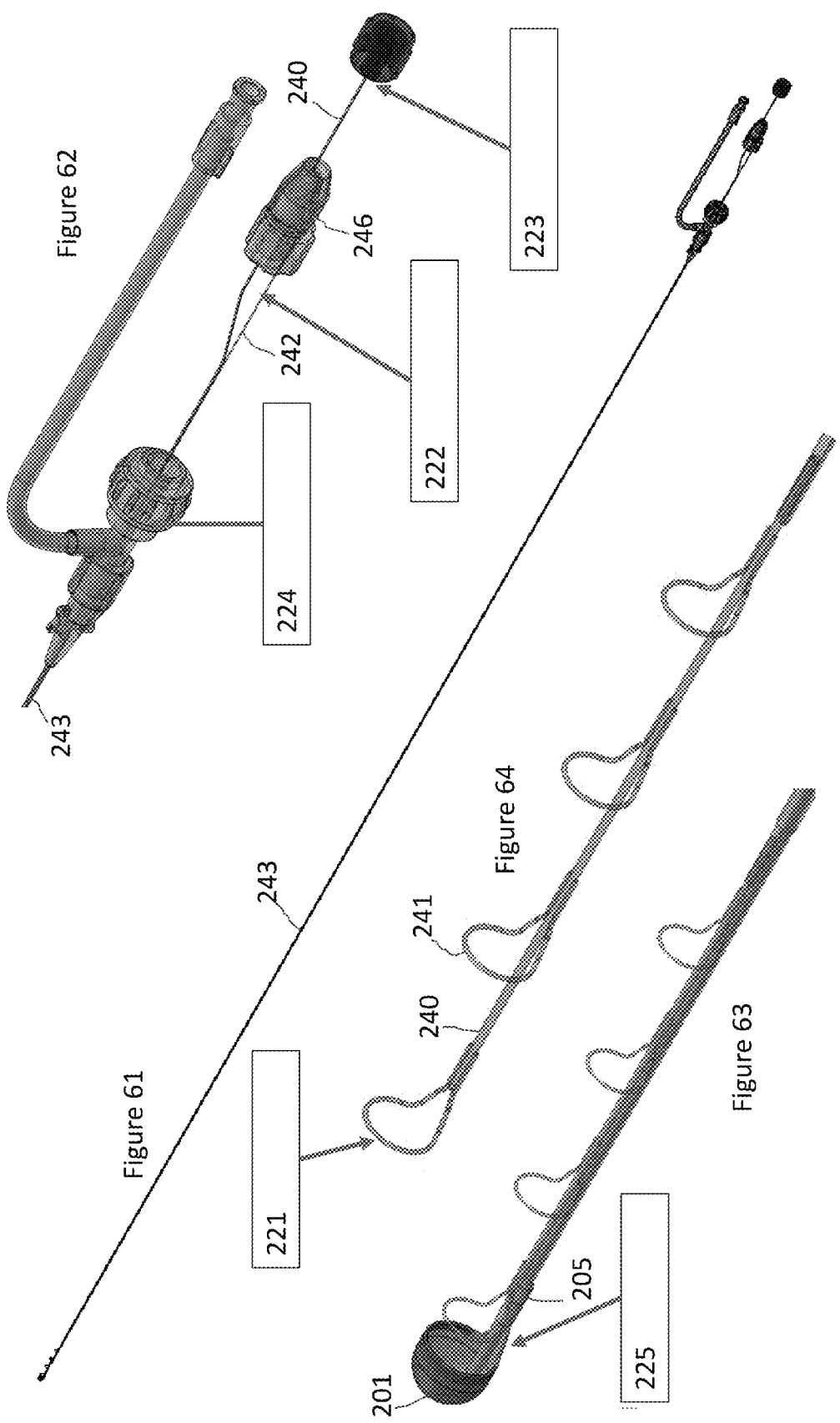

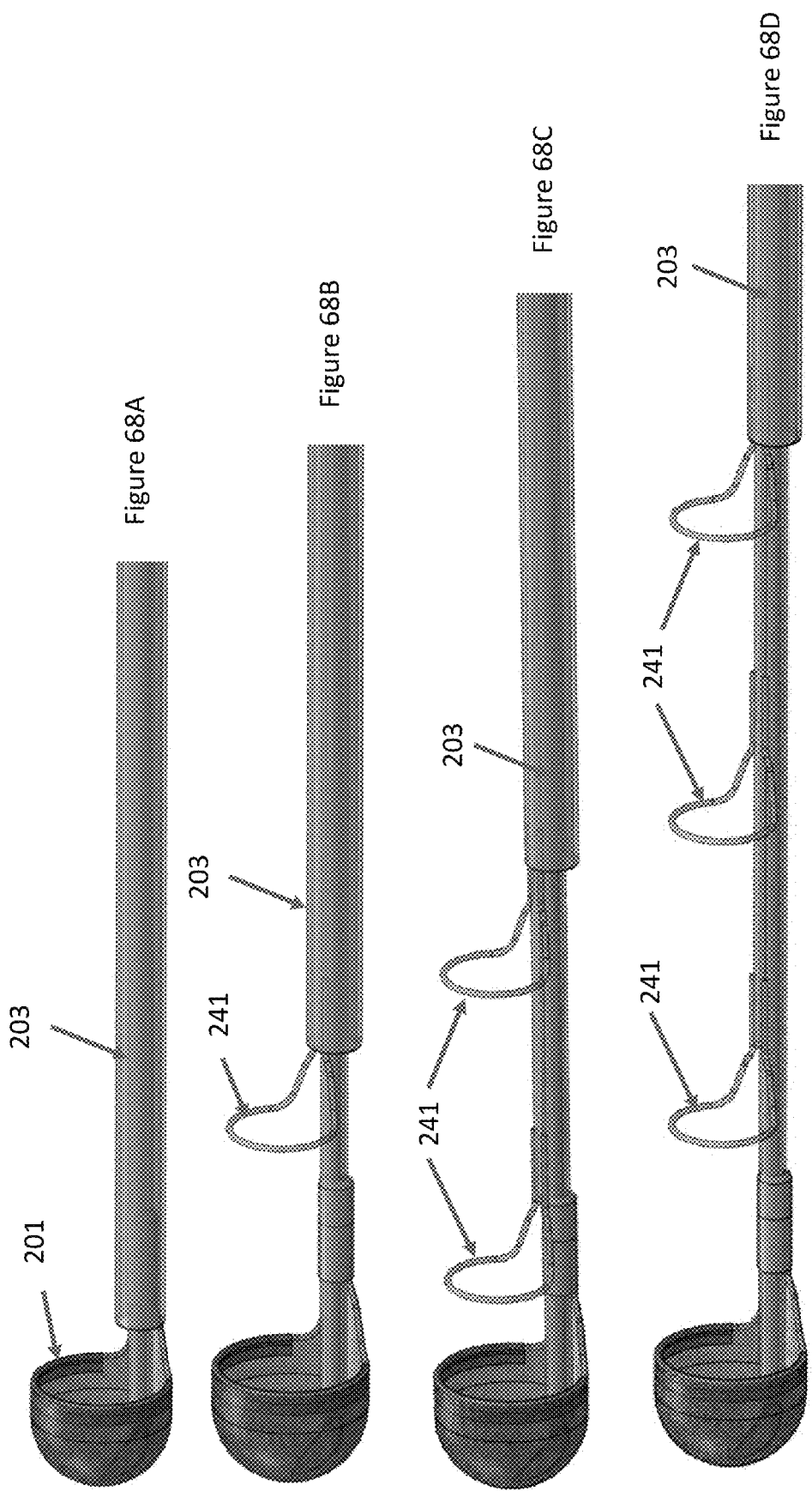

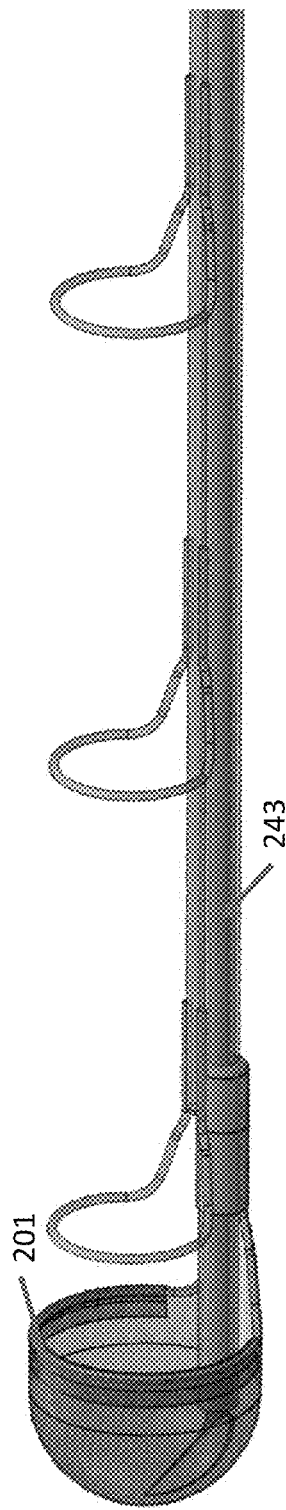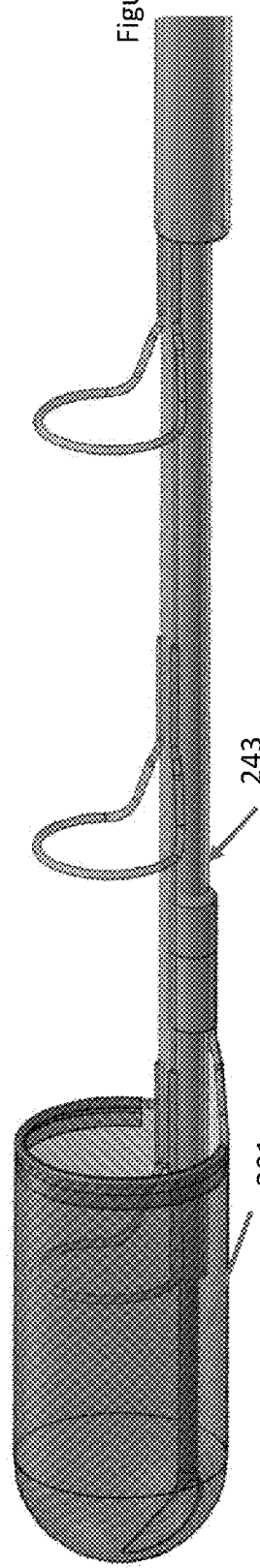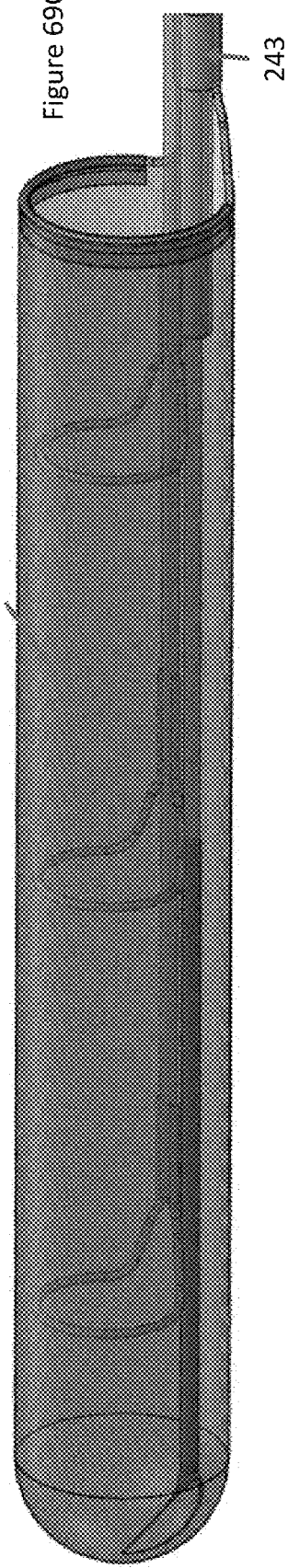

AXIAL LENGTHENING THROMBUS CAPTURE SYSTEM

PRIORITY CLAIM

This application claims the benefit under 35 U.S.C. §120 as a continuation-in-part application of U.S. patent application Ser. No. 15/230,109 filed on Aug. 5, 2016, which claims the benefit under 35 U.S.C. §119(e) as a nonprovisional application of each of U.S. Provisional App. Nos. 62/202,074 filed on Aug. 6, 2015, 62/273,418 filed on Dec. 30, 2015, and 62/345,863 filed on Jun. 6, 2016. Each of the aforementioned priority applications is hereby incorporated by reference in their entireties.

BACKGROUND

Field of the Invention

The invention relates to, in some aspects, systems and methods to remove materials of interest, including blood clots, from a body region, including but not limited to the circulatory system for the treatment of pulmonary embolism (PE), deep vein thrombosis (DVT), cerebrovascular embolism, and other vascular occlusions.

Description of the Related Art

It is understood that undesirable materials such as blood clots (which could be referred to as thrombi, thromboemboli, or emboli herein) in the blood vessels may partially or completely occlude blood vessels in areas of the coronary, cerebrovascular, pulmonary, peripheral venous, and peripheral arterial circulation resulting in myocardial infarction, stroke, pulmonary embolism, deep vein thrombosis, and infarction of an extremity respectively.

Various therapies and devices are known to either dissolve, debulk and/or aspirate the thromboemboli. For instance, anticoagulant agents such as heparin and warfarin help stabilize blood clots and prevent further forming of clots while thrombolytic agents such as urokinase, streptokinase, and tPA assist in dissolving blood clots. These agents can be delivered via systemic infusion or catheter-based infusion to the intended location. While thrombolytic agents can be effective in dissolving blood clots, they require a long time duration in order for the agents to dissolve the blood clots; thus patients may need to remain in the hospital intensive care unit (ICU) during thrombolytic infusion. Relatively long lengths of stay can increase healthcare costs significantly. A major limitation for these thrombolytic agents is that they can potentially cause intracranial, gastrointestinal, retroperitoneal, and pericardial bleeding, among other sites, which can be often life-threatening and cause significant morbidity and mortality risks.

Mechanical debulking and/or aspiration devices can be used to remove the obstruction. These mechanical techniques can either macerate, aspirate, or a combination thereof in order to remove the blood clots. An advantage of mechanical therapy is that it can remove thrombus directly from the blockage area and immediately eliminates the obstruction and may be superior to thrombolytic agents in some cases. However, current mechanical therapies have some major limitations. There is minimal to no flow during the procedure thus there is little time before patients may become hemodynamically instable. The debris removed from mechanical treatment can travel distally creating additional embolization. The small size devices are unable to remove large amount of blood clots in short time periods thus patients may become hemodynamically instable.

Catheter-based removal of blood clots from larger blood vessels (e.g., pulmonary arteries) have had limited success compared to smaller blood vessels (e.g., coronary arteries). Catheter pulmonary embolectomy is where pulmonary emboli are removed percutaneously using several techniques. Fragmentation thrombectomy breaks blood clots into smaller pieces, most of which travel further downstream, resulting in distal embolization. It is sometimes used in combination with thrombolytics. With the rheolytic thrombectomy, high velocity saline jets create a Venturi effect and draw the fragments of the clot into the catheter. This method poses risk of hemolysis. Finally the aspiration techniques draw the clot into a catheter via suction. All of these techniques rely on the catheter used to remove the clots from blood vessels. The users use small catheters to remove or break up large amounts of blood clot. This procedure is therefore time-consuming and inefficient. Once the blood clots are broken into small pieces, the debris can migrate distally and create unwanted emboli. Rheolytic therapy poses the risk of hemolysis. Additionally, the ability to suction is limited due the small catheter size suctioning large emboli. These limitations cause unnecessary duress to the user and risk to the patient.

Catheter-based removal of blood clots in general also has a major limitation when distal working space within a body lumen is limited. Conventional devices may require full axial and/or radial deployment and expansion to be functional, and as such flexibility to use such devices for a variety of clinical situations involving differing clot or other material sizes to be removed can be very limited. Therefore, conditions where there is limited distal space of blood vessels can render these conventional devices ineffective.

It is evident that all of the therapeutic options available to patients with blood clots or other undesirable material in blood vessels and other body lumens have limitations. Anticoagulation only limits propagation of clots but does not actively remove it. Thrombolytic therapy poses a risk of major bleeding. Catheter embolectomy is not effective to manage removal of material in large vessels. Additionally, these devices require distal space to fully deploy to be functional thus ineffective in tight distal spaces. Surgical embolectomy can be highly effective but highly invasive, and has a high rate of morbidity and mortality. There is a need for a direct mechanical treatment that is as or more effective as surgical embolectomy removing large blood clots but can be performed using endovascular techniques and restore immediate blood flow, and cause a lower incidence of complications.

SUMMARY

In some embodiments, disclosed herein is a capture system for selected materials within a body. The capture system can include a capture assembly configured to isolate unwanted material, e.g., a blood clot that can include a shape memory body such as made of, for example, a mesh material and having a distal end connected to a capture guide having a distal opening. The shape memory body can further include a proximal end connected to a first shaft, and a tubular sidewall between the proximal end and the distal end. The capture assembly can be configured to expand the capture guide and the distal opening end when the shape memory body proximal end is compressed in the delivery system. The shape memory body can be movable from a first configuration having a first axial length and a second configuration having a second axial length. The shape memory body can be configured to roll out, invert, evert, and/or variably lengthen proximally or distally from the first configuration to the second configuration. The second axial length can be different from the first axial length. The width of the capture assembly can, in some cases not substantially change from the first configuration to the second configuration. The capture system can also include a control line configured to independently move the capture assembly from the first configuration to the second configuration. The first shaft can extend within the longitudinal axis of the capture assembly.

In some embodiments, disclosed herein is a material, e.g., a clot capture system. The system can include a first, outer tubular shaft comprising a central lumen, the first outer tubular shaft comprising a proximal portion and a distal portion, the distal portion more radially expandable than the proximal portion. The system can also include a second tubular shaft configured to be positioned within the central lumen of the first shaft. The system can also include a third tubular shaft configured to be positioned within a central lumen of the second shaft. The shape memory tubular body can include a first end, a second end, and an axial length therebetween, the first end having a proximal-facing opening and a ring-shaped capture guide attached to a circumference of the proximal-facing opening, the capture guide operably attached to the second tubular shaft, the second end attached to an outer wall of the third tubular shaft. The shape memory tubular body can be compressed within the central lumen of the second tubular shaft in a first delivery configuration. The shape memory tubular body can be transformable to a second configuration in which the first end and the capture guide is radially expanded up to a dynamic fold point, but the second end and a segment of the shape memory tubular body extends in a different direction, such as proximally past the dynamic fold point, and remains radially compressed within the central lumen of the second tubular shaft and the second end is positioned proximal to the first end and the shape memory tubular mesh body has a first expanded axial length. The shape memory tubular body can be transformable to a third configuration in which the shape memory tubular body has a second expanded axial length greater than the first expanded axial length, and a width of the shape memory tubular shaft along its second expanded axial length is the same or substantially the same as a width of the shape memory tubular shaft along its first expanded axial length. The first tubular shaft can be configured to be reversibly coupled with respect to the second tubular shaft in the delivery configuration and axially movable with respect to the third tubular shaft in the second configuration. In some embodiments, the second expanded axial length is about or at least about, for example, 105%, 110%, 115%, 120%, 125%, 130%, 150%, 200%, 250%, 300%, 350%, 400%, 450%, 500%, or more of the first axial length. The capture system of claim 1, wherein the shape memory body can be porous, semi-permeable, and non-porous, and include nitinol braided, woven, or non-woven mesh, or nitinol wire. In some embodiments, the tubular body is coated with a hydrophilic or hydrophobic agent, or noncoated, and may not include a shape memory metal or material. In some embodiments, the tubular mesh body is configured to invert, evert, or roll out with respect to the first, second, and/or third shaft. The system can also include a control line extending proximally from the capture guide, either terminating on a sleeve on one of the shafts or extending proximally to the proximal end of the system. In some embodiments, the system includes a suction element configured to operably connect with the proximal opening of the shape memory tubular body. The system can also include a mechanical thrombectomy element, such as a macerator. The system can also include a filter collection chamber configured to collect and filter blood obtained from the suction element.

The system can further include an expanding guide catheter configured to receive the capture assembly in the form of a kit. The expanding guide element can include an open funnel distal tip, that can be porous in some embodiments to allow flow around the funnel distal tip.

In some embodiments, disclosed herein is a material, such as a clot capture system that can include a first, outer tubular shaft comprising a central lumen; a second tubular shaft configured to be positioned within the central lumen of the first shaft, the second tubular shaft comprising a proximal portion and a distal portion, the distal portion more radially expandable than the proximal portion; a third tubular shaft configured to be positioned within a central lumen of the second shaft; a tubular mesh comprising a first end, a second end, and an axial length therebetween, the first end having a proximal-facing opening and a ring-shaped capture guide attached to a circumference of the proximal-facing opening, the capture guide operably attached to the second tubular shaft, the second end attached to an outer wall of the third tubular shaft. The tubular mesh can be compressed within the central lumen of the second tubular shaft in a delivery configuration. The tubular mesh can also be transformable to a second configuration in which the first end and the capture guide is radially expanded but the second end and a portion, such as a minority, half, or a majority of the tubular mesh remains radially compressed within the central lumen of the second tubular shaft and the second end is positioned proximal to the first end and the tubular mesh has a first expanded axial length. The tubular mesh can be transformable to a third configuration in which the tubular mesh has a second expanded axial length greater than the first expanded axial length, wherein a width of the tubular mesh along its second expanded axial length is substantially the same as a width of the tubular mesh along its first expanded axial length, wherein the third tubular shaft extends distally through the proximal end opening as well as the second axial expanded length of the shape memory tubular body. In some embodiments, the tubular mesh is not under tension or substantially under tension in the second configuration or the third configuration defining an axial working range of the tubular mesh.

In some embodiments, a material, such as a clot capture system includes a first, outer tubular shaft comprising a central lumen; a second tubular shaft configured to be positioned within the central lumen of the first shaft, the second tubular shaft comprising a proximal portion and a distal portion, the distal portion more radially expandable than the proximal portion; a third tubular shaft configured to be positioned within a central lumen of the second shaft; a tubular body that may include shape memory materials that includes a first end, a second end, and an axial length therebetween, the first end having a proximal-facing opening and a ring-shaped capture guide attached to a circumference of the proximal-facing opening, the capture guide operably attached to the second tubular shaft via a sleeve circumscribing a portion of the second tubular shaft, the second end attached to an outer wall of the third tubular shaft. The shape memory tubular body can be compressed within the central lumen of the second tubular shaft in a delivery configuration. The shape memory tubular body can be transformable to a second configuration by axial movement of the second tubular shaft with respect to the first tubular shaft, in which the first end and the capture guide is radially expanded but the second end and a segment of the shape memory tubular body remains radially compressed within the central lumen of the second tubular shaft and the second end is positioned proximal to the first end and the shape memory tubular mesh body has a first expanded axial length. The shape memory tubular body can be transformable to a third configuration by movement of the second tubular shaft with respect to the third tubular shaft, in which the shape memory tubular body has a second expanded axial length greater than the first expanded axial length, wherein a width of the shape memory tubular shaft along its second expanded axial length is substantially the same as a width of the shape memory tubular shaft along its first expanded axial length, wherein the third tubular shaft extends distally through the proximal end opening as well as the second axial expanded length of the shape memory tubular body. The shape memory tubular body can, in some cases, be transformable to a fourth configuration by movement of the second tubular shaft with respect to the third tubular shaft. The shape memory tubular body can have a third expanded axial length greater than the second expanded axial length, wherein a width of the shape memory tubular shaft along its third expanded axial length is less than the width of the shape memory tubular shaft along its second expanded axial length. The clot capture system can also include a sleeve that includes a metal or polymer, and the sleeve can be partially or fully radiopaque or radiolucent under fluoroscopy or other imaging.

Also disclosed herein is a method of performing a thrombectomy. The method can include, for example, accessing the interior of a blood vessel; advancing a thrombus capture device comprising a capture assembly through the blood vessel; positioning the thrombus capture device such that a distal end of the device is distal to the thrombus; actuating the capture assembly to isolate the thrombus within the capture device, wherein the capture assembly is movable from a first configuration having a first axial length and a second configuration having a second axial length, the second axial length being different from the first axial length, wherein the width of the capture assembly does not substantially change from the first configuration to the second configuration; and suctioning, macerating, and/or mechanically removing the thrombus.

In some embodiments, a method of performing a thrombectomy can include, for example, accessing the interior of a blood vessel; advancing an expanding guiding catheter through the blood vessel; positioning the expanding guiding catheter such that a distal end of the device is proximal to a thrombus; retracting the expanding guide catheter outer member to expand a funnel tip and exposing an expandable inner member; advancing a thrombus capture device comprising a capture assembly through the expanding guide catheter; positioning the thrombus capture device such that a distal end of the device is distal to or within the thrombus; and actuating the capture assembly to isolate the thrombus within the capture device. The capture assembly can be movable from a first configuration having a first axial length and a second configuration having a second axial length, the second axial length being different from the first axial length. The width of the capture assembly may not substantially change from the first configuration to the second configuration. The method can also include retracting the capture assembly with the thrombus into an expanding guide catheter funnel tip and expandable inner body. The method can also include axially lengthening the thrombus capture device distally and retracting the thrombus into the funnel tip of the expanding guide catheter. The method can further include radially shortening the thrombus capture device to compress the thrombus and promote removal of the thrombus.

In some embodiments, disclosed herein is a clot capture system that can include a capture assembly configured to isolate a blood clot. The system can include a shape memory body that has a distal end connected to a capture guide comprising a distal or proximal opening. The shape memory body can also include a proximal end connected to a first shaft, and a sidewall between the proximal end and the distal end. The capture guide and the distal zone of the shape memory body opening end can also be fully or partially recaptured inside the outer sheath. The capture assembly can be configured to radially expand the capture guide and a distal zone of the shape memory body opening end while the shape memory body proximal end remains compressed in the delivery configuration. The capture assembly can be movable from a first configuration having a first axial length to a second configuration having a second axial length. The shape memory body can be configured to roll out, invert, evert, and/or variably lengthen proximally from the first configuration to the second configuration. The second axial length can be different from the first axial length. The width of the capture assembly can in some cases not substantially change from the first configuration to the second configuration.

Also disclosed herein is a capture assembly configured to isolate a blood clot including a shape memory body including a proximal end and a distal end connected to a capture guide including a distal opening, a proximal end connected to a shaft, and a sidewall between the proximal end and the distal end. The capture assembly can be configured to expand the capture guide and the distal shape memory body opening end while the shape memory body proximal end is compressed in the delivery configuration between a first shaft and a second shaft, and movable from a first configuration having a first axial length and a second configuration having a second axial length. The shape memory body can be configured to roll out/unroll, invert, evert, and/or variably lengthen proximally from the first configuration to the second configuration. The second axial length can be different from the first axial length. In some cases, the width of the capture assembly does not substantially change from the first configuration to the second configuration. Furthermore, the shape memory body can be fully or partially recaptured inside the outer sheath once deployed. The system can also include a sleeve coupled a control line connected to the second shaft configured to move the capture assembly from the first configuration to the second configuration. The first shaft and the second shaft can be off-axis with respect to the capture assembly.

Also disclosed herein is a method of performing a thrombectomy. The method can include any number of the following: accessing the interior of a blood vessel; advancing a thrombus capture device comprising a capture assembly through the blood vessel; positioning the thrombus capture device such that a distal end of the device is distal to the thrombus; actuating the capture assembly to isolate the thrombus within the capture device, wherein the capture assembly is movable from a first configuration having a first axial length and a second configuration having a second axial length, the second axial length being different from the first axial length, wherein the width of the capture assembly does not substantially change from the first configuration to the second configuration; and suctioning the thrombus.

In some embodiments, the methods can include any number of the following: accessing the interior of a blood vessel; advancing an expanding guiding catheter through the blood vessel; positioning the expanding guiding catheter such that a distal end of the device is proximal to a thrombus; retracting the expanding guide catheter outer member to expand a funnel tip and exposing an expandable inner member; advancing a thrombus capture device comprising a capture assembly through the expanding guide catheter; positioning the thrombus capture device such that a distal end of the device is distal to or within the thrombus; actuating the capture assembly to isolate the thrombus within the capture device, wherein the capture assembly is movable from a first configuration having a first axial length and a second configuration having a second axial length, the second axial length being different from the first axial length wherein the width of the capture assembly does not substantially change from the first configuration to the second configuration; and retracting the thrombus into an expanding guide catheter funnel tip and expandable inner body. In some embodiments, the capture guide is first recaptured into the outer sheath of the delivery catheter and then retract into the expanding guide catheter funnel tip and expandable inner body.

In some embodiments, disclosed herein is a clot capture system. The system can include a first tubular member comprising a central lumen. The system can include a second tubular member. The system can include a shape memory tubular body comprising a first end, a second end, and an axial length therebetween, the first end having an end opening, the second end attached to the second tubular member. In some embodiments, at least part of the shape memory tubular body is compressed within the central lumen of the first tubular shaft in a first delivery configuration. In some embodiments, the shape memory tubular body is transformable to a second configuration in which the first end is radially expanded while the second end and a majority of the shape memory tubular body remains radially compressed within the central lumen of the first tubular shaft and the second end is positioned proximal to the first end and the shape memory tubular body has a first expanded axial length. In some embodiments, the shape memory tubular body is transformable to a third configuration via movement of the first tubular shaft with respect to the second tubular shaft in which the shape memory tubular body has a second expanded axial length greater than the first expanded axial length, wherein a width of the shape memory tubular body along its second expanded axial length is substantially the same as a width of the shape memory tubular body along its first expanded axial length.

The system can include a capture guide attached to the first end opening. In some embodiments, the capture guide at least partially circumscribes the first end opening. In some embodiments, the capture guide fully partially circumscribes the first end opening. The system can include an expandable cover element circumscribing the capture guide. In some embodiments, the expandable cover element is inflatable. The system can include a control line extending proximally from the capture guide. The system can include a sleeve attached to the first tubular shaft and the first end opening of the shape memory tubular body. In some embodiments, the shape memory tubular body is configured to invert, evert, or roll out with respect to the first tubular shaft or the second tubular shaft. In some embodiments, the end opening of the shape memory tubular body is proximal-facing. In some embodiments, the shape memory tubular body comprises a mesh. In some embodiments, the shape memory tubular body is configured to allow fluid flow therethrough. In some embodiments, the second tubular member comprises a central lumen. The system can include an expanding guide element configured to receive the capture assembly. In some embodiments, the expanding guide element comprises an open funnel distal tip. In some embodiments, the open funnel distal tip is porous to allow flow. In some embodiments, the shape memory tubular body has a maximal length of between about 0.5 cm and about 125 cm. In some embodiments, the shape memory tubular body is transformable to a fourth configuration wherein the shape memory tubular body has a third axial expanded length greater than the second axial expanded length, wherein a width of the shape memory tubular body along its third expanded axial length is less than the width of the shape memory tubular body along its second expanded axial length.

In some embodiments, disclosed herein is a system for capturing material of interest within a body lumen. The system can include a first tubular member comprising a central lumen. The system can include a second tubular member. The system can include a shape memory tubular body comprising a first end, a second end, and an axial length therebetween, the first end having an end opening, the second end attached to an outer wall of the second tubular member. In some embodiments, the shape memory tubular body is compressed within the central lumen of the first tubular shaft in a first delivery configuration. In some embodiments, the shape memory tubular body is transformable to a second configuration in which the first end opening and a first segment of the shape memory tubular body extending axially in a first direction from the first end opening is radially expanded to a fold point, while a second segment of the shape memory tubular body extends axially from the fold point to the second end of the shape memory tubular body in a second direction opposite the first direction, the second segment relatively radially compressed with respect to the first segment, the second end positioned proximal to the first end. In some embodiments, the shape memory tubular body is transformable to a third configuration via movement of the first tubular shaft with respect to the second tubular shaft in which the axial length of the first segment increases by a first amount, the shape memory tubular body has a second expanded axial length greater than the first expanded axial length, wherein a width of the shape memory tubular body along its second expanded axial length is substantially the same as a width of the shape memory tubular body along its first expanded axial length.

In some embodiments, disclosed herein is a clot capture system. The system can include a first tubular member comprising a central lumen. The system can include a second tubular member. The system can include a shape memory tubular body comprising a first end, a second end, and an axial length therebetween, the first end having an end opening, the second end attached to an outer wall of the second tubular member. In some embodiments, the shape memory tubular body is compressed within the central lumen of the first tubular shaft in a first delivery configuration. In some embodiments, the shape memory tubular body is transformable to a second configuration in which the first end opening and a first segment of the shape memory tubular body extending axially in a first direction from the first end opening is radially expanded to a fold point, while a second segment of the shape memory tubular body extends axially from the fold point in a second direction opposite the first direction to the second end, the second segment radially compressed with respect to the first segment, the second end positioned proximal to the first end. In some embodiments, the shape memory tubular body is transformable to a third configuration via movement of the first tubular shaft with respect to the second tubular shaft in which the axial length of the first segment increases by a first amount, the shape memory tubular body has a second expanded axial length greater than the first expanded axial length, wherein a width of the shape memory tubular body along its second expanded axial length is substantially the same as a width of the shape memory tubular body along its first expanded axial length.

In some embodiments, disclosed herein is a clot capture system. The system can include an outer sheath comprising a central lumen. The system can include a dual lumen shaft configured to be positioned within the central lumen of the outer sheath. The system can include an inner pusher configured to be positioned within a first lumen of the dual lumen shaft. The system can include an anchor pusher configured to be positioned within a second lumen of the dual lumen shaft. The system can include an anchor coupled to the anchor pusher. The system can include a shape memory tubular body comprising a first end, a second end, and an axial length therebetween, the first end having an opening and a capture guide attached to a portion of the opening. In some embodiments, the shape memory tubular body and the anchor are compressed in a first configuration. In some embodiments, the shape memory tubular body is transformable to a second configuration in which the first end and the capture guide are radially expanded but the second end and a majority of the shape memory tubular body remains radially compressed within the lumen of the dual lumen shaft and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length, wherein the shape memory tubular body encapsulates the anchor in the third configuration.

The system can include, for example, one, two, or more anchors. The anchors can have any desired configuration to stabilize or associate with a clot to facilitate removal, including a J-hook shape in some cases. In some embodiments, the anchors have a central longitudinal axis that is coaxial. The system can include three anchors, or more. In some embodiments, the cross-section of the anchor is round, ovoid, square, rectangular, or another cross section. In some embodiments, the anchor comprises nitinol. In some embodiments, the anchor forms an angle with the anchor pusher, wherein the angle is approximately 90 degrees. In some embodiments, the anchor forms an angle with the anchor pusher, wherein the angle is approximately 45 degrees. In some embodiments, the anchor forms an angle with the anchor pusher, wherein the angle is between 5 degrees and 135 degrees. In some embodiments, the diameter of the anchor is less than the diameter of the shape memory tubular body when radially expanded. In some embodiments, a portion of the anchor pusher is crescent shaped. In some embodiments, the capture guide comprises nitinol. In some embodiments, the capture guide comprises a central longitudinal axis and wherein the dual lumen shaft is offset from the central longitudinal axis. In some embodiments, the second end of the shape memory tubular body is coupled to the inner pusher. In some embodiments, the capture guide forms a continuous loop. In some embodiments, the capture guide forms a non-continuous loop.

In some embodiments, disclosed herein is a clot capture system. The system can include an inner pusher. The system can include a shape memory tubular body comprising a first end, a second end, and an axial length therebetween, the first end having an opening and a capture guide attached to at least a portion of the opening, the second end coupled to the inner pusher. In some embodiments, the shape memory tubular body and the capture guide are compressed in a first configuration. In some embodiments, the shape memory tubular body is transformable to a second configuration in which the first end and the capture guide are radially expanded but the second end and a majority of the shape memory tubular body remains radially compressed and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length. In some embodiments, the capture guide forms a continuous loop. In some embodiments, the capture guide forms a non-continuous loop.

Also disclosed herein is a method of using a clot capture system. The method can include any number of the following: positioning a system near a blood clot in the first configuration; transforming the shape memory tubular body to the second configuration; and transforming the shape memory tubular body to the third configuration to encapsulate the clot. The system can include an inner pusher. The system can include a shape memory tubular body comprising a first end, a second end, and an axial length therebetween, the first end having an opening and a capture guide attached to at least a portion of the opening, the second end coupled to the inner pusher. In some embodiments, the shape memory tubular body and the capture guide are compressed in a first configuration. In some embodiments, the shape memory tubular body is transformable to a second configuration in which the first end and the capture guide are radially expanded but the second end and a majority of the shape memory tubular body remains radially compressed and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length. In some embodiments, the blood clot is within the CNS.

Also disclosed herein is a method of using a clot capture system. The method can include any number of the following: positioning a system near a blood clot; transforming the shape memory tubular body to the second configuration; expanding the anchor; and transforming the shape memory tubular body to the third configuration to encapsulate the anchor. The system can include an outer sheath comprising a central lumen. The system can include a dual lumen shaft configured to be positioned within the central lumen of the outer sheath. The system can include an inner pusher configured to be positioned within a first lumen of the dual lumen shaft. The system can include an anchor pusher configured to be positioned within a second lumen of the dual lumen shaft. The system can include an anchor coupled to the anchor pusher. The system can include a shape memory tubular body comprising a first end, a second end, and an axial length therebetween, the first end having an opening and a capture guide attached to a portion of the opening. In some embodiments, the shape memory tubular body and the anchor are compressed in a first configuration.

In some embodiments, the shape memory tubular body is transformable to a second configuration in which the first end and the capture guide are radially expanded but the second end and a majority of the shape memory tubular body remains radially compressed within the lumen of the dual lumen shaft and the shape memory tubular body has a first expanded axial length with a first cross-section, wherein the first cross-section is substantially similar to the cross-section of the capture guide. In some embodiments, the shape memory tubular body is transformable to a third configuration in which the shape memory tubular body has a second expanded axial length greater than the first expanded axial length, wherein the shape memory tubular body encapsulates the anchor in the third configuration. In some embodiments, deploying the anchor comprises securing the anchor within the clot. In some embodiments, transforming the shape memory tubular body to the third configuration to encapsulate the anchor further comprises encapsulating the clot. In some embodiments, the blood clot is a neurological blood clot.

In some embodiments, disclosed herein is a clot capture system. The system can include a first tubular member comprising a central lumen. The system can include a second tubular member. The system can include a plurality of axially spaced-apart anchors extending radially outwardly from the first tubular member or the second tubular member. The system can include a shape memory tubular body comprising a first end, a second end, and an axial length therebetween, the first end having an end opening, the second end attached to the second tubular member. In some embodiments, at least part of the shape memory tubular body is compressed within the central lumen of the first tubular shaft in a first delivery configuration. In some embodiments, the shape memory tubular body is transformable to a second configuration in which the first end is radially expanded while the second end and a majority of the shape memory tubular body remains radially compressed within the central lumen of the first tubular shaft and the second end is positioned proximal to the first end and the shape memory tubular body has a first expanded axial length. In some embodiments, the shape memory tubular body is transformable to a third configuration via movement of the first tubular shaft with respect to the second tubular shaft in which the shape memory tubular body has a second expanded axial length greater than the first expanded axial length, wherein a width of the shape memory tubular body along its second expanded axial length is substantially the same as a width of the shape memory tubular body along its first expanded axial length.

BRIEF DESCRIPTION OF THE FIGURES

FIG. 16A illustrates another embodiment of the axial lengthening thrombus capture device in the delivery configuration, according to some embodiments of the invention.

FIG. 16B illustrates the axial lengthening thrombus capture device in the initial deployed configuration wherein the outer sheath is retracted to expanded the axial lengthen thrombus capture device. The loop is coupled to the sleeve wherein it is coupled to the capture catheter shaft, according to some embodiments of the invention.

FIG. 16C illustrates the axial lengthening thrombus capture device retracting proximally and lengthening, according to some embodiments of the invention.

FIG. 16D illustrates the lengthening of the axial lengthening thrombus capture device and in some cases at full deployment, according to some embodiments of the invention.

FIGS. 17A-D illustrate different configurations of the ALTC device, according to some embodiments of the invention.

FIGS. 18A-B illustrate an embodiment of a distal portion of the axially-lengthening thrombus capture system with a cover element radially outward of, and partially or completely circumscribing the capture guide of the ALTC device, which can be in the shape of a ring as illustrated.

FIG. 27 illustrates an embodiment of a key cap feature to enable an anti-rotation of the hypotube pusher.

FIGS. 49A and 49B illustrate another embodiment of the axial lengthening thrombus capture device wherein the guidewire lumen and capture catheter is offset to the longitudinal axis of the axial lengthening thrombus capture device, according to some embodiments of the invention.

FIGS. 50A-50G illustrate an embodiment of the retrieval of thrombus into the expanding guide catheter wherein the ALTC device lengthens distally and creates additional space and the thrombus is redistributed and enable better retrieval into the expanding guide catheter. The funnel tip and expanding section of the expanding guide catheter also facilitate the ease of thrombus retrieval.

FIG. 53 illustrates the distal end of the capture device of the system of FIG. 51 in an initial deployed configuration.

FIG. 54 illustrates the distal end of the capture device of the system of FIG. 51 in a second configuration.

FIG. 55 illustrates the distal end of the capture device of the system of FIG. 51 in a third configuration.

FIG. 56 illustrates an embodiment of the basket mesh element of the system of FIG. 51. The basket mesh element can made of metallic materials such as Nitinol. The mesh element can be braided or laser cut.

FIG. 57 illustrates an embodiment of a capture device element of the system of FIG. 51.

FIGS. 58A-58B illustrate embodiments of an expandable loop element of the system of FIG. 51.

FIG. 61 illustrates an embodiment of a system.

FIG. 62 illustrates a distal end of the capture device system of the system of FIG. 61.

FIG. 63 illustrates a proximal end of the system of FIG. 61.

FIG. 64 illustrates an anchor assembly of the system of FIG. 61.

FIG. 68A illustrates the capture device of the system of FIG. 61 in an initial deployed configuration.

FIG. 68B illustrates the capture device and first anchor release of the system of FIG. 61 when the outer sheath retracts proximally.

FIG. 68C illustrates the capture device, first anchor, and second anchor release of the system of FIG. 61 when the outer sheath is retracted.

FIG. 68D illustrates the capture device, first anchor, second anchor, and third anchor release of the system of FIG. 61 when the outer sheath is retracted.

FIG. 69A illustrates the capture device of the system of FIG. 61 in an initial deployed configuration and the anchors are fully released.

FIG. 69B illustrates the capture device of the system of FIG. 61 lengthened proximally to encapsulate the first anchor.

FIG. 69C illustrates the capture device of the system of FIG. 61 lengthened proximally to encapsulate the anchors.

DETAILED DESCRIPTION

The present invention provides, in some embodiments, systems and methods that can be delivered percutaneously in a body to retrieve and removal materials including blood clots, stones/calculi, and/or foreign materials in a body lumen, including a blood vessel, such as an arterial vessel or a venous vessel within the circulatory system. The present invention can, in some embodiments, also apply to nonvascular areas to treat, for example, gallstones, kidney stones, common bile duct stones, and the like.

Figure 1:
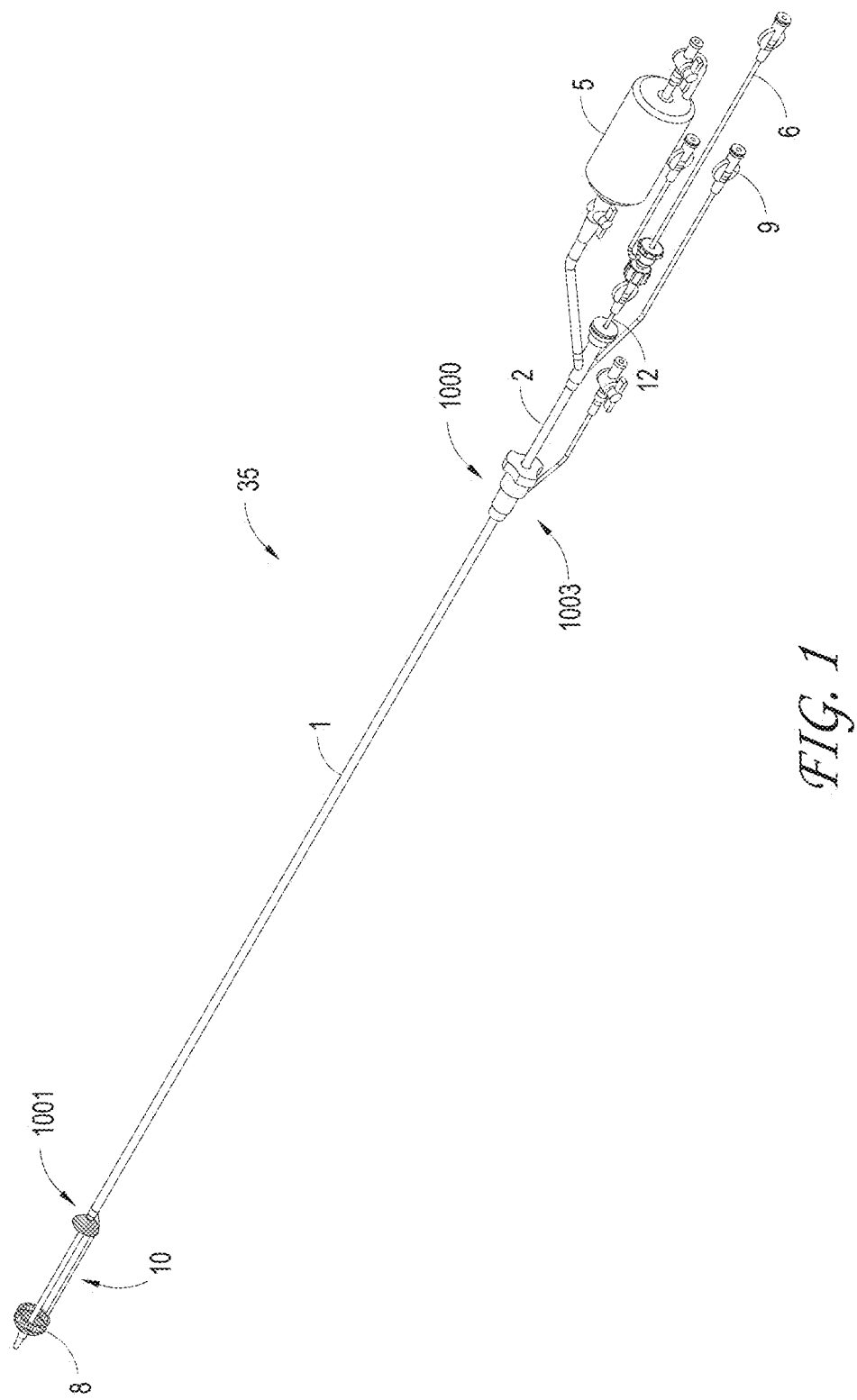
FIG. 1 illustrates examples of a catheter system, and various possible elements that can be included in a material capture system, according to some embodiments of the invention.

Systems can be delivered percutaneously, via a cut-down approach, a thoracoscopic approach, or via other approaches, for example, using a catheter system 35, of which a perspective view of an embodiment is shown in FIG. 1. FIG. 1 also illustrates examples of various possible elements that can be included in a material capture system, according to some embodiments of the invention. As illustrated in FIG. 1, included in some embodiments are any number of, such as one, two, or more of the following components: a first tubular member, such as an outer sheath 1, a second tubular member, such as a capture catheter 12, a third tubular member, such as a guidewire tube 6 an axial lengthening thrombus capture device 8, a suction catheter 2, and a filter collection chamber 5. The outer sheath 1 can, in some embodiments, be an elongate tubular member with a central lumen therethrough, and have a proximal end 1000 and a distal end 1001. The distal end 1001 of the outer sheath 1 can be operably connected to a capture device (e.g., tubular mesh 8), which can be movably axially with respect to the outer sheath 1. In some embodiments, the outer sheath 1 has a relatively rigid proximal portion and a distal portion that is more flexible than the relatively rigid proximal portion, which can be advantageous to flexibly expand if necessary to accommodate the passage of large clots and/or other materials. The proximal end 1000 of the outer sheath 1 can connect to a proximal hub 1003 that may include any number of: the suction catheter 2, capture catheter 12, guidewire tube 6, and filter collection chamber 5. Non-limiting examples of other optional elements that can be included in the system (not shown in FIG. 1) include a macerator tool (described elsewhere herein) and a discrete expanding guide catheter (described elsewhere herein. In some embodiments, the outer sheath 1 has a lumen configured to house the suction catheter 2, which in turn has a lumen configured to house the capture catheter 4, which in turn has a lumen configured to house the guidewire tube/ guidewire lumen assembly 6 and the axial lengthening thrombus capture device (ALTC device) 8, which in turn has a lumen configured to house a guidewire (not shown) therethrough. An ALTC device as defined herein can include any structure, such as a net-like structure for example, configured to capture materials within a body location and axially lengthen and shorten through a working range, with or without radially shortening in width or diameter throughout that working range depending on the desired clinical result. In some embodiments, the outer sheath 1 has an inner diameter configured to house the capture catheter 12 coaxially therein, and the capture catheter 12, which in turn has a lumen configured to house the guidewire tube 6 and the body of the ALTC device 8. The ALTC device 8 can in some embodiments including a mesh net-like structure with a proximal-facing opening at one end that can be made of a shape memory metal or polymer, a non-shape memory metal such as stainless steel, or another non-shape memory fabric, embodiments of which are described in detail elsewhere herein. In some embodiments, conventional net-like structures such as used in IVC and other embolic filters can be utilized with systems and methods herein. In some embodiments, a thrombus capture device can be configured in some embodiments to axially lengthen throughout a working range, with or without radially shortening the device throughout the working range.

Figure 2:
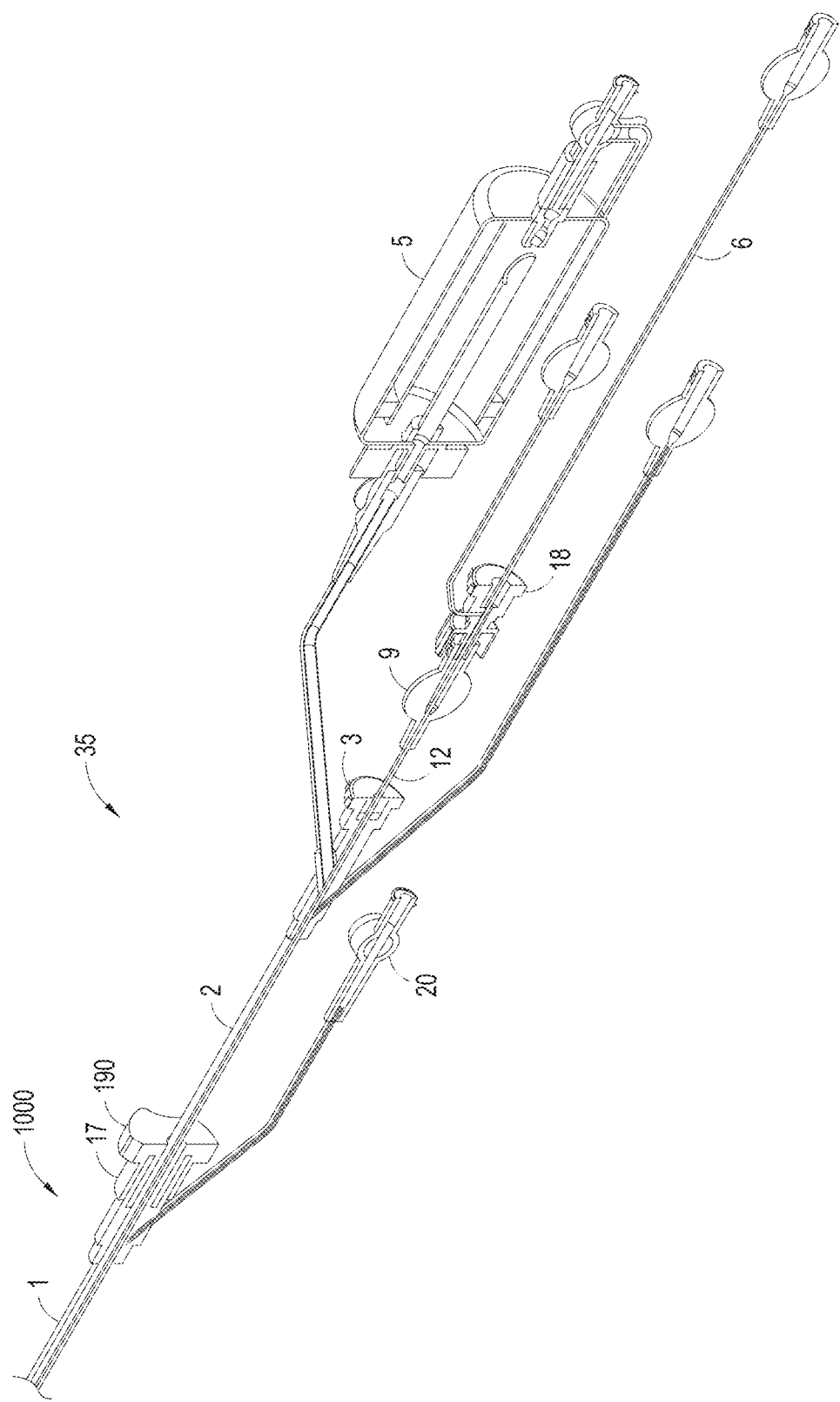
FIG. 2 illustrates a close-up view of the thrombus capture systems of FIGS. 1 and 2.

FIG. 2 illustrates a close-up view of the proximal end 1000 of the thrombus capture systems of FIG. 1. Illustrated is outer sheath 1 configured to, in some embodiments, house suction catheter 2 therethrough. Also illustrated is the proximal end of the outer sheath 1 which can terminate in a connector 17 and hemostasis seal 190, of which another tube, such as the suction catheter 2 (and/or capture catheter 4) can be inserted coaxially into. The proximal end of the suction catheter 2 can also include a connector 3 having a seal, and a lumen of which the capture catheter 12 can be inserted into. The capture catheter 4 can also include a connector with a seal 18 at its proximal end. The guidewire tube 6 with a lumen to house a guidewire therethrough can be configured to fit coaxially within the capture catheter shaft 12. Also illustrated is an optional filter collection chamber 5 with a lumen fluidly connected to a lumen of the suction catheter 2. A proximal hub 17 is also illustrated, as well as a flush port 20. In some embodiments, suction is not required (and as such a suction catheter 2 is not included in the system), and the clot or other materials can be captured either mechanically, hydraulically and/or maceration via the ALTC device 8.

Figure 3:
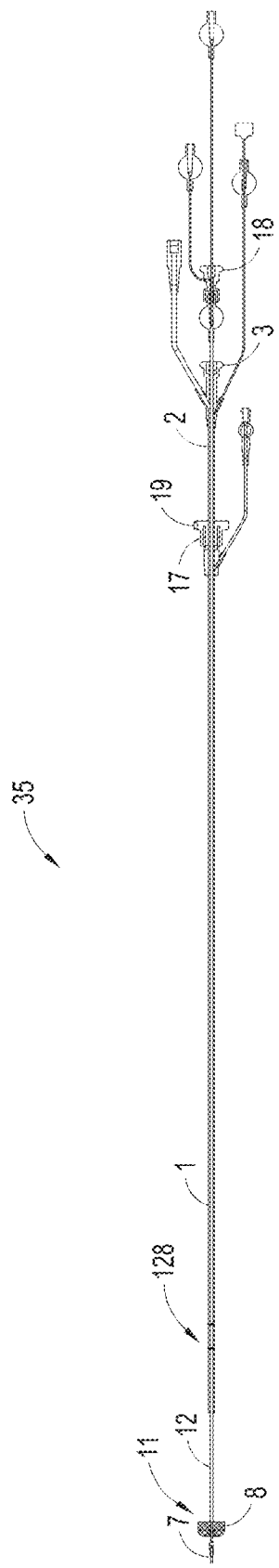
FIG. 3 illustrates an axially-lengthening thrombus capture (ALTC) system in the initial deployment configuration with the ALTC device expanded, according to some embodiments of the invention.

FIG. 3 illustrates an axially-lengthening thrombus capture system 35 in the initial deployment configuration with the ALTC device 8 radially expanded, according to some embodiments of the invention. Also illustrated is nose tip 7 distal to the ALTC device 8. Relative axial movement of the outer tube 1 with respect to capture catheter 4 can allow for transformation of a first end (e.g., an expanded proximal end with a proximal-facing opening, or distal or laterally facing opening in other embodiments) of the ALTC device 8 from a radially compressed to a radially expanded configuration. In some embodiments, the proximal end opening of the ALTC device 8 includes a capture guide 11 that takes the form of, in some embodiments, a radially expandable shape memory partial or full ring-like annular structure that expands once free of the sidewall of the outer tube 1 along with a portion of the ALTC device mesh 8 attached to the capture guide 11. In the illustrated configuration, however, a significant portion of the surface area and/or the axial length of the mesh of the ALTC device remains in a compressed configuration within the lumen of the capture catheter 4, as the other end of the ALTC device mesh 8 is still operably attached, such as fixed to the outer diameter sidewall of the guidewire catheter 6.

Figure 4:
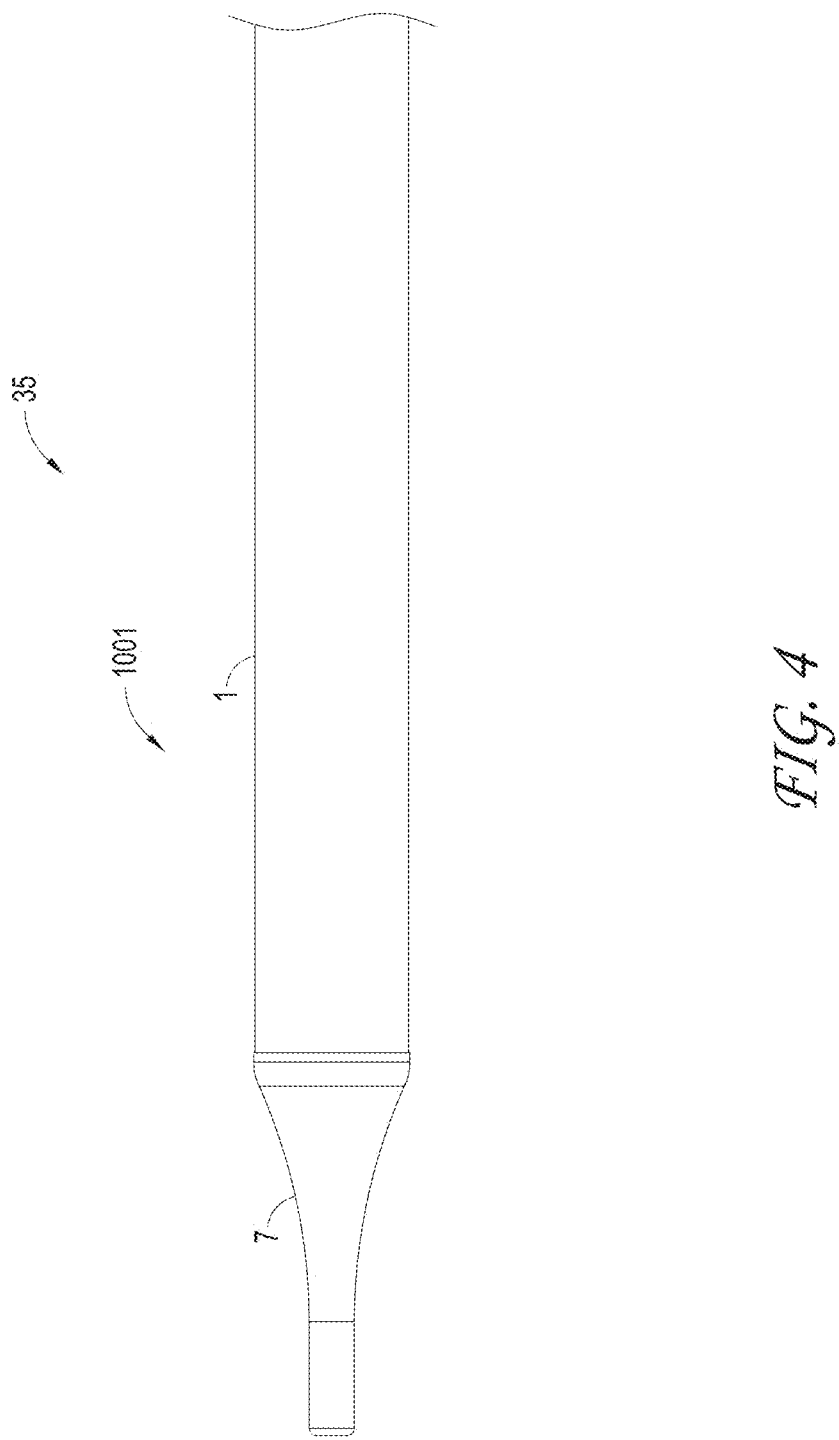
FIG. 4 illustrates a close up view of the ALTC system distal segment position in the delivery configuration indicating the outer sheath and nose tip, according to some embodiments of the invention.

FIG. 4 illustrates a close up view of the distal end of the ALTC catheter system 35 in the delivery configuration including the distal end 1001 of the outer sheath 1 and nose tip 7, which can be atraumatic and tapered as shown, according to some embodiments of the invention.

The ALTC Device 8 can function to retrieve and capture materials such as thromboemboli. The capture catheter 4 is shown, along with the ALTC Device 8, capture catheter shaft body 12, pull wire 10, and thrombus capture guide 11.

As illustrated in FIGS. 5-9 for example, a thrombus capture guide 11 can attach to a portion, such as an open end of the ALTC Device 8 and one, two, or more capture pull wires 10 where the capture pull wires are positioned inside the side lumen of the suction catheter 2 or outside of the lumen in other embodiments, and extends proximally. The distal end of the capture pullwire 10 can be connected to the proximal end of the ALTC device 8 at the capture guide 11 as illustrated. The capture pullwire 10 can extend proximally through the length of the outer sheath 1, and the proximal end of the pullwire 10 can be pushed or pulled allow a user to control, such as adjust the axial length of the ALTC device 8, for example when axially elongating the ALTC device in a proximal direction. In some embodiments, the capture pullwire 10 and the capture guide 11 are the only elements attached to the proximal end of the ALTC device 8. In some embodiments, the capture pullwire 10 and the capture guide 11 can be made into a single component such as a Loop. In some other embodiments, the capture guide and the proximal end of the ALTC device is sutured in place using silk or polymeric filaments such as Ultra-High Molecular Weight polyethylene, Nylon, PET, PTFE. In some embodiments, the open end of the ALTC device is covered with a low durometer film or coating and is then folded over the capture guide 11 and suture to secure the assembly. In another embodiment, the open end of the ALTC device 8, capture guide 11 and sutured assembly is coated with a low durometer polymeric materials. Another method to secure the wire ends is to apply polymeric fabric either on the outer or inner surface of the tubular structure and secure via suturing in place with suture filaments. The fabric can be at least one piece initially wrapped either on the inner or outer surface of the tubular structure and then folded over to the opposite side to secure and protect with wire ends. The two sides of the fabric can secured to the tubular structure using suture filament. Other means of securing the fabric to the tubular structure such as thermal bonding, press, lamination, chemicals, mechanical securement, and lasers can be used in some embodiments. The closed end of the ALTC device can be attached to an outer surface of the guidewire tube 6, which in turn can be positioned within a lumen of the capture catheter shaft 12. As such, axial elongation of the ALTC device in a distal direction can be achieved by, for example, movement of the guidewire tube 6 and pullwire 10 distally with respect to the capture catheter shaft 12. The axial elongation of the ALTC device in a proximal direction can be achieved by, for example, movement of the capture pullwire and capture catheter shaft proximally. The Thrombus Capture Guide 11 can be formed, for example, from metallic, shape memory, or other appropriate materials. In some embodiment, the thrombus capture guide 11 can include a loop configuration and be formed from nitinol shape memory wire of various geometries such as round, oval, elliptical, flat, and the like. The thrombus capture guide 11 can be formed of different shapes such as a circular loop, oval loop, z-shape, etc. In some embodiment, the loop 11 can be shaped set either into coils, multiple full circles, full circle or partial circles where the ends of the wire formed into two legs. The partial circle can be from, for example, 180 degrees to 359 degrees or 220 degrees to 359 degrees. The legs can be configured to be off-axis to the loop such that it can be right angle, acute or obtuse angle relative to the loop. It can be arcuate and form a partial or full ring as illustrated, and can circumscribe or otherwise form an outer diameter, and define the proximal-most end of the ALTC Device 8. The thrombus capture guide 11 can in some embodiments include a single loop or multiple loops positioned along the length of the ALTC Device 8 and not necessarily be present or have the entire guide 11 at the proximal-facing end opening end of the ALTC device 8. In some embodiments, the thrombus capture guide 11 does not include a loop. The ALTC Device tubular structure can be configured to be compressed and positioned within the Capture Catheter Shaft 12 lumen during introduction into the vascular system where the Capture Catheter Shaft 12 is configured to be positioned coaxially within and extend through the tubular structure and thrombus capture guide 11.

Figure 5:
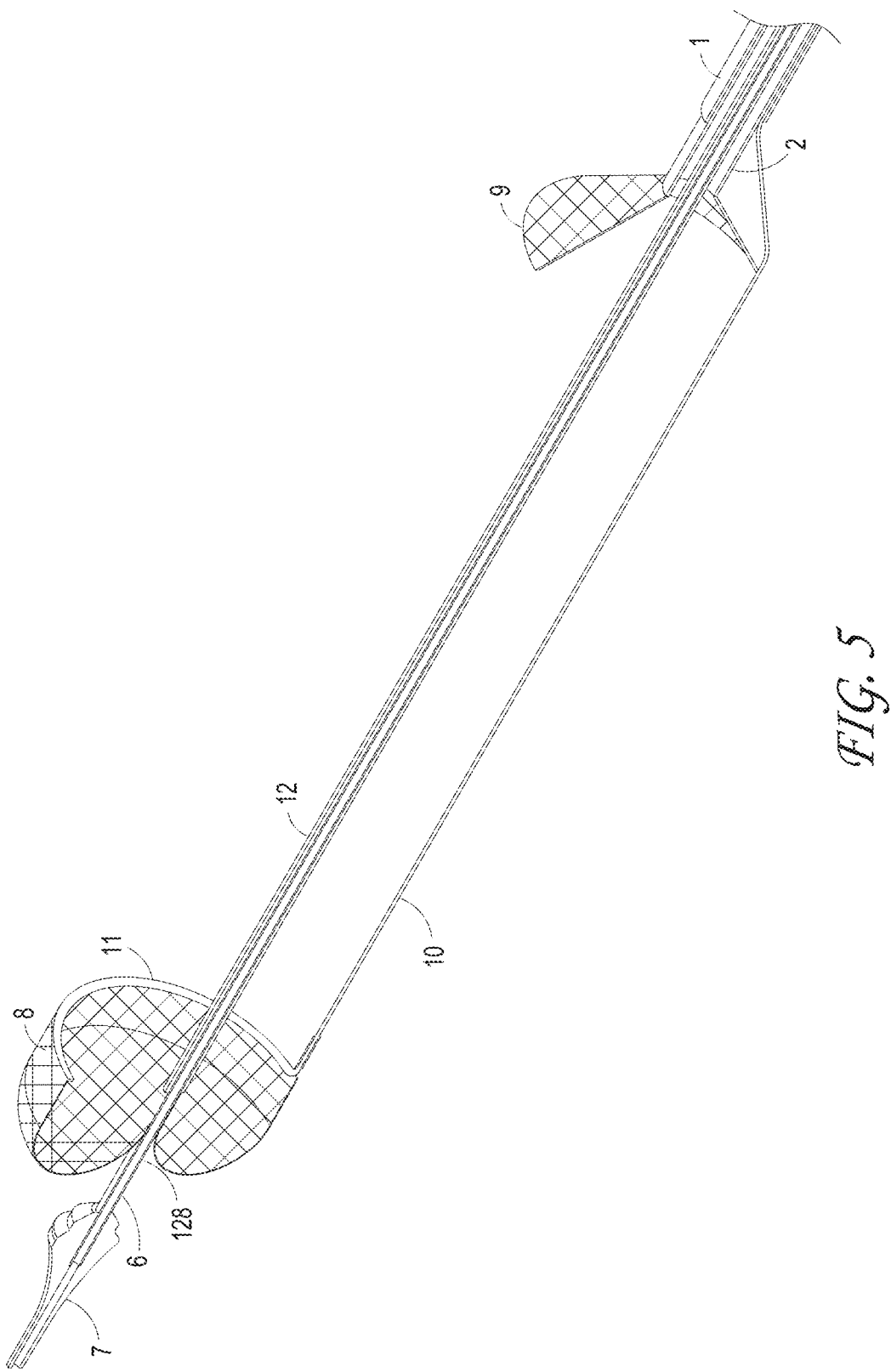
FIG. 5 illustrates the distal end of an axial lengthening thrombus capture device at the initial deployment position, according to some embodiments of the invention.

As illustrated in FIG. 5, the Axial Lengthening Thrombus Capture Device (ALTC Device) 8 can be in some embodiments a generally tubular net-like mesh structure that is collapsible, expandable and configured to axially lengthen or shorten, such as within a working range, while maintaining or substantially maintaining its diameter within the working range to retrieve and capture foreign or otherwise unwanted materials within the body, including the vascular system such as blood clots, thrombus and/or foreign materials.

Figure 6:
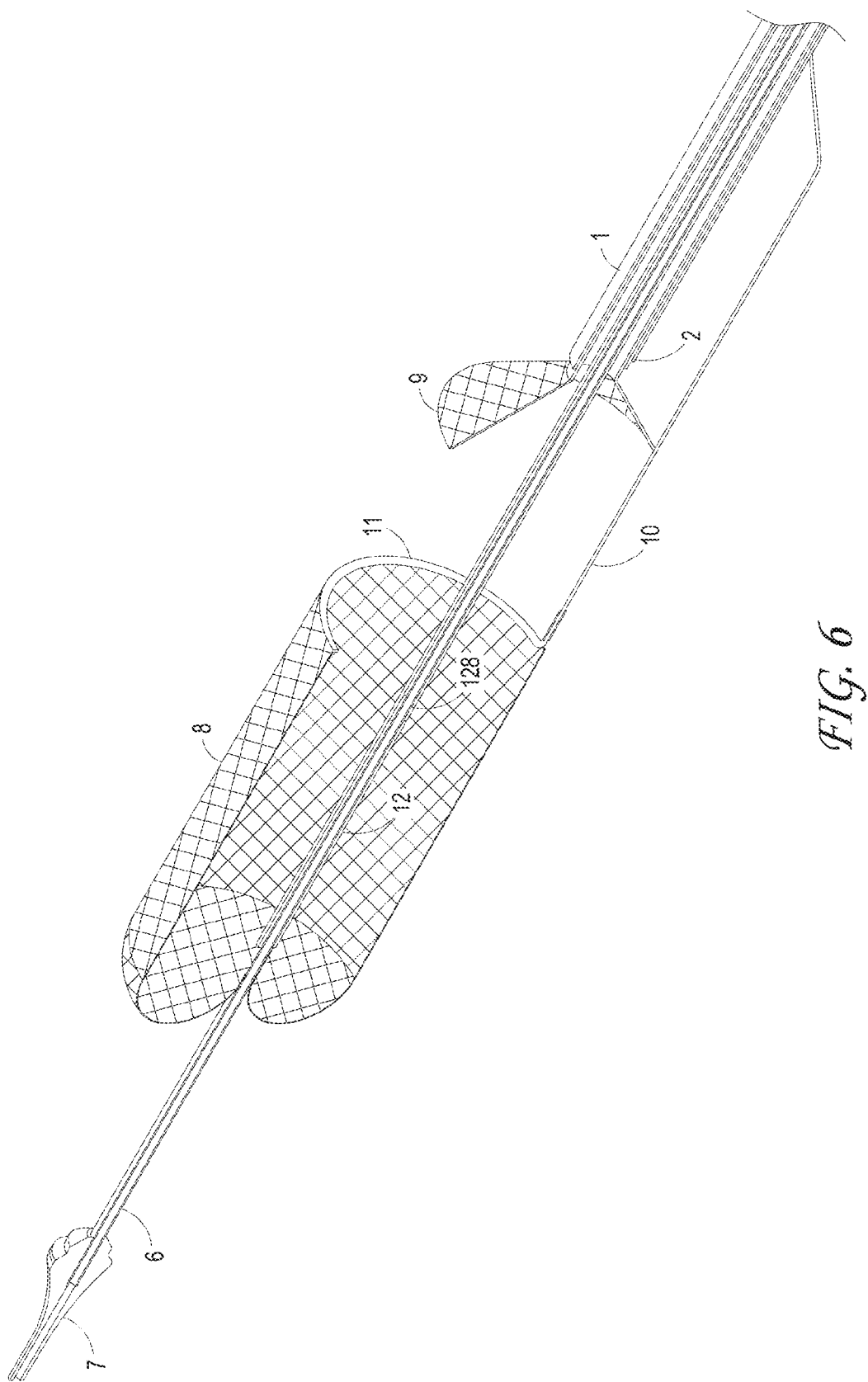
FIG. 6 illustrates the axial lengthen thrombus capture device retracting proximally to deploy and lengthen, according to some embodiments of the invention.

As shown, for example, in FIG. 6, it can also be possible to lengthen the ALTC Device 8 in an appropriate direction, such as distally, by pushing the capture catheter 12 relative to the guidewire shaft 6, thereby allowing additional reserve radially compressed length of the tubular mesh 8 to radially expand out of the confines of the lumen of the capture catheter 12 to axially lengthen the Thrombus Capture Device 8 and maintain its constant or substantially constant diameter through a working range. The other end of the ALTC device 8 at its radially compressed end can be fixed to the outer sidewall of the guidewire tube 6. A combination technique of, for example, manipulating the Capture Pull wire 10 attached to the Capture Catheter shaft 12 movement (FIG. 6) can position the ALTC device at a desired location within the body lumen, and movement of the guidewire catheter 6 axially with respect to the capture catheter shaft 12 will also axially lengthen or shorten the ALTC Device 8 while maintaining its diameter through a working range. When the ALTC Device 8 is in the deployed (expanded) configuration, the ALTC Device 8 can also be stretched beyond the working range to an extended axial length to reduce its diameter.

Figure 7:
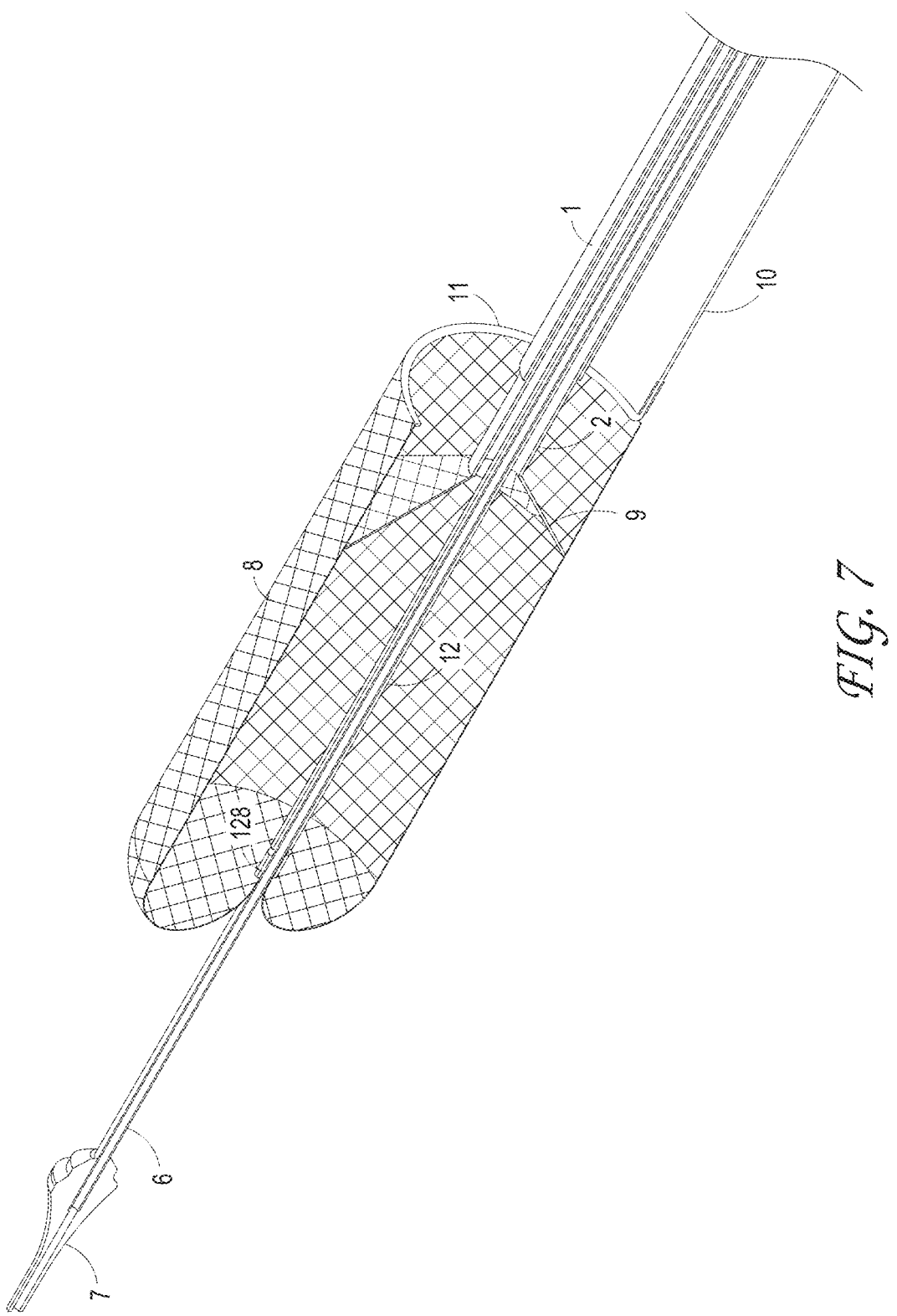
FIG. 7 illustrates the axial lengthen thrombus capture device is fully deployed and the funnel tip of the guide catheter is positioned within the ALTC device, according to some embodiments of the invention.

FIG. 7 illustrates the axial lengthening thrombus capture device 8 is fully deployed such that the attachment site 128 of the ALTC device 8 on the guidewire lumen 6 outer diameter is distal to the distal end of the capture catheter shaft 12 and the funnel tip 9 of the suction catheter is positioned within the ALTC, according to some embodiments of the invention.

Figure 8:
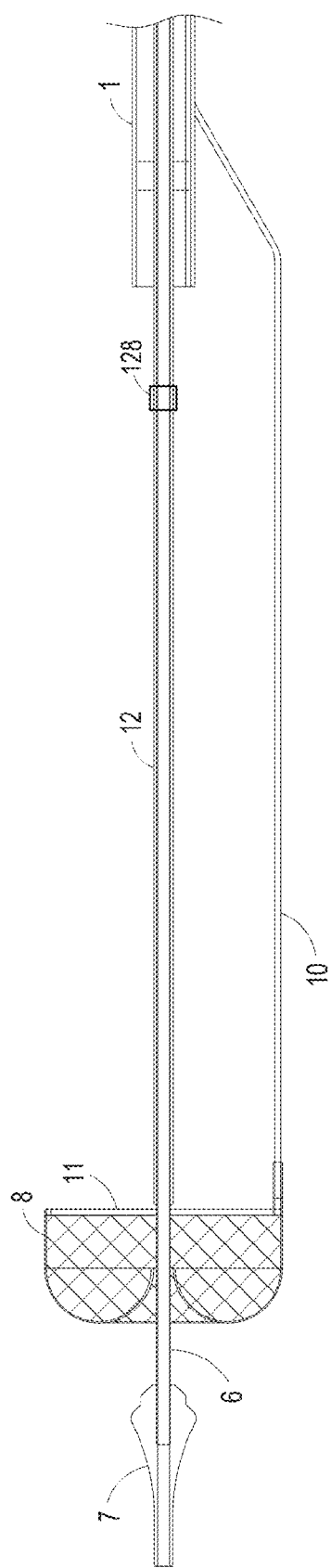
FIGS. 8 and 9 illustrate different views of the initial deployment position of the ALTC Device and the funnel tip of the suction catheter, according to some embodiments of the invention.
Figure 9:
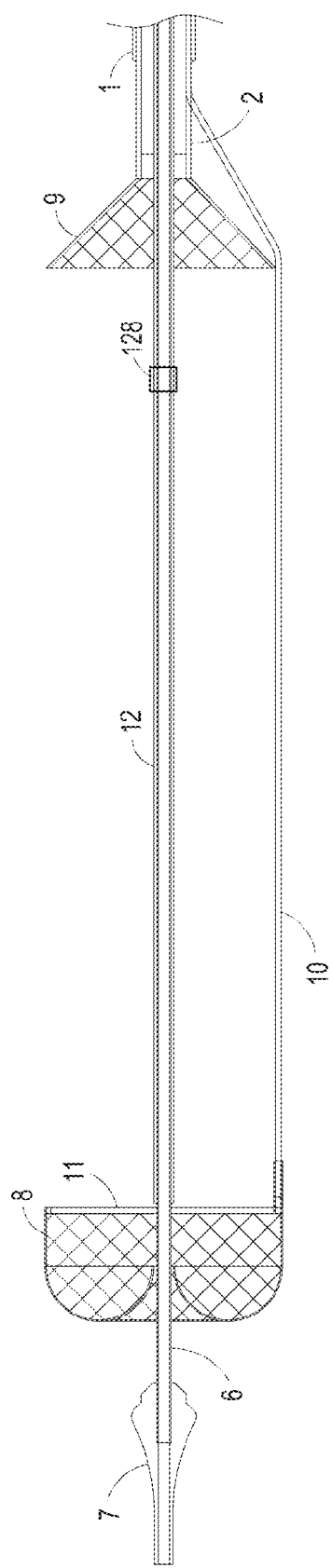

FIGS. 8 and 9 illustrate different views of the initial deployment position of the ALTC Device 8 and the funnel tip of the optional suction catheter 2, according to some embodiments of the invention.

Figure 10:
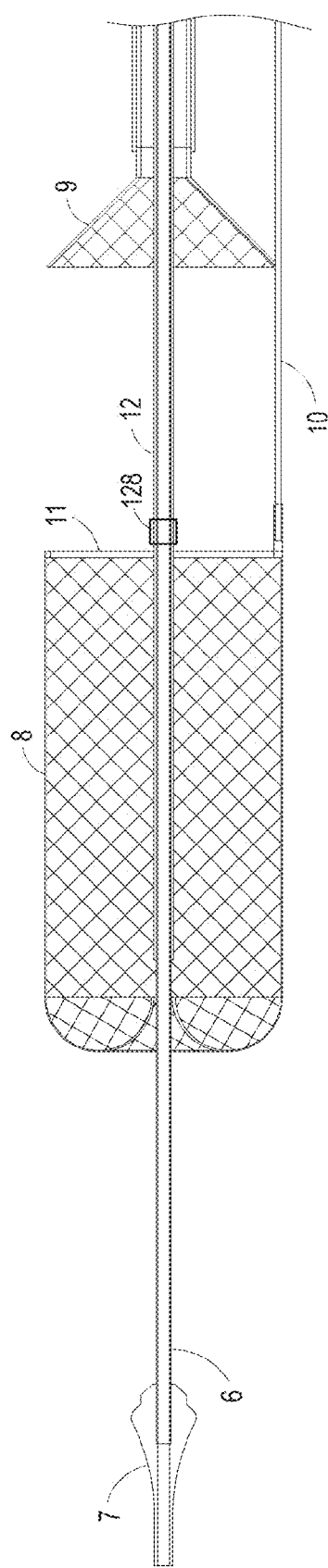
FIG. 10 illustrates the partially deployed ALTC Device, according to some embodiments of the invention.

FIG. 10 illustrates the partially deployed ALTC Device, according to some embodiments of the invention, where the ALTC device 8 is axially lengthened while maintaining its width normal to the axial direction.

Figure 11:
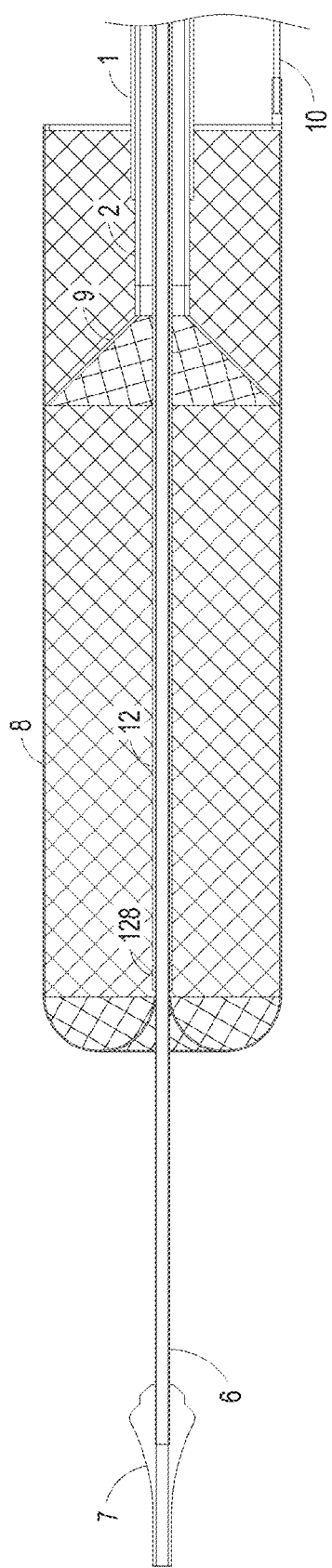
FIG. 11 illustrates an ALTC device deployed configuration where the funnel tip of the suction catheter is positioned inside the ALTC device, according to some embodiments of the invention.

FIG. 11 illustrates an ALTC device deployed configuration where the funnel tip of the suction catheter is positioned inside the ALTC device, according to some embodiments of the invention.

As illustrated, a Guidewire Lumen Assembly 6 can include a nose tip 7, shaft, lumen, and a proximal connector and port where a guidewire can be inserted therethrough. The central lumen can have a distal opening in some embodiments The guidewire tube 6 can be used to navigate and track over the guidewire in the vascular system. The guidewire tube 6 can extend coaxially within the lumen of the catheter shaft 12. A nose tip 7 can form or otherwise connect to the distal end of the guidewire tube 6 6 shaft to aid tracking the system through the vascular system, and can be atraumatic in some embodiments. The guidewire tube 6 can be made of polymeric materials such as, and not limited to Polyimide, Nylon, Polyurethane, Pebax, Polyethylene, PET, PTFE or ePTFE. The guidewire tube 6 can have, in some embodiments, radiopaque markers along its length for use to indicate the location of the ALTC Device, initial deployment, partial deployment, final deployment, the percent of length deployed and/or any combination thereof.

Figure 12:
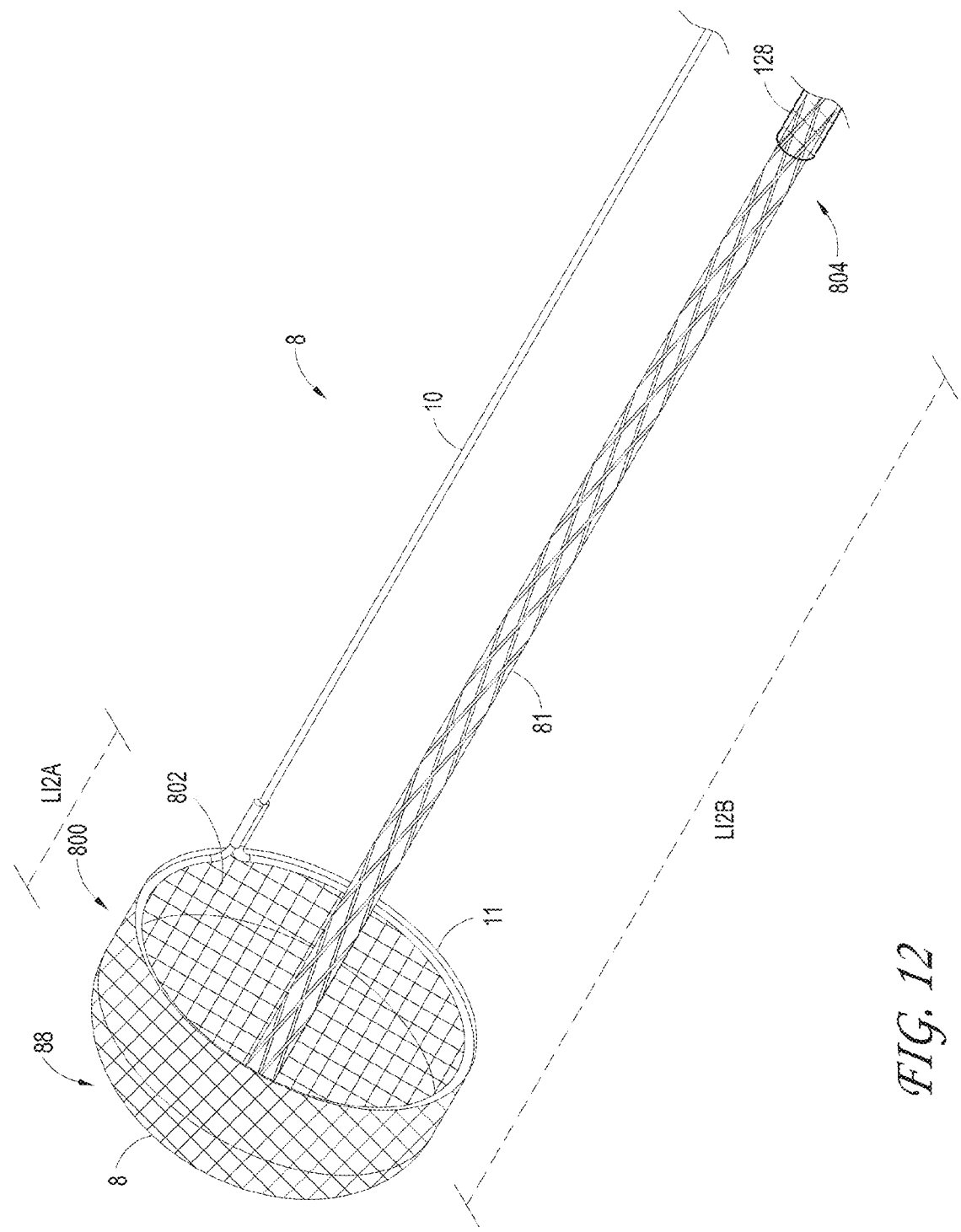
FIG. 12 illustrates the Axial Lengthening Thrombus Capture (ALTC) assembly wherein the distal end of the ALTC device is in the expanded (deployed) configuration and is fixed to the thrombus capture guide and capture pullwire, according to some embodiments of the invention. For purpose of illustration, the proximal end is in a collapsed configuration and extends proximally.

FIG. 12 illustrates the Axial Lengthening Thrombus Capture (ALTC) assembly 8 without the outer sheath, capture catheter 4, or guidewire catheter 6 present for clarity. As illustrated, end 800 with proximal-facing opening 802 of the ALTC device 8 is in the expanded (deployed) configuration and is fixed to the thrombus capture guide 11 and capture pullwire 10, according to some embodiments of the invention. For purpose of illustration, a reserve portion of unexpanded mesh 81 including end 804 is in a collapsed configuration and extends proximally toward attachment site 128.

In some embodiments, the tubular mesh structure 8 can axially lengthen or shorten without reducing or substantially reducing its diameter through a working length/axial range because the radially expanded portion of the tubular mesh structure is subject to none or minimal tension as it elongates or shortens axially through that axial working range. Not to be limited by theory, this can be accomplished at least in part because the tubular mesh structure can elongate axially throughout the working range by unrolling, everting, or otherwise expanding or transforming a radially compressed reserve segment of tubular mesh, such as unexpanded mesh 81. As such, an expanded "end" opposite the end of the radially expanded device with the capture guide and proximal end opening, such as dynamic fold point 88 of the radially expanded portion of the tubular mesh 8 may not be the absolute end of the tubular mesh fixed to a tubular shaft at zone 128, but rather an intermediate dynamic fold point 88 that is not fixed at that point to a tubular shaft, and as such not under any, or not substantially under any tension. The radially compressed reserve segment of tubular mesh 81 thus extends back in a different or the opposite direction (e.g., proximally in some cases) and ends at the terminal fixation point to the tubular shaft (e.g., at location 128). If it has not exceeded the working length of the expanded tubular shaft, the distance between the dynamic fold point 88 and the distal end of the entire catheter system (e.g., the nose tip) can increase as the radially expanded portion of the tubular mesh 8 lengthens, and the radially compressed reserve segment is used up.

Once the compressed reserve segment 81 of tubular mesh 8 is nearly or completely expanded to, or almost to its actual end at 128 and the tubular mesh 8 is axially elongated beyond its working length range, further axial elongation can start to exert significantly increased tension on the fully axially expanded tubular mesh structure 8, causing it to assume a configuration in which it radially contracts as it further axially lengthens.

A tubular net-like structure with one open end as disclosed above and elsewhere herein can be highly advantageous as a relatively small axial segment of the tubular mesh can be radially expanded and be fully functional to capture emboli and/or other materials in tight working environments, such as in obstructed body lumens with limited space to maneuver distal to the treatment location of interest. If it is desired that a greater axial length of radially expanded tubular mesh is required, such as to capture a relatively long length thromboemboli, the compressed reserve segment of tubular mesh can be unrolled, everted or otherwise expanded or transformed to a specific axial length as desired. Having a compressed reserve segment that can be stored along the length of the catheter system in a compact manner can be very advantageous in providing a long effective capture length tubular mesh without requiring the entire capture system to have a long fixed length as would be required in conventional filters/nets, which can be fixed at both ends and thus are functional and fully radially expanded when the first end is spaced apart from the second end at a single specific axial distance.

As illustrated in FIG. 12, some or most of the axial length of the ALTC device, e.g., the tubular mesh structure 8 remains radially compressed as part of the reserve segment between the outer diameter of the guidewire catheter 6 and the inner diameter of the shaft 12 of the capture catheter (distance between of which is length L12B), with the radially expanded portion of the tubular mesh structure 8 being defined along the axial length between proximal end 800 with proximal-facing opening 802 and the dynamic fold point 88 (distance between of which is length L12A), the sum of L12A and L12B amounting to the absolute length of the tubular mesh 8. In this initial configuration, the length L12B of the radially compressed reserve segment 81 can be about, or at least about 10%, 20%, 30%, 40%, 50%, 60%, 70%, 80%, 90%, or more of the absolute length of the tubular mesh 8.

Figure 13:
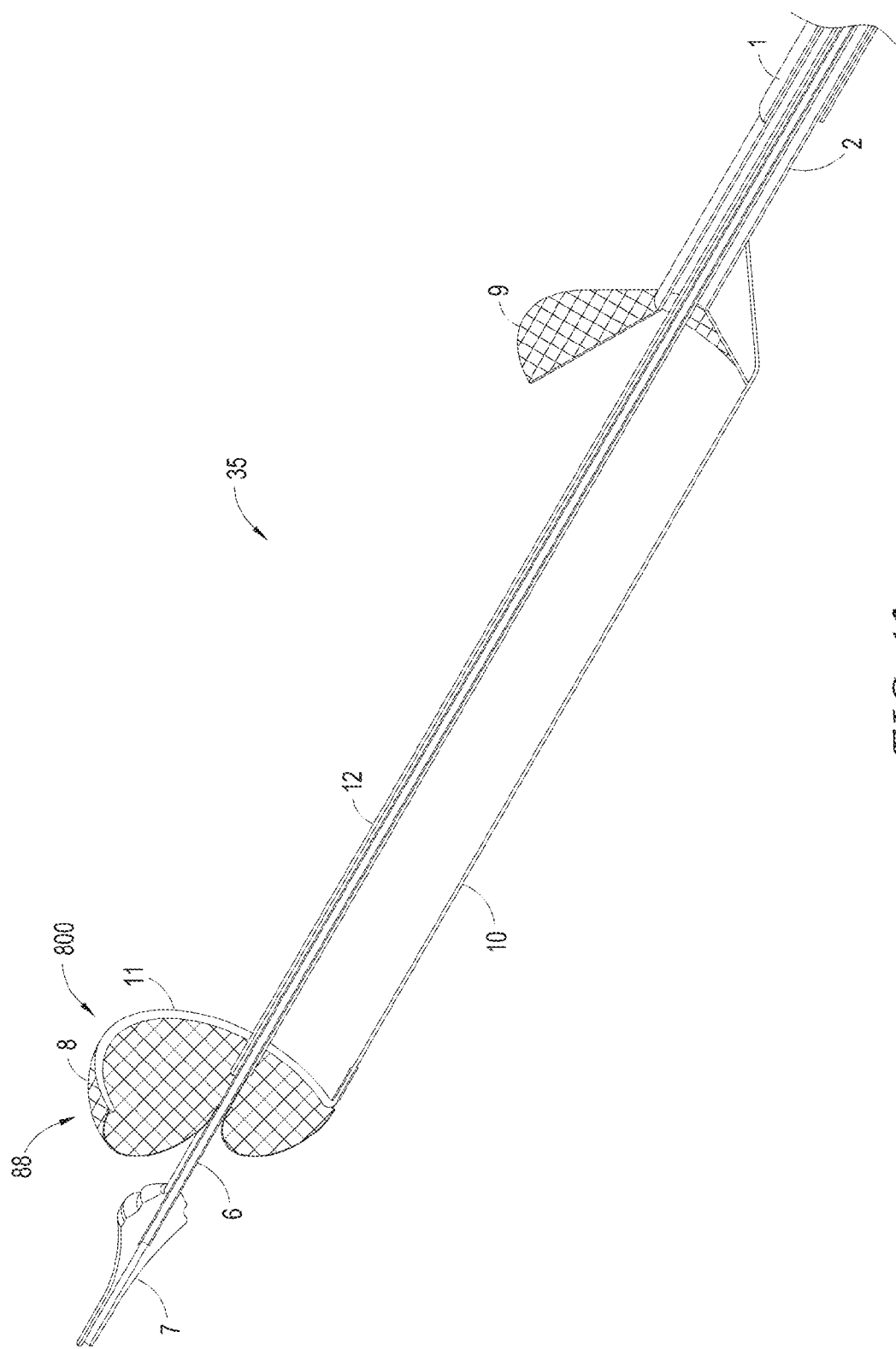
FIG. 13 illustrates the axial lengthening thrombus capture device in the initial deployed configuration, according to some embodiments of the invention.
Figure 14:
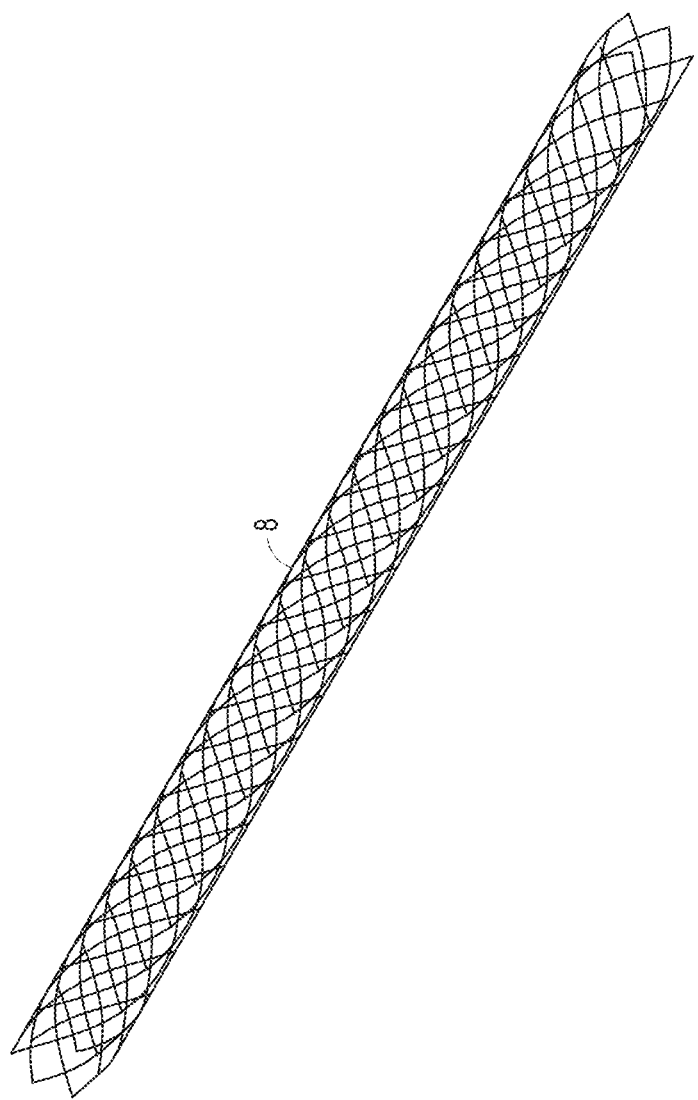
FIG. 14 illustrates the thrombus capture element of the ALTC device that can include a stent or braided mesh, according to some embodiments of the invention.

FIG. 13 illustrates the axial lengthening thrombus capture device 35 in the initial deployed configuration, according to some embodiments of the invention, with the radially expanded segment of the mesh 8 between end 800 and dynamic fold point 88 and the reserve compressed segment (not shown) extending axially proximally past end 800 to fixation point 128 on the outer surface of the guidewire shaft (not shown). FIG. 14 illustrates the thrombus capture element 15 of the ALTC device that can include a stent, braided, woven, laser cut, or other mesh such as a net-like structure, according to some embodiments of the invention. The tubular mesh structure need not necessarily be porous, and can be covered by nonporous or other layers. The ALTC Device tubular mesh structure 8 can be made of any suitable polymeric materials such as but not limited to polyethylene terephthalate (PET), polyethylene (PE) polypropylene (PP), nylon, silk, UHMWPE, PTFE, Kevlar, cotton, and/or metallic materials including superelastic material, nitinol, stainless steel, cobalt-chromium-nickel-molybdenum-iron alloy, or cobalt-chrome alloy, Chronichrome, or Elgiloy. The tubular structure can be braided, extruded, woven, knitted, laser cut, dip, film cast from a polymeric and/or metallic flat sheet, metallic filaments, polymeric filament or fabric in some embodiments. The tubular structure can be film cast with laser cut holes in some embodiments. The tubular structure can also be braided from polymeric and/or metallic filaments or any combination thereof. In some cases, the tubular structure can be made of nitinol wire mesh having multiple wire strands. Furthermore, the tubular structure can include at least one wire strand made of high radiopaque material such as tantalum, platinum, gold or nitinol drawn filler tube with a platinum core to enable viewing the tubular structure under fluoroscopy. In some embodiments, the tubular structure can include one, two, or more radiopaque markers. Depending of the diameter of the ALTC device, the number of wire strands can range from, for example, 1 to 576 wire strands. The ALTC Device can have 2, 4, 144, 288, or another number of wire strands in some embodiments. In some embodiment, the ALTC device is configured to have one wire strand. The wire strand diameter can range from, for example, 0.0002" up to 0.015". In some embodiments, the wire strand diameter is about 0.001". The tubular structure can be impermeable in some sections, permeable in other sections and/or a combination thereof. The tubular structure can be non-coated, or coated with one, two, or more anti-thrombogenic agents such as heparin to prevent clotting, or other therapeutic agents. The tubular structure can also be coated with a hydrophilic or hydrophobic agent. The tubular structure can have different pore sizes to assist with capturing small emboli or larger pore sizes to allow perfusion or blood flow. The tubular structure can have uniform pore sizes through the entire length or a combination of different pore sizes along its entire length. For example, when utilized as a cerebral protection filter, the ALTC device pore size can be sufficiently large to capture clinical relevant emboli size as small as, for example, about 200, 175, 150, 125, 100, 75, 50 microns or less while maintaining perfusion or blood flow. During retrieval, the ALTC device 8 can be repositioned to a particular section of the tubular structure that has smaller pore size and retrieve the blood clots/thrombus. In some embodiments, the ALTC device can deploy and enmesh within the blood clot to capture the blood clot in, for example, the neurovascular system. During retrieval, the ALTC device can lengthen sufficiently beyond the captured thrombus to create a protection filter distal to the captured thrombus. This can be clinically beneficial to prevent thrombus from dislodging during retrieval and thereby prevent secondary stroke. The ALTC Device tubular structure 8 proximal end can, in some embodiments, attach to the guidewire tube 6 outer surface, such as near attachment site 128. In some embodiments the proximal end of the ALTC Device tubular structure can be wrapped and sutured with polymeric filaments and encapsulated with low durometer polymeric material to fixably secure the wire ends to the shaft, such as the guidewire lumen assembly. Other means of attachment to secure the wire ends such as mechanically, thermally or chemically bonding the polymer to secure the wire ends can be used. In another embodiment, the ALTC Device proximal end can be fixed to the outer surface of the guidewire shaft using adhesive and is sandwiched between the outer surface of the guidewire shaft and cover tubes.

Figure 15A:
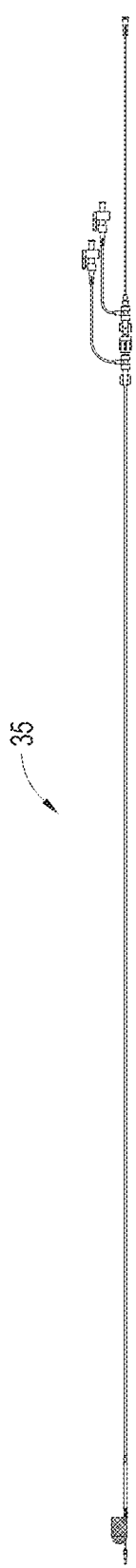
FIGS. 15A-C illustrate an embodiment of the ALTC system, a distal portion of the ALTC System and a proximal portion of the ALTC System respectively.
Figure 15B:
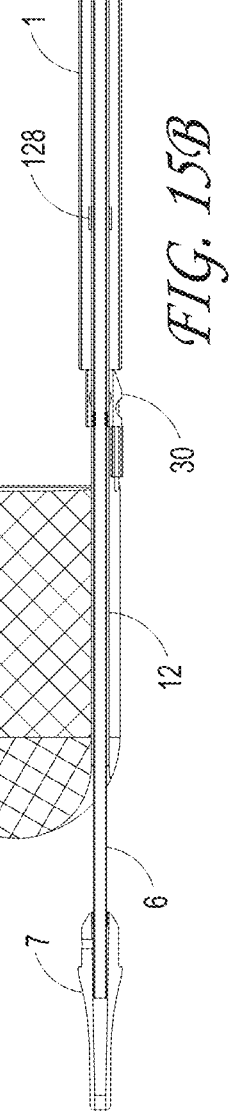
Figure 15C:
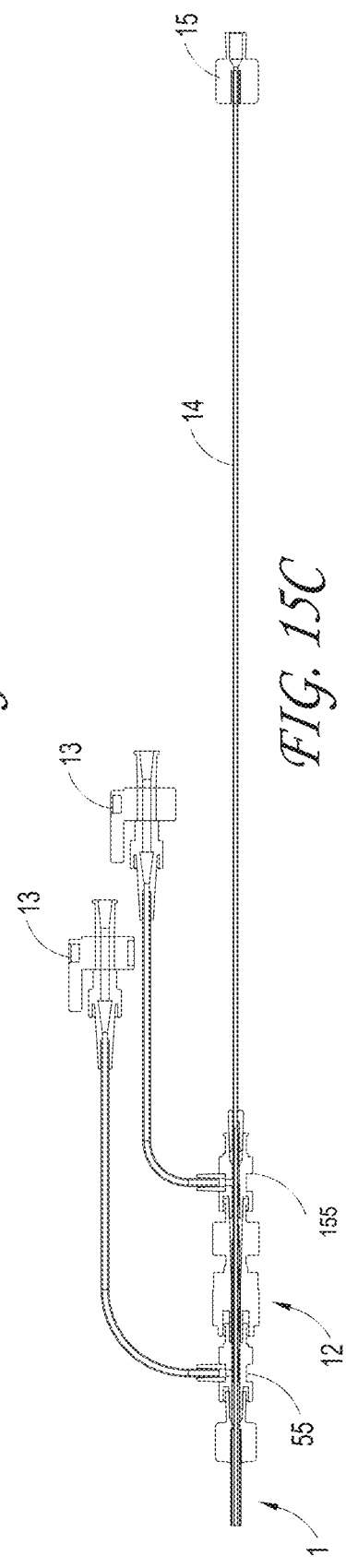

FIGS. 15A-C illustrate another embodiment of a clot capture system, a distal portion of the ALTC System and a proximal portion of the ALTC System respectively. FIG. 15A schematically illustrates the catheter system 35, while FIG. 15B shows the distal nose tip 7 operably connected to the distal end of the guidewire shaft 6 that includes a lumen for a guidewire to pass therethrough. One end of the ALTC device 8 can be fixably attached to the guidewire shaft 6 at one or more locations 128 and the other end 800 that includes proximal or distal-facing opening 802 is attached to capture guide 11, such as in the form of a loop 11, and it is movable axially distally and proximally via capture guide 11 Loop can include, for example, one, two, or more linear segments that extend proximally from the loop 11 onto the capture catheter shaft 12, which are in turn secured proximally to the capture catheter shaft 12 by a the sleeve 30. The sleeve 30 in some embodiments can be present instead of the pullwire(s) extending proximally all the way through the device. This can in some cases be advantageous ergonomically and allow for more streamlined control at the proximal end for a user. The axially expanded length of the tubular mesh 8 is shown extending from end 800 to dynamic fold point 88, with the reserve length of compressed tubular mesh (not shown) running proximally along the outer sidewall of the guidewire shaft 6 to its end at fixation point 128. FIG. 15C illustrates an embodiment of the proximal end of the system, including one or more flush ports 13, hub 55 of the outer sheath 1, hub 155 of the capture catheter 12, and hypotube pusher 14, and proximal-most hub 15 with a lumen configured to slide a guidewire therethrough. The hypotube pusher 14 can in some embodiments be coextensive with, such as welded or otherwise attached to the third tubular member (e.g., the guidewire tube 6), and when manipulated by an operator effect axial movement of the guidewire tube 6 in a proximal or distal direction. In some embodiments, there can be an integral guidewire tube 6 from the proximal most hub 15 to the distal nose tip 7. The third tubular member 14 can be configured to be placed within a lumen of a second tubular member (e.g., capture catheter shaft 12), such as at its proximal end at hub 155. The second tubular member can be configured to be placed within a lumen of a first tubular member (e.g., outer sheath 1), such as its proximal end at hub 55. In some embodiments, hub 55 and hub 155 can include complementary threads or other reversible locking features to allow for the outer sheath 1 to be reversibly coupled to the capture catheter 12 to allow for axial movement of the two tubular members in concert with each other. Uncoupling the hubs 55, 155 can allow for axial movement of the capture catheter 12 with respect to the outer sheath 1 and vice versa.

Still referring to FIGS. 15A-C, in some embodiments as illustrated, if a sleeve 30 is present, no separate pullwire extends from the capture guide 11 proximally to the proximal end of the system. In some such embodiments, axial movement of the capture catheter shaft 12 proximally with respect to the guidewire tube shaft 6 facilitates radial expansion of at least a portion of the ALTC device 8 and positioning of the ALTC device 8 within a body lumen. Axial lengthening and/or shortening of the ALTC device 8 in some embodiments can be effectuated by movement of the guidewire tube 6 (of which the other end of the ALTC device not attached to the capture catheter 12 via sleeve 30 is attached to, such as at attachment site 128) with respect to the capture catheter 12 and/or movement of the capture catheter 12 with respect to the guidewire tube 6.

FIG. 16A illustrates another embodiment of a distal portion of the axial lengthening thrombus capture device 35 in the delivery configuration, according to some embodiments of the invention.

FIG. 16B illustrates the axial lengthening thrombus capture device in the initial deployed configuration wherein the outer sheath 1 is retracted, e.g., proximally to radially expand an end that includes the proximal-facing opening 802 of the axial lengthen thrombus capture device (e.g., tubular mesh 8) to dynamic fold point 88 which serves as the effective expanded distal end of the tubular mesh 8. The capture guide 11 and associated terminal wires 10 are operably coupled to the sleeve 30, and the sleeve 30 is coupled to the outer wall of the capture catheter shaft 12, according to some embodiments of the invention. The compressed reserve length segment (not shown) of the tubular mesh, such as about or at least about 10%, 20%, 30%, 40%, 50%, 60%, 70%, 80%, 90% or more of the absolute axial length of the ALTC device 8 (e.g., tubular mesh) taking into account folds remains inverted, rolled up, and/or otherwise radially compressed and circumscribed by the inner sidewall of the capture catheter shaft 12, up to the point where the other end of the ALTC device 8 is attached on an outer diameter of the guidewire tube 6 at attachment site 128. As illustrated, the dynamic fold point 88 varies along the length of the tubular mesh 8 depending on the length of the compressed reserve length segment that is expanded. The dynamic fold point 88 "floats" and is not directly attached to the guidewire shaft 6 nor the capture catheter shaft 12, and as such moves axially proximally when the expanded segment of the tubular mesh 8 axially lengthens.

As such, when the guidewire shaft 6 with distal nose tip 7 is maintained in a constant position, axial elongation of the expanded tubular mesh 8 results in an increase in the axial distance D between the distal nose tip 7 and the dynamic fold point 88, so distance D3 is greater than D2, which is in turn greater than D1. Furthermore, as shown in FIG. 16B the first end 800 of the tubular mesh is distal to the unexpanded end of the tubular mesh (at location 128) fixed to the outer sidewall of the guidewire tube 6, but moves closer proximally in FIG. 16C and becomes proximal to the unexpanded end of the tubular mesh at FIG. 16D while the dynamic fold point 88 moves proximally but is still slightly distal to the unexpanded distal end of the tubular mesh 8 in FIG. 16D, where the expanded axial length is even greater, or in some cases at its maximum working length. As noted, the diameter/width of the expanded tubular mesh remains constant or relatively constant between FIGS. 16A-D. Upon exhaustion of the compressed reserve segment which has transformed into expanded tubular mesh, continued axial expansion can result in increased tensile forces on the tubular mesh, resulting in a configuration in which radial contraction begins to occur.

FIGS. 17A-D illustrate different configurations of the ALTC device, according to some embodiments of the invention. During delivery, the capture guide 11 (e.g., ring-shaped in some embodiments) connected to the expanded end 800 of the tubular mesh 8 can be configured to collapse within the outer sheath 1 lumen during introduction into the vascular system and is configured to radially expand first when the outer sheath 1 retracts proximally while the length of reserve tubular mesh structure 81 of the ALTC device 8 extending proximally from the dynamic fold point 88 to fixation point 128 on the guidewire shaft 6 remains compressed in the capture catheter shaft 12 lumen. The dynamic fold point 88 serves as the effective expanded distal end of the tubular mesh 8. Upon further retracting the thrombus capture guide 11 via pulling the Capture Pull Wire 10 (or sleeve 30 as shown) and capture catheter shaft 12 proximally, the portion of the ALTC Device 8 tubular structure that is compressed within the Capture Catheter Shaft 12 lumen expands and can transform via, e.g., roll out proximally, inversion, and/or eversion, and axially lengthening the ALTC Device 8. Advance of the Capture Catheter Shaft 12 distally can collapse at least a portion of the ALTC Device 8 tubular structure into the Capture Catheter Shaft 12 lumen, as previously shown in FIGS. 7-9. The ALTC Device's ability to expand, roll out, axially lengthen and maintaining a substantially constant diameter through a working range creates a cavity (or pocket) within the sidewall of the radially expanded segment of the ALTC Device 8 to retrieve and capture foreign materials such as, for example, blood clots/thrombus. In another embodiment a sleeve 30 (FIGS. 16A-D and 17A-D) can be used to couple, such as permanently, the Capture Pull Wire 10 to a portion of the Capture Catheter shaft 12 to enable both components to operate together. Coupling the Capture Pull Wire 10 and the Capture Catheter shaft 12 can allow the user to manage the capture device more efficiently and easily. In another embodiment, the capture guide 11 takes the form of a loop and can attach to the Sleeve 30, which is coupled to the Capture Catheter Shaft 12.

Figure 18A:
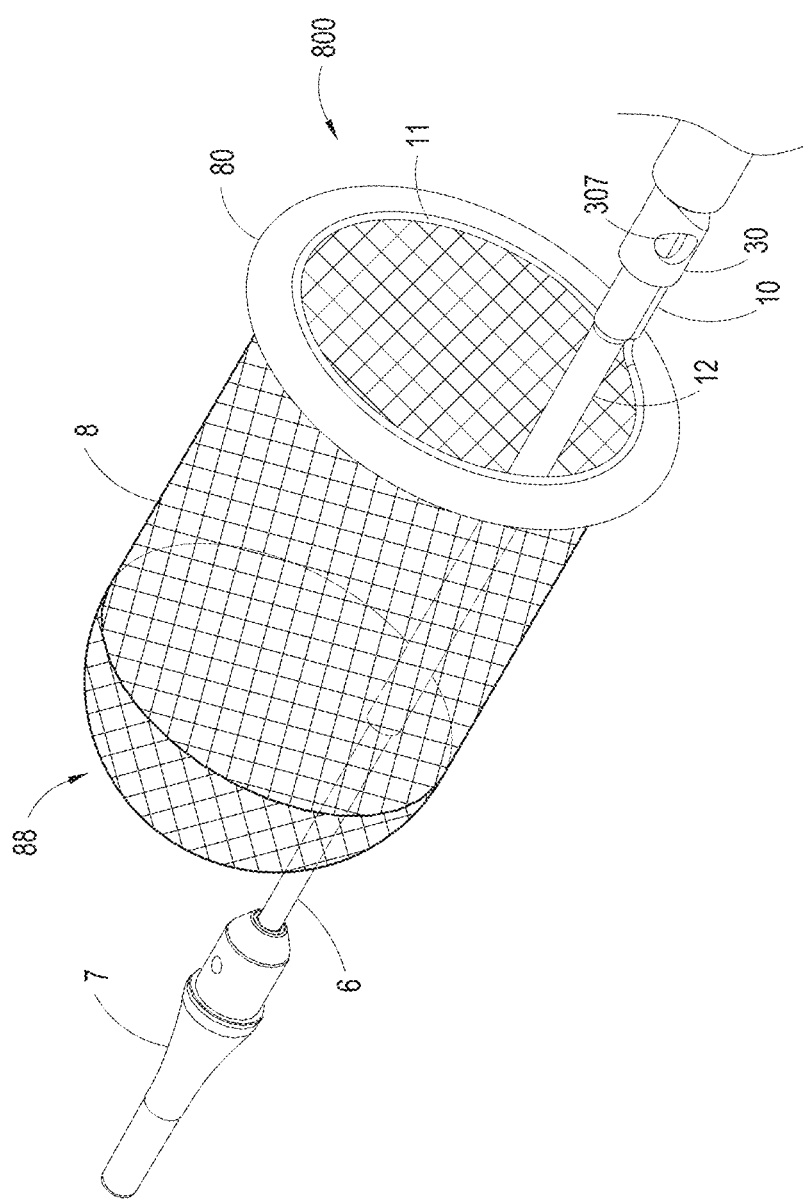

FIGS. 18A-B illustrate an embodiment of a distal portion of the axially-lengthening thrombus capture system with a cover element 80 radially outward of, and partially or completely circumscribing the capture catheter shaft 12 or loop 11 of the ALTC device, which can be in the shape of a ring as illustrated. In some embodiments, the cover element 80 can function to protect one or more of the capture guide, ALTC device, and the luminal wall of the lumen being treated. The ring 80 can also be configured to provide a seal against the luminal wall, e.g., of the vessel, to prevent leakage or migration or embolization of unwanted material around the tubular mesh 8. In some embodiments, the cover 80 can also include a skirt portion. The cover 80 can be axially and/or radially expandable, such as an inflatable balloon, a soft polymer, a gel, a foam, a textile fabric, shape memory, and/or include other materials. If the cover 80 is expandable, it can be configured to reversibly contract to allow for fluid flow around the cover 80 once the procedure is completed. Also as illustrated is sleeve 30 serving to attach the capture guide 11 connected to one or more wires 10. Sleeve 30 can include one or more apertures 307 that serve as relatively radiolucent markers, and/or the sleeve 30 could be made of a radiopaque material in some embodiments. Also as illustrated, the capture catheter 12 as well as guidewire tube 6 can extend through the tubular mesh 6 from first end 800 through dynamic fold point 88. The reserve segment of compressed tubular mesh is not shown for clarity.

Figure 19A:
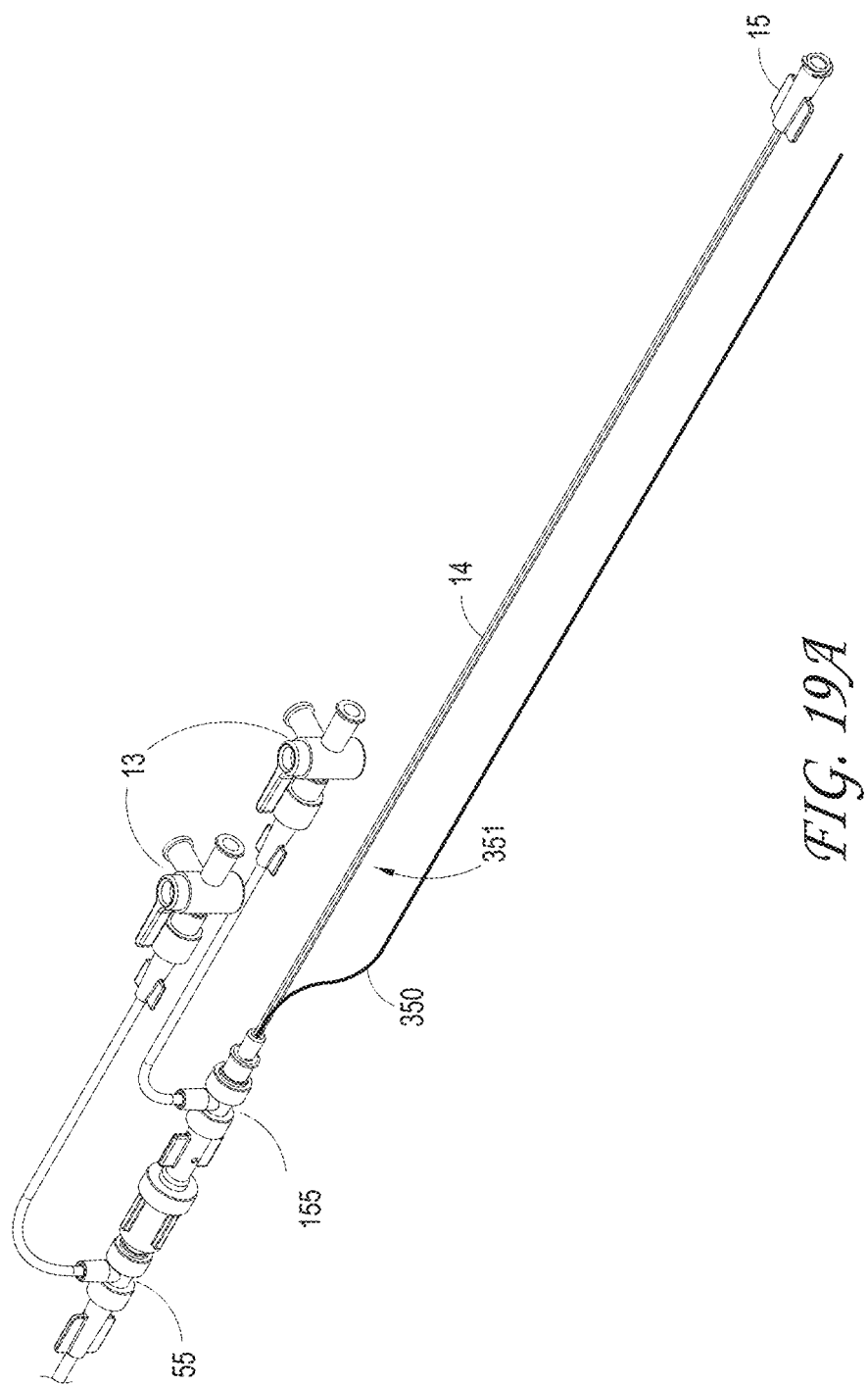
FIGS. 19A-C illustrates an embodiment of an axially-lengthening thrombus capture system, configured to allow the guidewire to distally exit the system prior to exiting the luer port at the proximal end of the system.
Figure 19B:
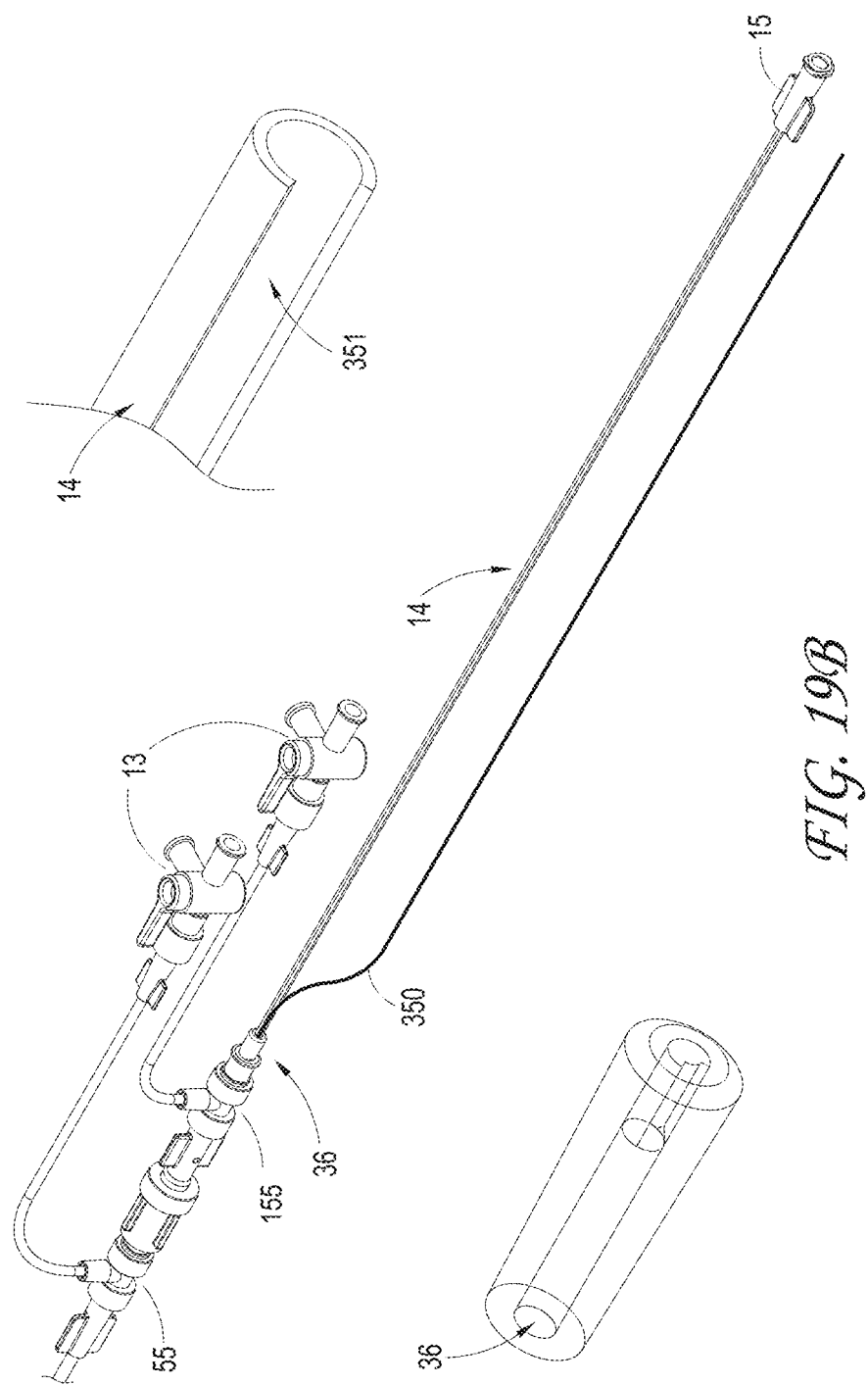
Figure 19C:
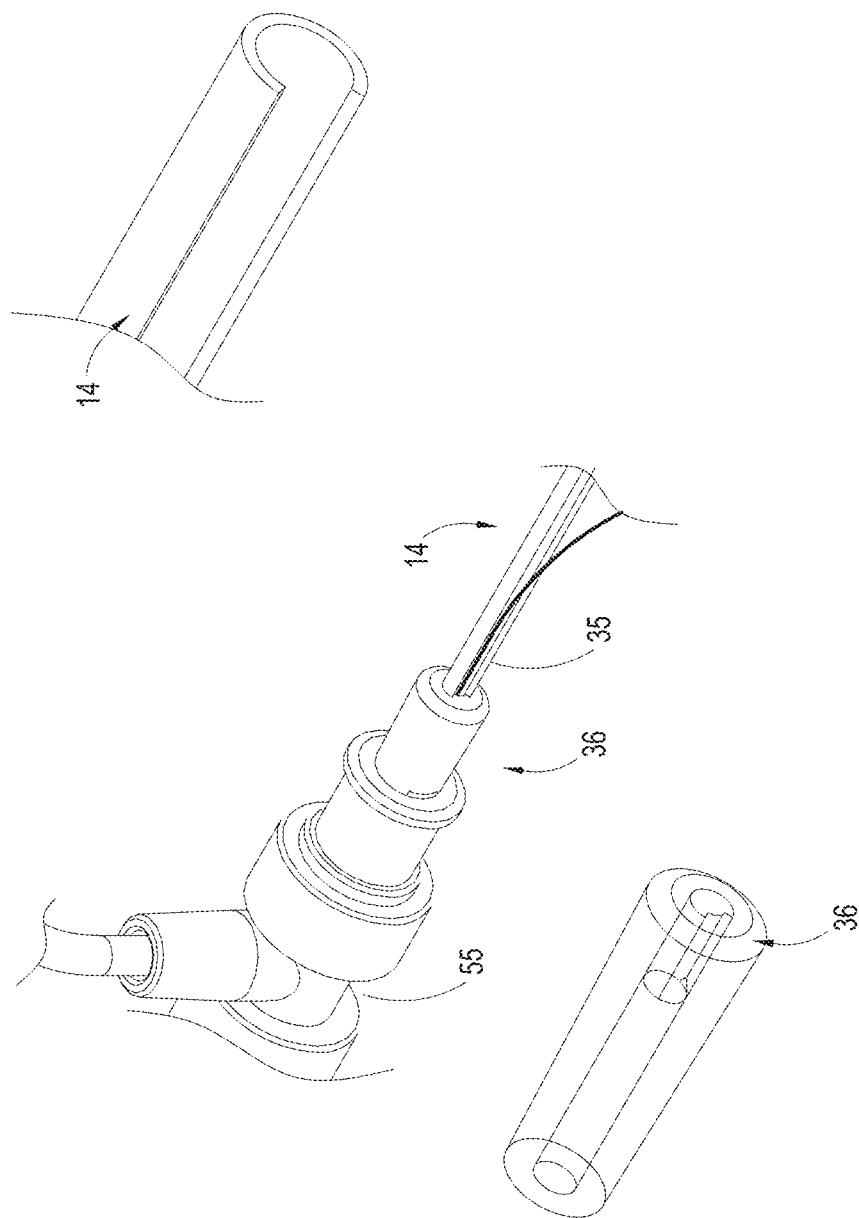

FIGS. 19A-C illustrate an embodiment of an axially-lengthening thrombus capture system, configured to allow the guidewire 350 to distally exit the system prior to exiting the luer/proximal-most port 15 at the proximal end of the system. The guidewire's proximal end can exit the system through an aperture or slot 351 in the sidewall once it passes the reversibly couplable hemostasis seals 55, 155 of the outer sheath 1 assembly and the capture catheter 12 respectively. In some embodiments, the guidewire 350 is configured to exit sideways, that is laterally. In some embodiments, a keyed cap 36 is positioned distal to the hemostasis seals 55, 155, which is in turn proximal to a shaft 14, which can serve as a hypotube pusher connected to or coextensive with the guidewire tube and be made of metal in some embodiments. The shaft 34 can include a sidewall groove 351 fully or partially axially from the port 15 to the hub 155 and/or one, two, or more discrete slots as illustrated.

Such embodiments can be advantageous, for example, to utilize a shorter length guidewire needed when the delivery system overall length increases. In some embodiments, when the ALTC capture device increase in length, the hypotube is also lengthened to accommodate thus increase the distance for user to manage the guidewire and system. The side guidewire feature can minimize the distance resulting in better handling, and the proximal end of the guidewire 350 need not necessarily extend past the proximal end of the entire system, such as at port 15. As such, the guidewire as part of the system can advantageously have a total length in some embodiments that is the same as, or even less than the axial length of the entire material capture system from proximal port 15 to distal nose tip 7, which may otherwise not be possible.

The guidewire 350 can be located near the hemostasis seals 55, 155 area during the procedure, and as such the entire procedure/operation can be done with the user not needing to look down to see where the components are located. As such, the user can hold the hemostasis seals 55, 155 housing in one hand while at the same time manipulating the guidewire 350 and hypotube pusher 14 with the other hand in the general area without substantially moving away from the area. The users can hold and maneuver the hypotube pusher 14 or hold and maneuver the guidewire 350 or hold both the hypotube pusher 14 and guidewire 350 at the same time. In some embodiments, the inner diameter of the shaft 14 with groove can be generally larger than the guidewire 350 that allows the guidewire 350 to exit laterally. The keyed cap 36 with a boss profile can mate to the groove of the metal shaft 14 to prevent the metal shaft 14 from rotating and still allow the shaft 34 to slide back and forth axially.

Figure 20A:
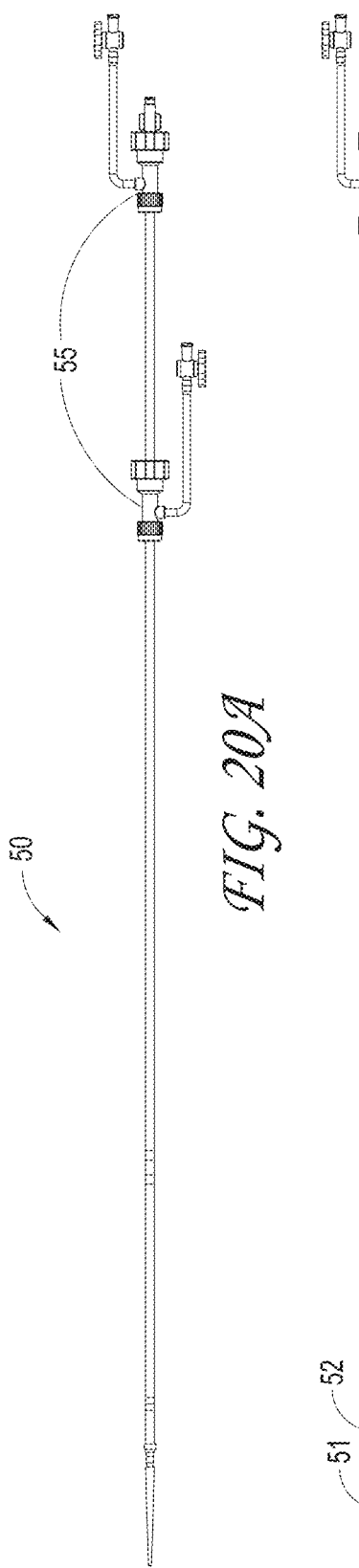
FIG. 20A illustrates the expanding guide catheter system in the delivery configuration, according to some embodiments of the invention.
Figure 20B:
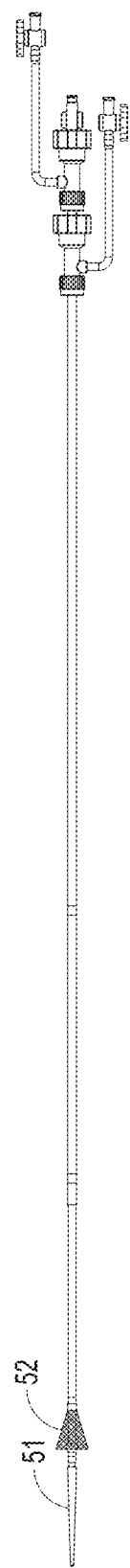
FIG. 20B illustrates the expanding guide catheter system wherein the funnel tip is in deployed position and the obturator is positioned in the expanding guide catheter lumen, according to some embodiments of the invention.
Figure 20C:
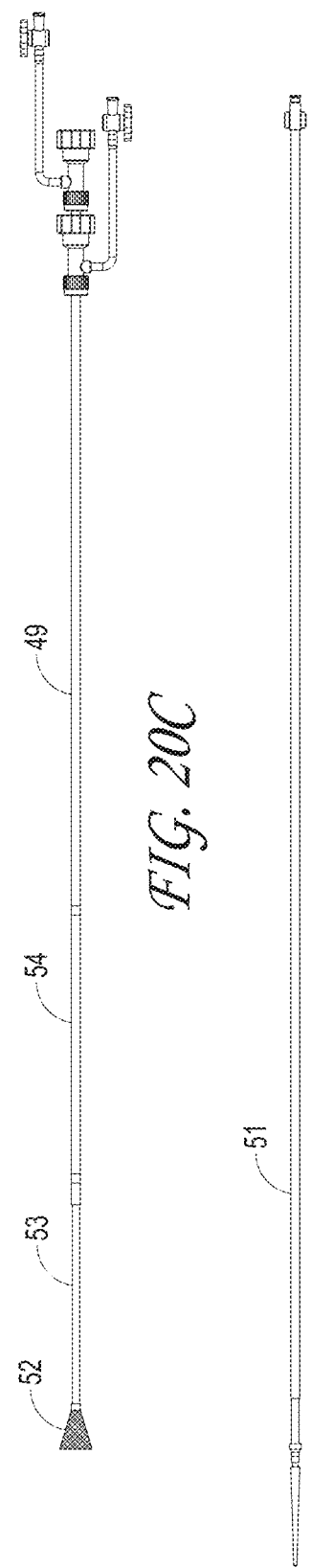
FIG. 20C illustrates the expanding guide catheter having a funnel tip, expanding distal segment and non-expanding proximal segment, according to some embodiments of the invention.
Figure 20D:
FIG. 20D illustrates an obturator, according to some embodiments of the invention.

In some embodiments, an Expanding Guide Catheter 50 (shown in FIGS. 20-21 for example) is a discrete catheter that can be utilized together with the clot capture system, and functions to assist in retrieving the ALTC Device 8 (and associated catheter system 35) and capture blood clots and other undesired materials. In some embodiments, the Expanding Guide Catheter 50 can include a first tubular member, such as an outer sheath 49 with a proximal end, a distal end, a lumen extending from the proximal end and the distal end, and a port on the proximal end, which can be coaxial as illustrated or offset from the longitudinal axis of the outer sheath 49. A second tubular member, such as inner catheter 54 can have a proximal end, a distal end, and a lumen extending from the proximal end to the distal end and can be configured to be placed within the lumen of the outer sheath 49. The inner catheter 54 can also have a proximal port, a removable obturator 51 positionable in the inner catheter lumen, distal expandable funnel tip 52, expandable shaft section 53 proximal to the funnel tip 52, an inner shaft 54, and connectors with seal 55. The obturator 51 can be used to aid in inserting and navigating the Expanding Guide Catheter 50 in the vascular system. The obturator 51 can be made of polymeric materials such as Polyethylene, Nylon, Pebax, Polyurethane, PET or PTFE for example. The obturator 51 can have a tapered distal end in some embodiments to aid in introducing the Expanding Guide Catheter 50 in the vasculature or other body lumen. Alternatively, other embodiments of the obturator 51 includes an expandable member such as a balloon operably connected to the distal end. Expansion of the expandable member, such as inflating the balloon can create a smooth tip transition. The balloon can be made of polymeric materials such Nylon, Polyurethane, PET, etc. Inflating the balloon can also secure the balloon obturator to the guide catheter such that when applying axial load proximally to the obturator shaft will articulate the tip of guiding catheter. The funnel tip 52, illustrated for example in FIGS. 20B-C, can include a distal funnel-like segment, and be adjacent to an expandable proximal segment 53 wherein it is connected to a more proximal portion of the inner shaft 54. The funnel tip 52 can be, in some embodiments, made of either polymeric and/or metallic materials. It can be either tubular in shape, woven or braided. The braid configurations can be, in some cases, 1×1 or 1×2 or 2×1 or 2×2 or any combination thereof. The picks per inch (PPI) can range from, in some embodiments, 5 to 60. The number can be, in some embodiments, from one wire filament up to 288 wire filaments. The wire shape can be, e.g., round, flat, oval, rectangular or square. The wire diameter can be, e.g., from 0.0005" up to 0.015". The flat wire thickness can be, e.g., from 0.0005" up to 0.010" and the wire width can be, e.g., from 0.001" up to 0.030". The funnel tip 52 distal segment can have various shapes or configurations to allow better retrieving the blood clots or thrombus. In some embodiments, the funnel tip 52 distal segment has a large open end where it contacts the vessel wall when expanded and transitions to smaller opening proximal segment 53. The distal segment open end can range from, in some embodiments, about 5 mm to about 80 mm in diameter. The funnel tip distal segment 52 also has, in some embodiments, openings or holes (perforations) along the side to allow blood flow. The funnel distal segment 52 can have either one layer of braid or multiple layers. In some embodiments, the funnel distal segment has two layers. In some one layer embodiments, the most distal open end of the funnel does not have the wire end terminate or exposed such that the wire ends are located at the proximal end of the funnel assembly. The funnel tip proximal segment 53 can be configured such that it is capable of expanding and receive the ALTC device and captured blood clots or thrombus. The proximal segment 53 can be configured to expand to receive object that is larger than its inner diameter and recovery after passage. The proximal segment 53 can include a PTFE inner layer and compliance and/or low durometer polymeric materials such as Polyurethane, Silicone, Tecoflex, Pebax 25D and/or 35D or braid and/or non-braided such as Pebax/Propel/BaSO4 outer layer. The proximal segment 53 can also include other lower durometer polymeric materials. The composite funnel tip and proximal segment can be laminated via dipped coat, spray or reflow process or any combination thereof. The braid materials can be either metallic and/or polymer and/or combination thereof. The braid configurations can be, e.g., 1×1 or 1×2 or 2×1 or 2×2 or any combination thereof. The picks per inch (PPI) can range from, for example, 5 to 60. The number can be, e.g., from one wire filament up to 288 wire filaments. The wire cross-sectional shape can be, for example, round, flat, oval, rectangular or square. The wire diameter can be, e.g., from 0.0005" up to 0.015". The flat wire thickness can be, e.g., from 0.0005" up to 0.010" and the wire width can be, e.g., from 0.001" up to 0.030". In some embodiments, an advantageous feature is the ability to expand and contract without buckling under compression. The inner diameter can range from, e.g., 2F to 30F. In some embodiments, the inner diameter can range from, e.g., 6F to 18F. The expanded length section can be up to the entire catheter length. In some embodiments, the length is about 20 cm. The funnel distal 52 and proximal segment 53 can also be made as one component wherein the braid configuration is continuous. Coupled to or continuous with the funnel tip proximal segment 53, the inner shaft 54 can be made from materials such as and not limited to Nylon, Polyurethane, Pebax, Polyethylene, PET, PTFE, or ePTFE. The inner shaft 54 can be braided or non-braided. The outer shaft 49 can function to slide over and collapses the funnel tip and provide support during introduction into the vasculature. The outer shaft 49 retracts to deploy the funnel tip. The outer shaft 49 can be made of polymeric materials such as Nylon, Polyurethane, Pebax, Polyethylene, PET, PTFE, ePTFE, FEP or combination thereof. The outer shaft 49 diameter can range from, e.g., 4F to 34F. The outer shaft 49 inner diameter can range from, for example, 3F to 32F. In some embodiments, the inner diameter has substantially the same throughout the lumen shaft. In some embodiments, the inner diameter at the distal end is larger than the proximal end inner diameter. The change in inner diameter can be in one location, two or more locations. The outer diameter is substantially the same throughout the entire length of the outer sheath shaft. In some embodiments, the outer shaft 49 is about 22F or smaller in diameter. The outer shaft 49 can include a radiopaque marker at the distal end or radiopaque filler along its shaft length for visibility under fluoroscopy. In some embodiment, the outer shaft can be deflectable (via, for example, one, two, or more pullwires on the distal end) at various locations and multiple deflectable directions along the shaft length to accommodate various tortuous paths such as entry into the right atrium, right ventricle, main pulmonary artery, and left and right pulmonary artery for pulmonary embolism applications.

Still referring to FIGS. 20A-20D, in some embodiments the expanding guide catheter 50 can be utilized to retrieve blood clots or thrombus. The expanding guide catheter 50 and obturator 51 can be introduced over a wire into the vasculature and advanced near the treatment area. The obturator 51 is removed. The outer member 49 of the expanding guide catheter is retracted proximally to expand the funnel tip 52 and the expandable section 53 of the guide catheter 50. In some embodiments, the guide outer shaft 49 is inserted into the vessel together with the obturator 51 and the obturator 51 is removed once the outer shaft 49 is in a desired position. The inner guide member can include the funnel tip 52, proximal segment 53 and the inner shaft 54 is then inserted into the outer shaft 49 up to the distal tip of the outer shaft 49. The outer shaft 49 can then be retracted (or the inner shaft 54 advanced) to expand and deploy the distal funnel 52 and the proximal segment 53. The capture catheter system 35 is inserted over the wire and through the lumen of the expanding inner guide member 54. Once the ALTC Device 8 is deployed and captures the blood clots, the ALTC Device 8 is retracted along with the captured blood clots into the funnel tip 52 and expanding guide inner member 53, (shown later in FIG. 50). When high resistance is encountered at the funnel tip due to the large blood clot position at the tip, the guidewire lumen can advances distally to lengthen the ALTC Device. Lengthening the ALTC device can create additional space within the ALTC device such that the blood clot volume is redistributed thereby reduces the large blood clots pooled at the tip of expanding guide catheter. The expanding guide catheter distal section also allows larger clots to be captured due to its expandability increasing the lumen size. Continuing to retract the ALTC device will retrieve additional captured blood clots inside the expanding guide catheter. Repeated lengthening of the ALTC during the procedure will continue to redistribute the clot and retrieve inside the Expanding Guide Catheter, advantageously allowing for improved thrombus processing and redistribution. In some embodiments, a kit can include a capture catheter system 35 as described herein and configured to be reversibly placed within, and move axially with respect to an inner lumen of a discrete expanding guide catheter system 50 as described herein.

Figure 21A:
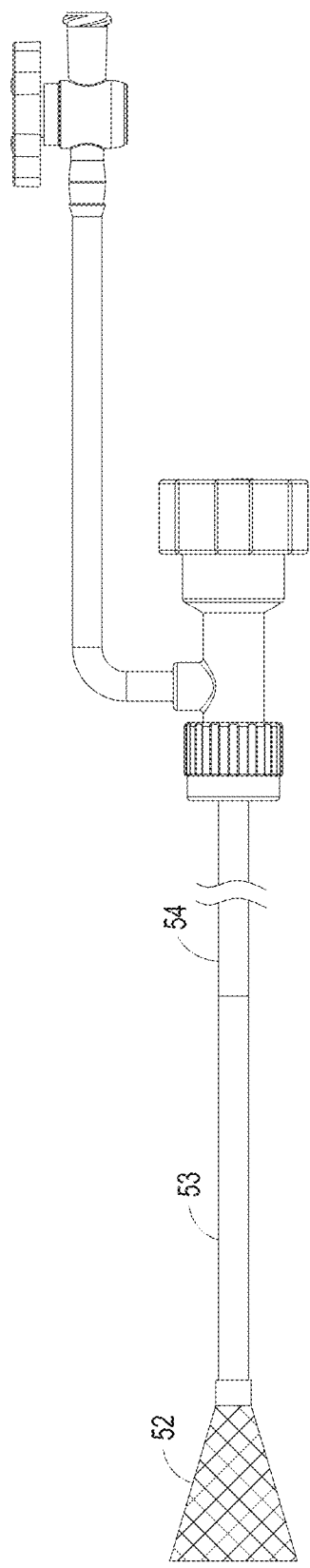
FIGS. 21A-C illustrate the expanding guide catheter system including the expanding guide catheter, outer cover and obturator, according to some embodiments of the invention.
Figure 21B:
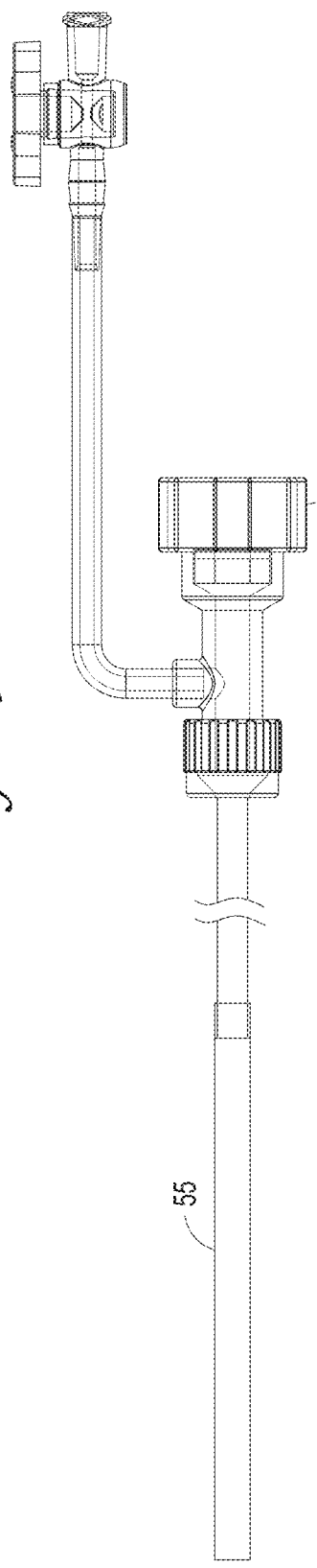
Figure 21C:
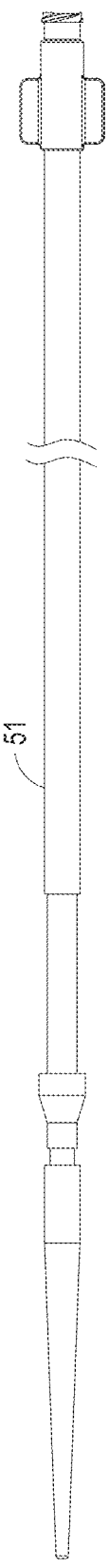
Figure 21D:
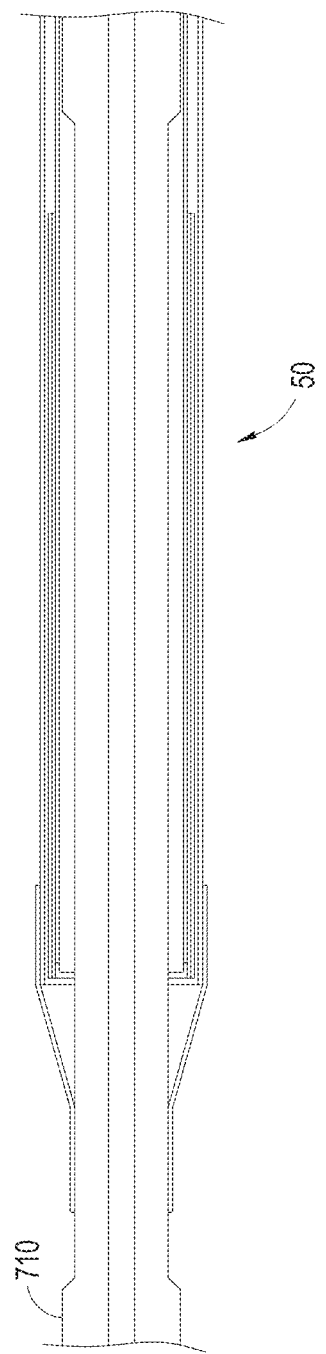
FIG. 21D illustrates an embodiment wherein a cover tip encapsulates the distal end of the outer cover of the expanding guide catheter system, according to some embodiments of the invention.
Figure 21E:
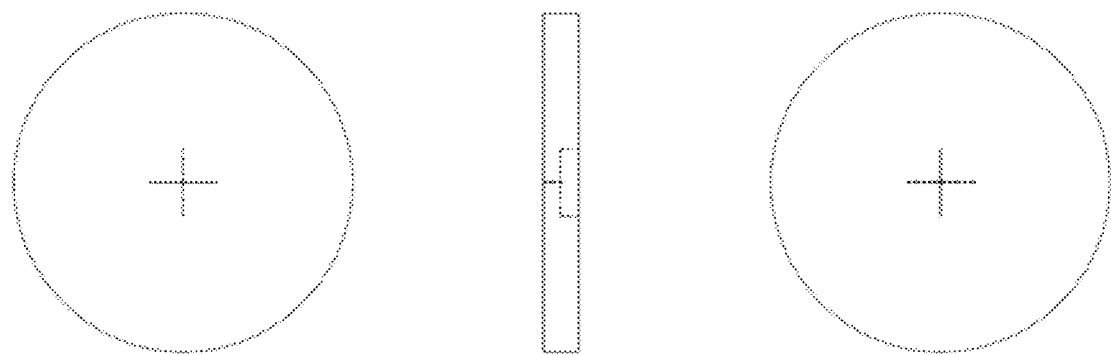
FIGS. 21E-F illustrate an embodiment of a hemostasis valve for use within a hemostasis guide catheter system.
Figure 21F:
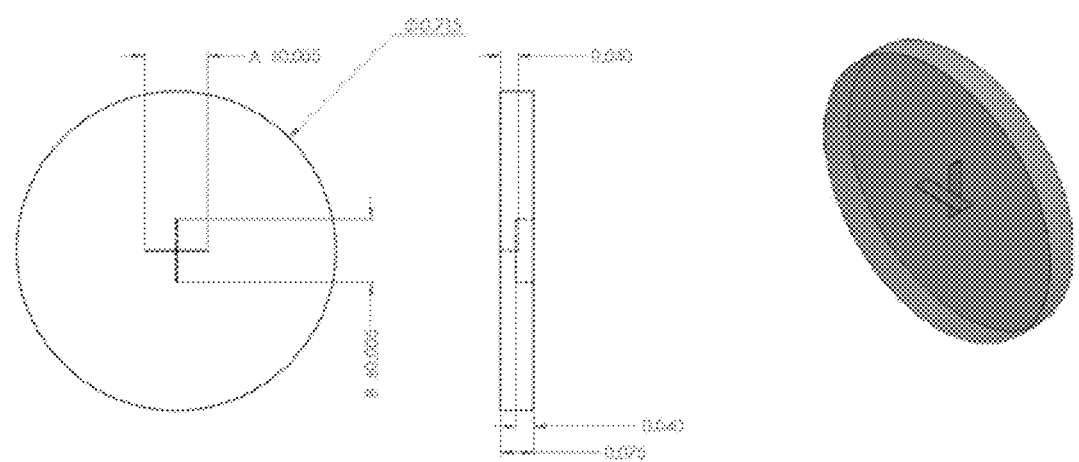

FIG. 21D illustrates an embodiment wherein a cover tip 710 encapsulates the distal end of the outer cover of the expanding guide catheter system, according to some embodiments of the invention. In some embodiments, a guide catheter is part of a hemostasis guide system that can includes one or more obturators, an inner shaft member, an outer shaft member, and a hemostasis valve disposed within a housing of the system. The inner shaft member can include a non-expandable braided proximal segment, a distal expandable segment and a braided funnel distal end which can be as described elsewhere herein. The inner shaft member can be positioned within the lumen of the outer shaft member. The outer shaft member can have, for example, a braided polymeric configuration with a flexible kink resistance distal segment. The inner shaft and outer shaft member can be attached to the housing body. The housing body can be, for example, at a proximal end of the guide catheter system. The hemostasis valve can be disposed within the housing body. The hemostasis valve can be in some embodiments a flexible disc-like valve. The hemostasis valve can be configured to provide hemostasis and prevent leakage, such as with nothing inside. In some embodiments, the system can be configured for use with a 0.035" guidewire, 5Fr catheter, and include sizes between about 12F and about 17F, such as about 12F, 16F, or 17F. The hemostasis valve can include two surfaces, an upper surface and a lower surface. The upper surface and lower surface can be opposing surfaces in some embodiments. The upper surface can include a slit extending partially across the upper surface and a depth into the valve without protruding all the way through the thickness of the lower surface. The lower surface can include a slit extending across the lower surface and a depth into the valve without protruding all the way through the thickness of the upper surface. In some embodiments, the valve has a diameter of between about 0.50" and about 1.00", such as about 0.5", 0.6", 0.7", 0.8", 0.9", or 1.0". In some embodiments, the valve has a thickness of between about 0.050" and about 0.0100", such as about 0.075". In some embodiments, the slits can have a depth/thickness of between about 0.020" and about 0.060", such as about 0.040". The midpoint of a slit can be in some cases at or proximate the center of the surface of the disc. The upper slit and the lower slits can intersect at, for example, a point location within the valve. The slits can extend beyond the intersection point by a desired distance, such as between about 0.001" and about 0.010" or approximately 0.005" beyond the intersection point. In some embodiments, the arrangement of the slits along the valve permits insertion and removal of shafts therethrough while preventing leakage of blood or air back across the valve. The upper and lower slits can have long axes that intersect at an angle. The angle could be in some embodiments between about 45 degrees and about 135 degrees, or about 45, 60, 75, or 90 degrees in some cases.

Figure 22:
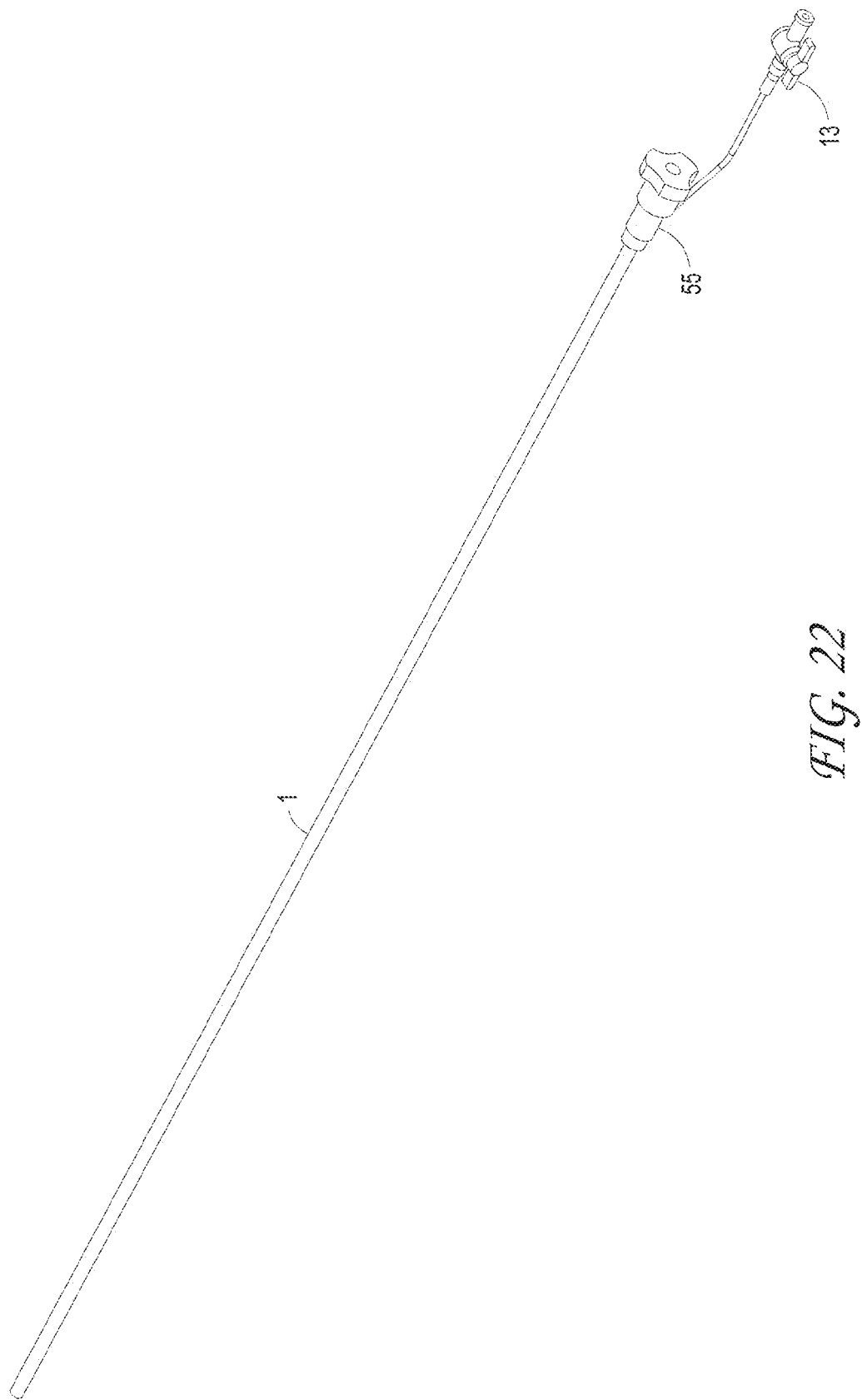
FIG. 22 illustrates the outer sheath assembly of the capture device, according to some embodiments of the invention.
Figure 23:
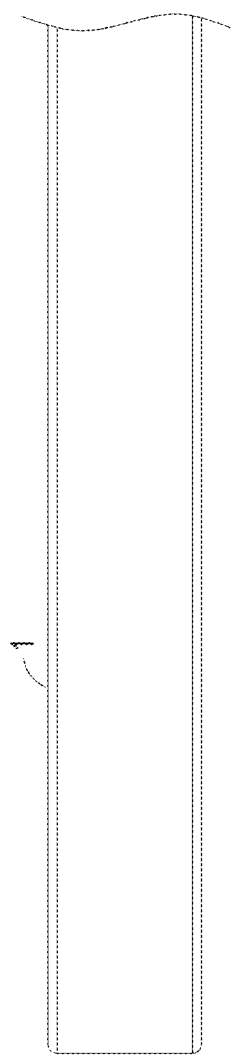
FIGS. 23 and 24 illustrate the distal end and proximal end of the outer sheath assembly respectively.
Figure 24:
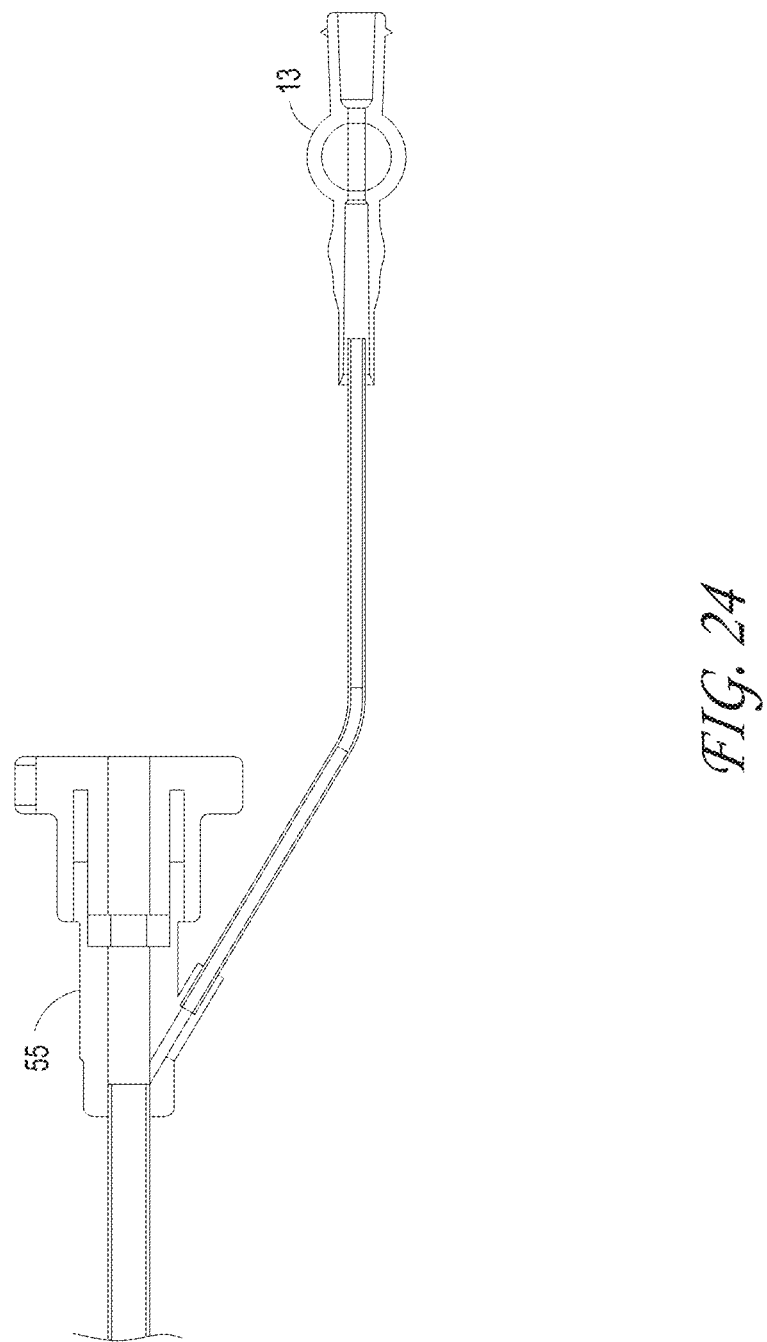
Figure 26:
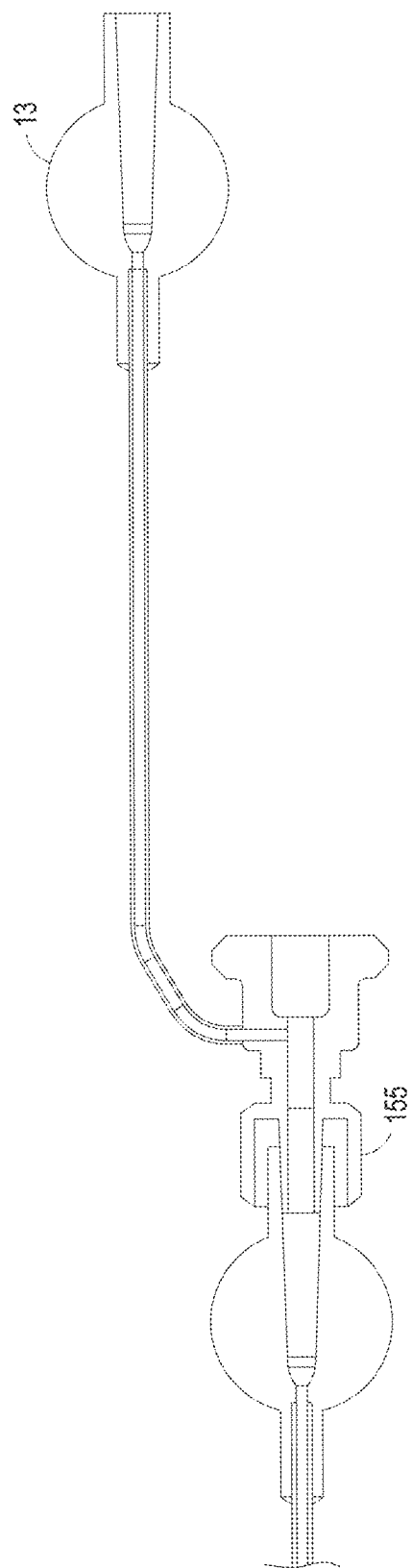
FIG. 26 illustrates the proximal end of the capture catheter, according to some embodiments of the invention.

FIGS. 22-24 illustrate the outer sheath assembly 1 of the capture device, according to some embodiments of the invention. The outer sheath 1 can function to contain, protect, and deliver the Axial Lengthening Thrombus Capture Device (tubular mesh 8 (not shown) to the desired anatomical location, such as in a radially compressed configuration. As shown in FIG. 22, the Outer Sheath 1 can include a soft atraumatic distal tip, a shaft body that can be tubular in some embodiments, an interior channel/lumen configured to house and reversibly couple at its proximal end a second tubular member, such as a capture catheter as described elsewhere herein, and a proximal connector with a seal 55 and flush tube/port 13. The Outer Sheath 1 can be made from suitable medical grade materials, including but not limited to Nylon, Polyurethane, Pebax, Polyethylene, PET, PTFE, ePTFE, PEEK, PEBAX/Propell and polypropylene. The polymeric materials can include radiopaque materials such as, for example, barium sulfate, bismuth subcarbonate or bismuth trioxide to enable viewing under fluoroscopy. The radiopaque materials can form one, two, or more discrete marker elements in some embodiments, such as at the distal tip, and/or spaced apart at regular or irregular intervals along the length of the outer sheath 1. The outer diameter of the outer sheath 1 can range from, for example, 3F to 30F. The inner diameter of the outer sheath 1 can range from, for example, 2F to 28F. In some embodiments, the inner diameter is substantially constant throughout the interior channel, e.g., the lumen shaft. In some embodiments, the inner diameter at the distal end is about or at least about 10%, 20%, 30%, 40%, 50%, or more than the proximal end. The change in inner diameter can be, for example, stepwise or gradual in one location or two or more locations. The outer diameter can be substantially the same the entire length of the catheter, in some embodiments. The outer sheath 1 working length can be, in some cases, from about 10 cm to about 150 cm. In some embodiment, the Outer Sheath 1 working length is about 135 cm in some embodiments. The Outer Sheath 1 shaft can be braided or non-braided. In some embodiments, the Outer Sheath 1 shaft can be deflectable (via, for example, one, two, or more pullwires on the distal end) at various locations and multiple deflectable directions along the shaft length to accommodate various tortuous paths such as entry into a left or right heart atrium, heart ventricle, main pulmonary artery, and left and right pulmonary artery for pulmonary embolism applications, or a vein such as the great saphenous vein, superficial femoral, common femoral, SVC, IVC, or other upper or lower extremity, visceral, or other superficial or deep veins for deep venous thrombosis removal applications. The distal end of the shaft of the outer sheath 1 can be configured to deflect up to 360 degrees in some cases. Additionally, the distal tip of the Outer Sheath 1 can be configured to deflect or bias toward or away from the vessel wall. The distal tip of the outer sheath 1 can include one, two, or more radiopaque markers to indicate tip location. Alternatively, the distal tip can include radiopaque materials such as, for example, Barium Sulfate, Bismuth Subcarbonate or Bismuth Trioxide. FIGS. 23 and 24 illustrate the distal end and proximal end of the outer sheath assembly respectively. As shown in FIG. 26, the proximal end of the outer sheath 1 connects to the outer sheath connector 55 with seal and coupler to a capture catheter connector, and flush port 13.

Figure 25:
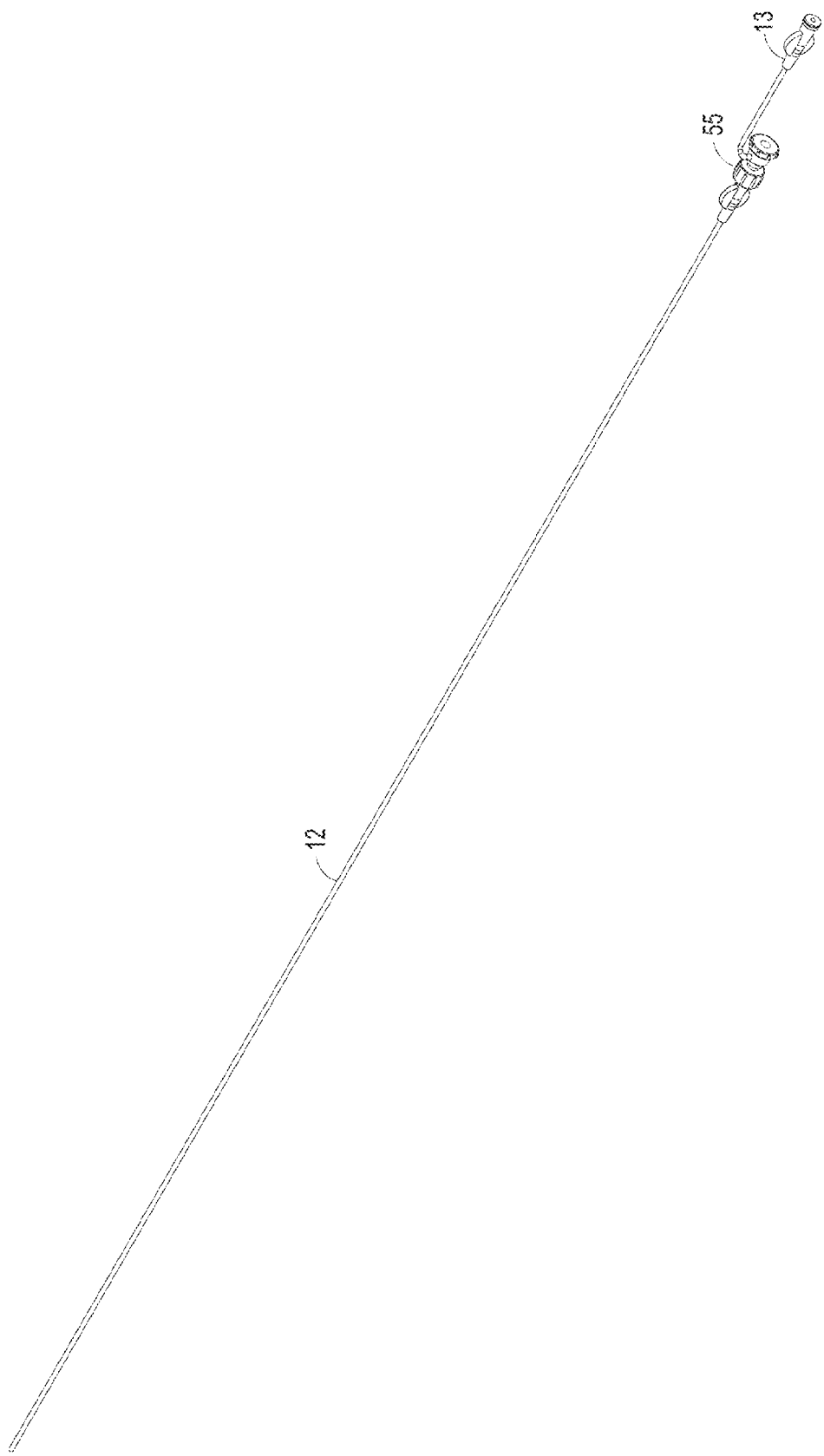
FIG. 25 illustrates the capture catheter assembly, according to some embodiments of the invention.

FIG. 25 illustrates the capture catheter assembly 12, according to some embodiments of the invention, showing catheter shaft 12 and outer sheath 1. FIG. 26 illustrates the proximal end of the capture catheter, according to some embodiments of the invention, showing a connector with seal 155 operably connected to a flush port 13.

FIG. 27 illustrates an embodiment of a key cap 36 feature to prevent or inhibit rotation of the hypotube pusher 14. As illustrated, the key cap 36 can be a tubular member with a lumen to fit the hypotube pusher 14 therethrough. The lumen is non-circular in some embodiments, and/or have a non-circular zone, or otherwise configured to prevent or limit rotation. In some embodiments, the lumen includes teeth or other projections into the lumen as shown to prevent undesired rotation of the hypotube pusher. In some embodiments, the lumen or a portion thereof has a square, rectangular, triangular, oval, pentagonal, hexagonal, or other non-circular geometry, and configured to limit rotation.

Figure 28:
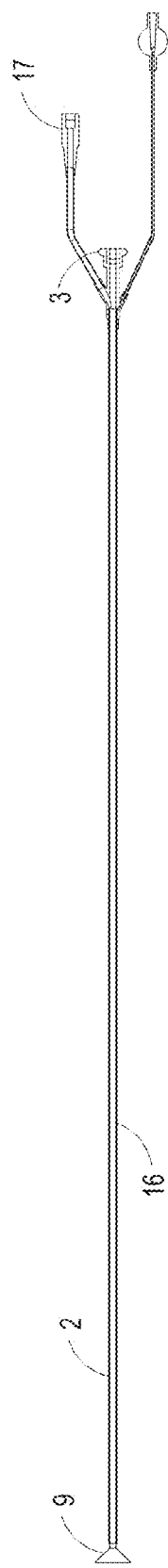
FIGS. 28 and 29 illustrates the suction catheter that can include a funnel tip, catheter shaft, and connector with seal, according to some embodiments of the invention.
Figure 29:
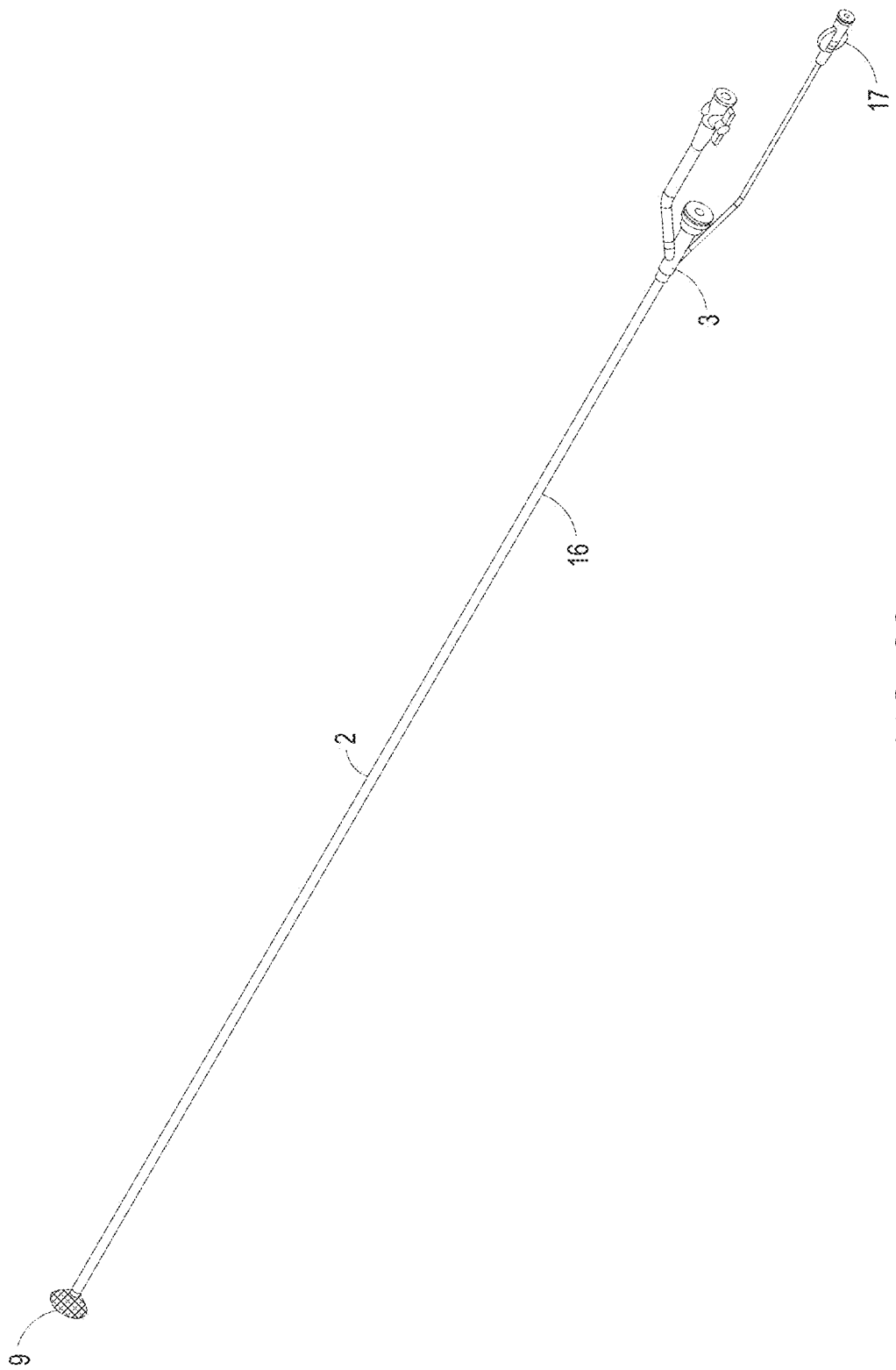
Figure 30:
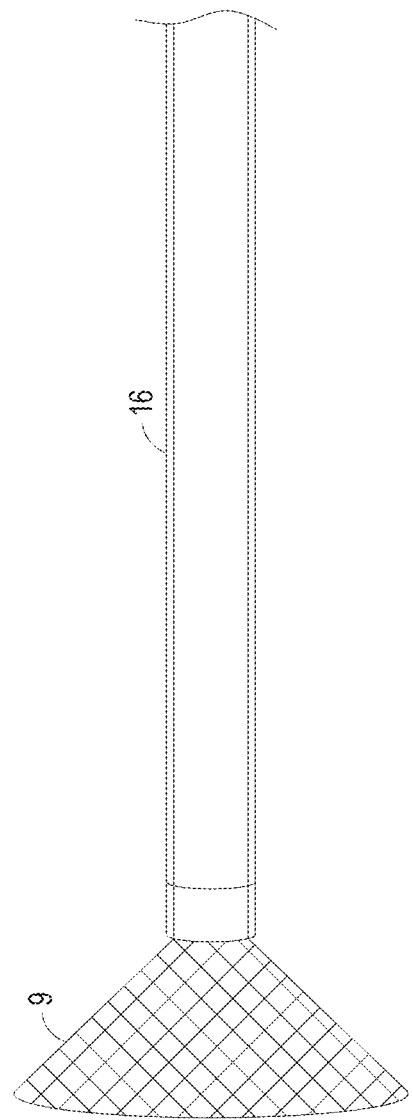
FIG. 30 illustrates the distal end of the suction catheter indicating the funnel tip and catheter shaft, according to some embodiments of the invention.
Figure 31:
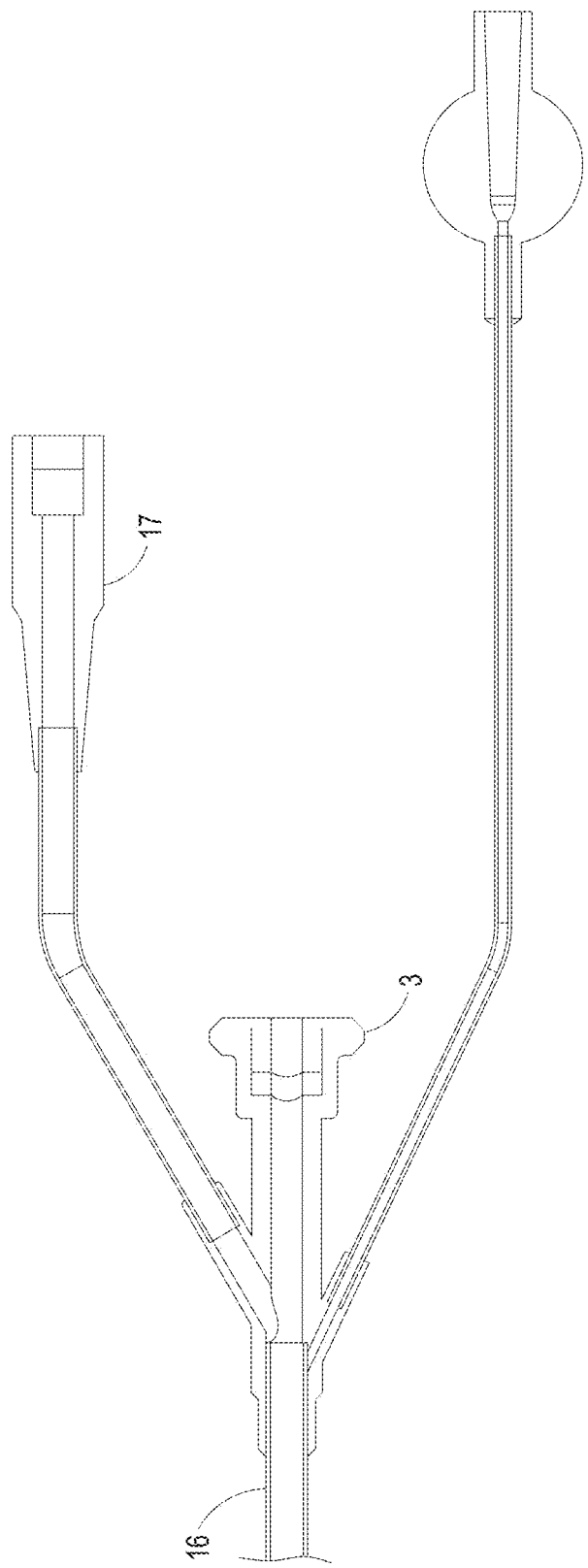
FIG. 31 illustrates the proximal end of the suction catheter indicating the connector with seal and ports for use with filter chamber and access to flush catheter lumen, according to some embodiments of the invention.
Figure 32:
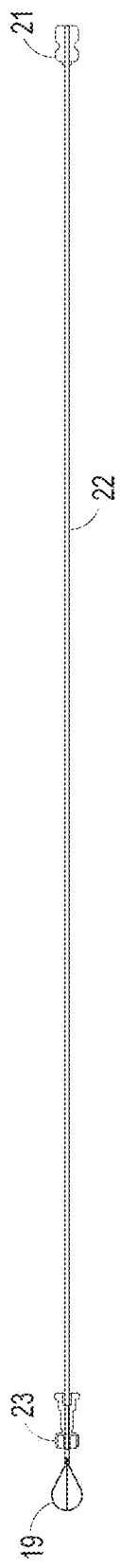
FIGS. 32-41 illustrate different macerator designs and shapes, according to some embodiments of the invention.
Figure 33:
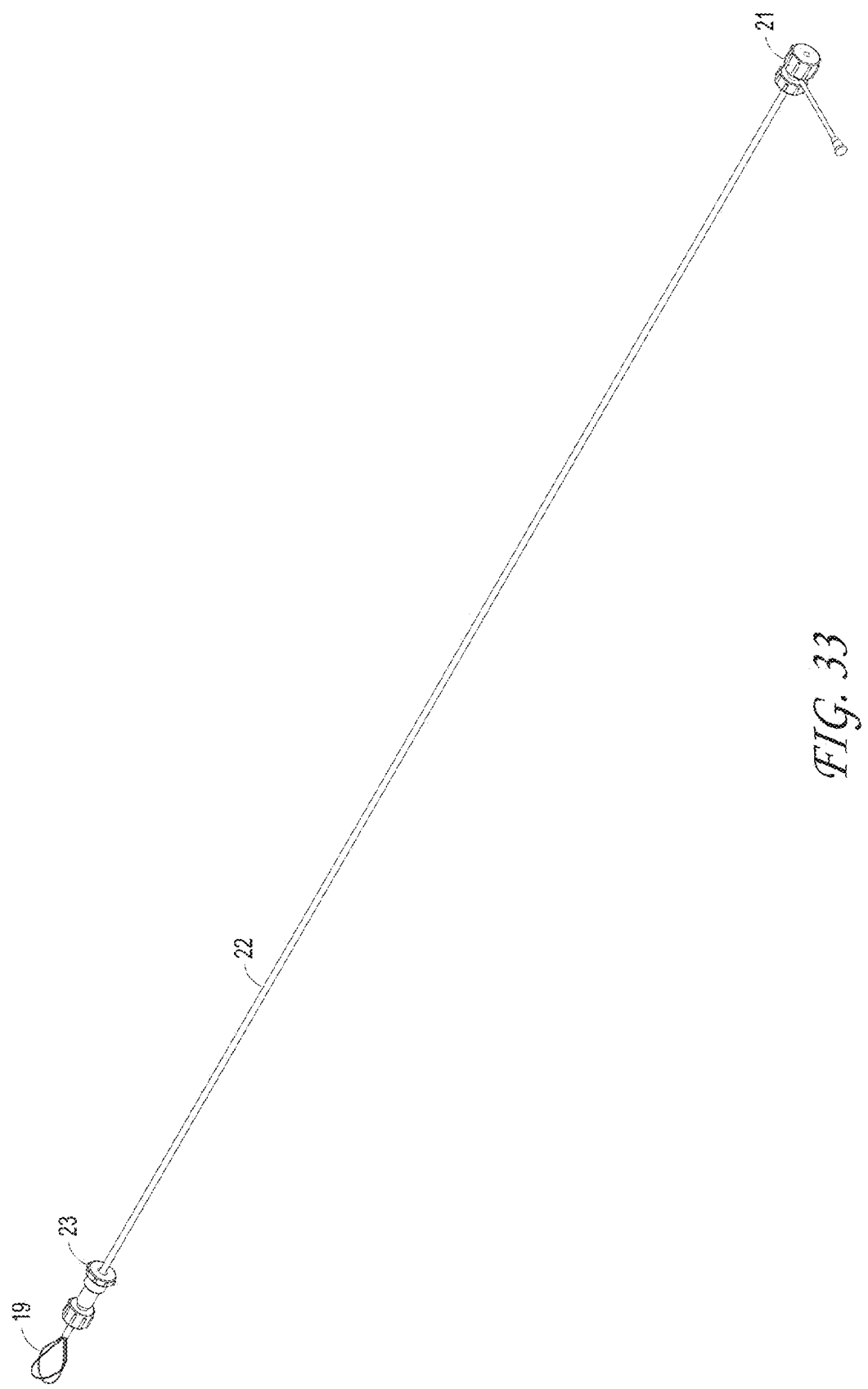
Figure 34:
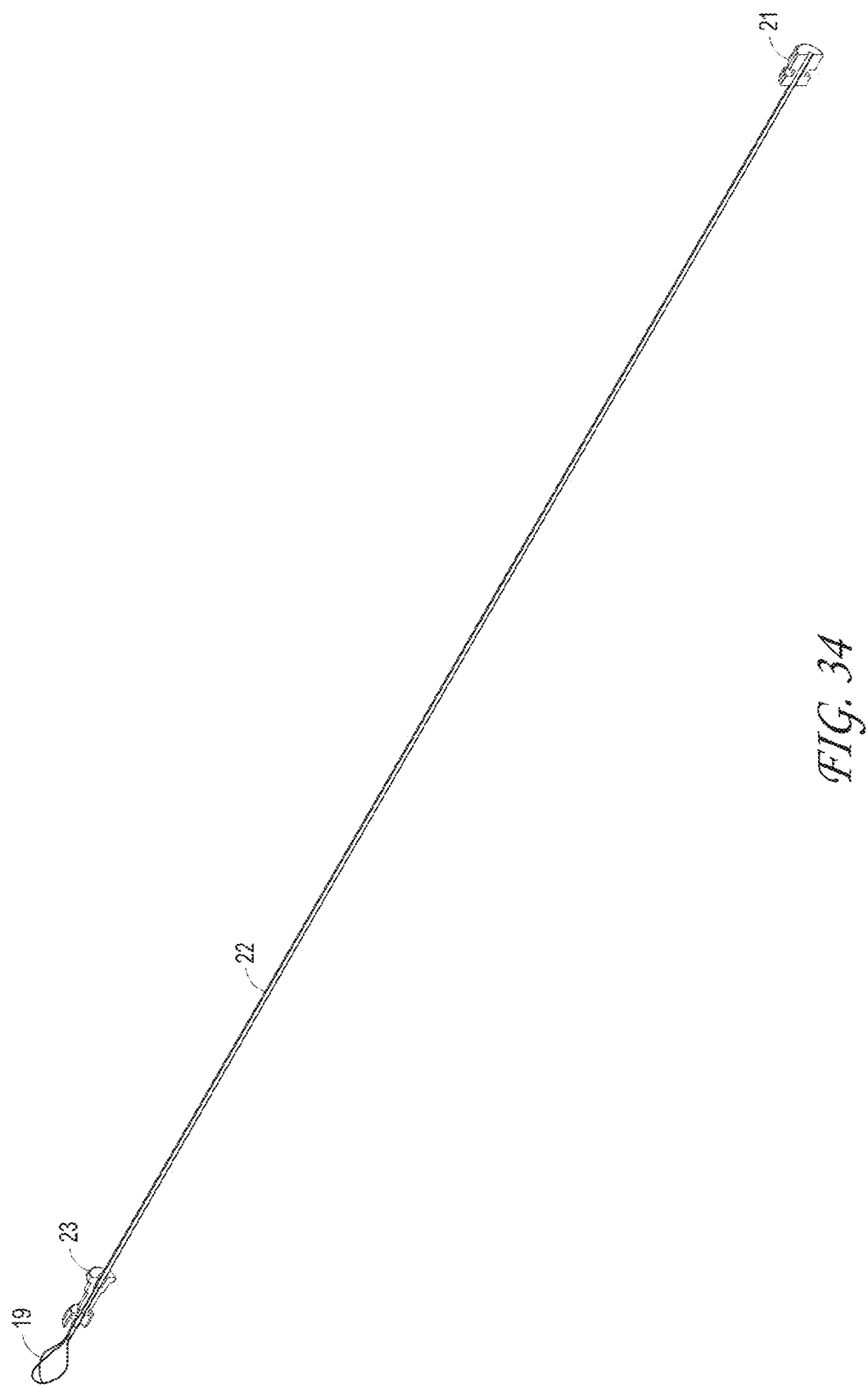
Figure 35:
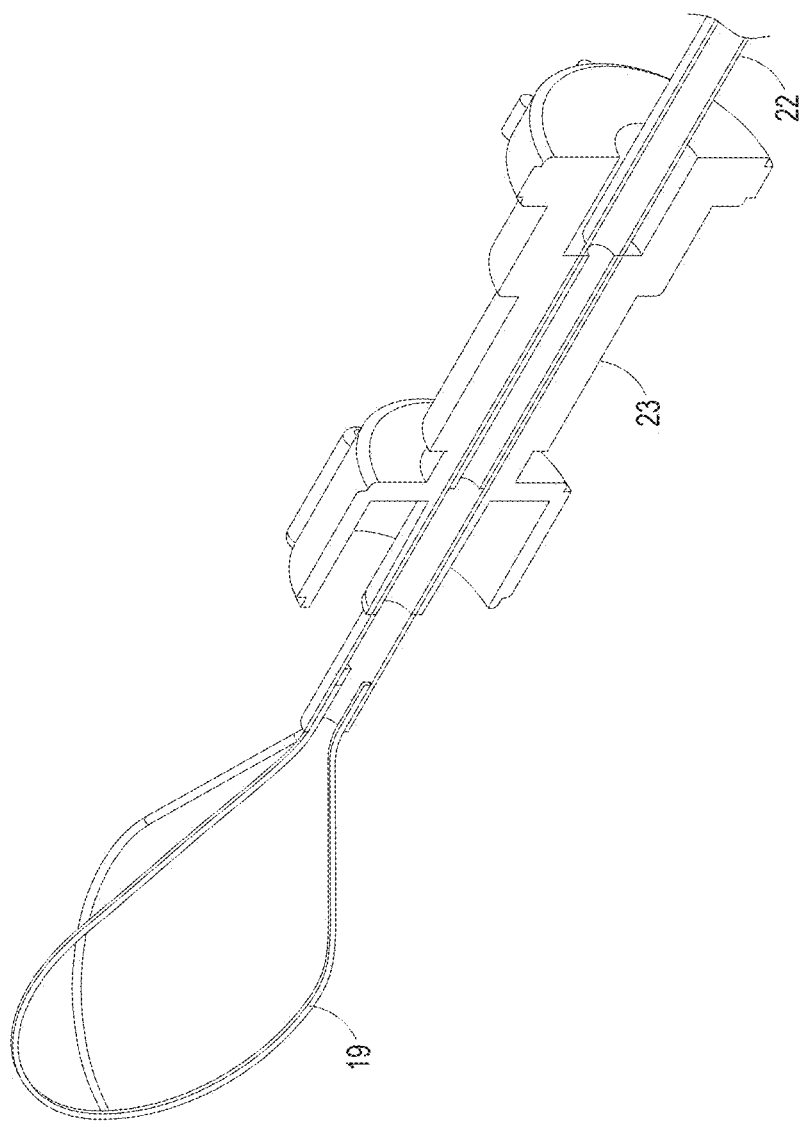
Figure 36:
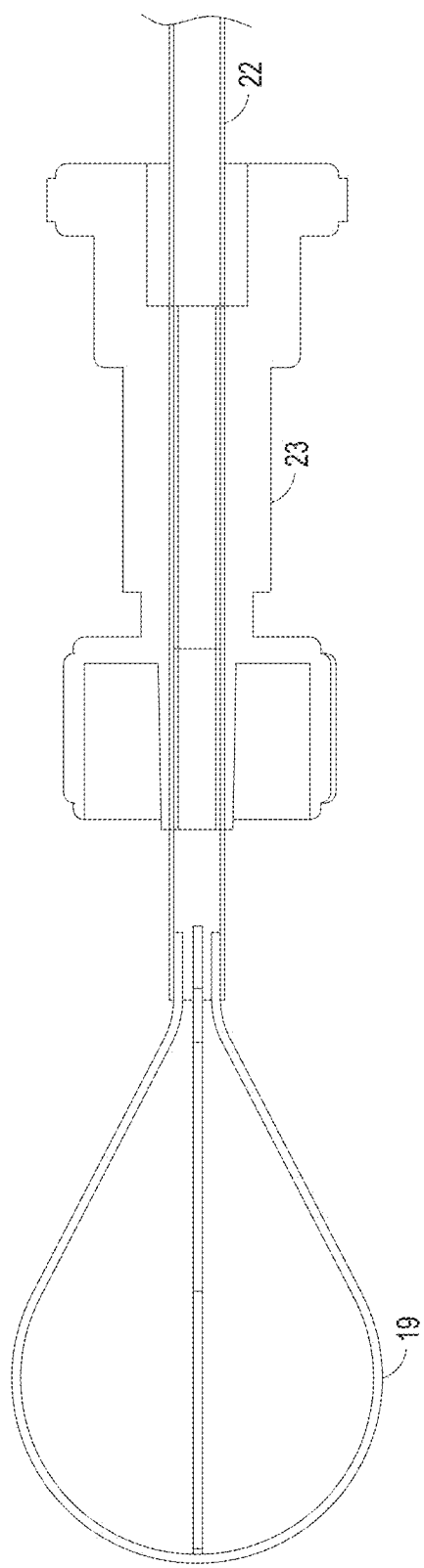
Figure 37:
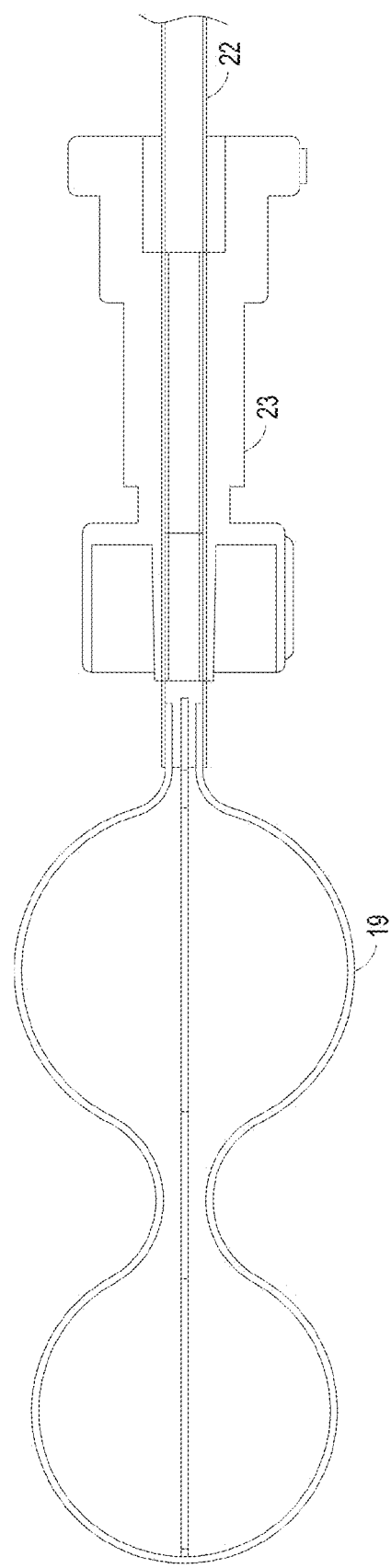
Figure 38:
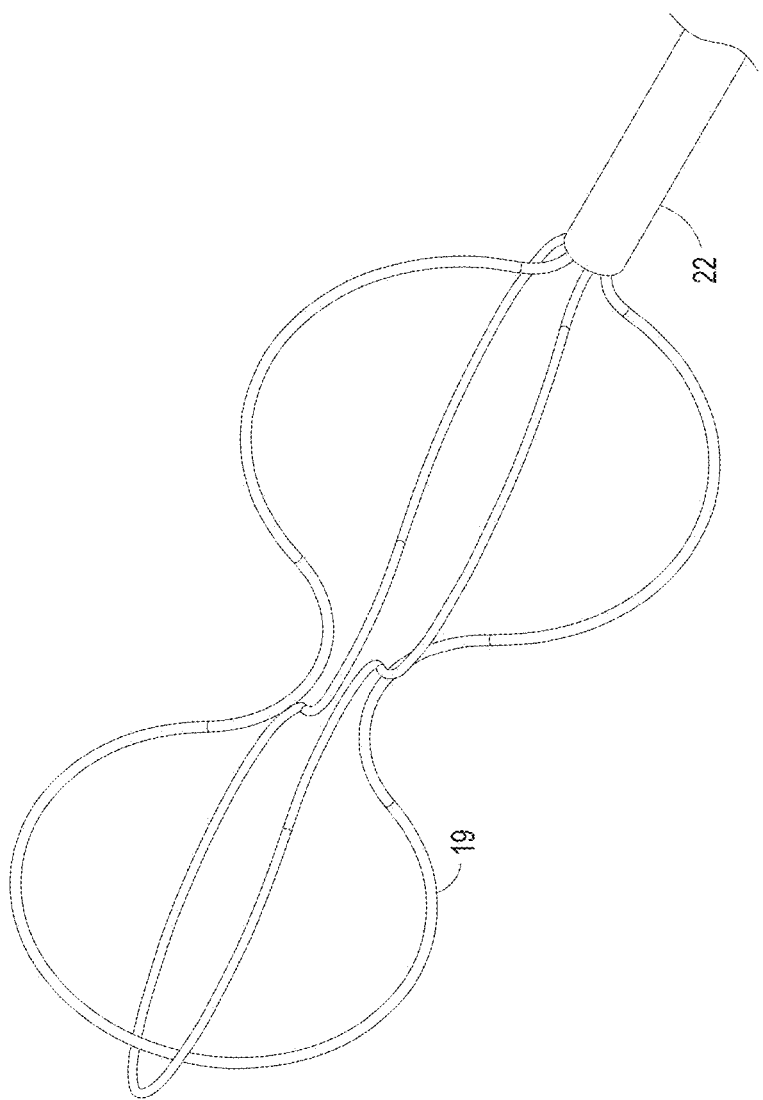
Figure 39:
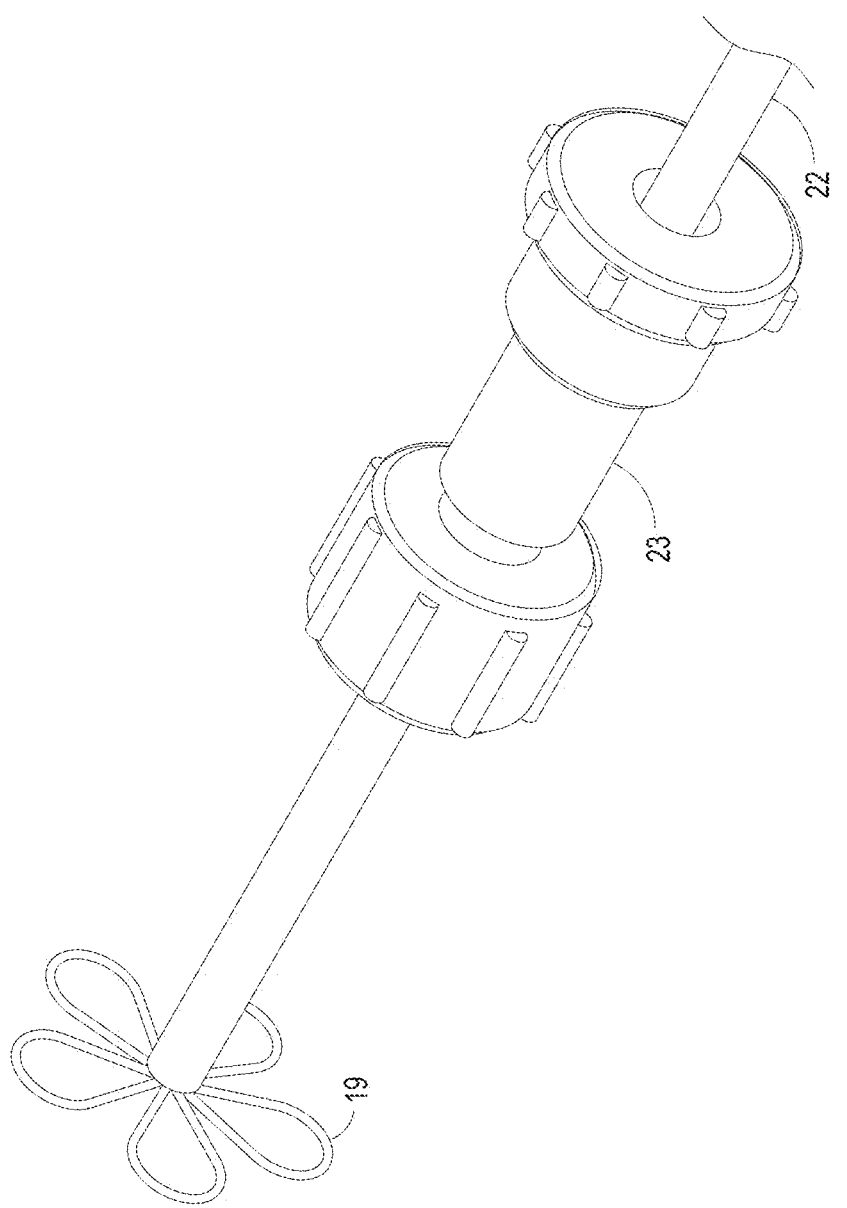
Figure 40:
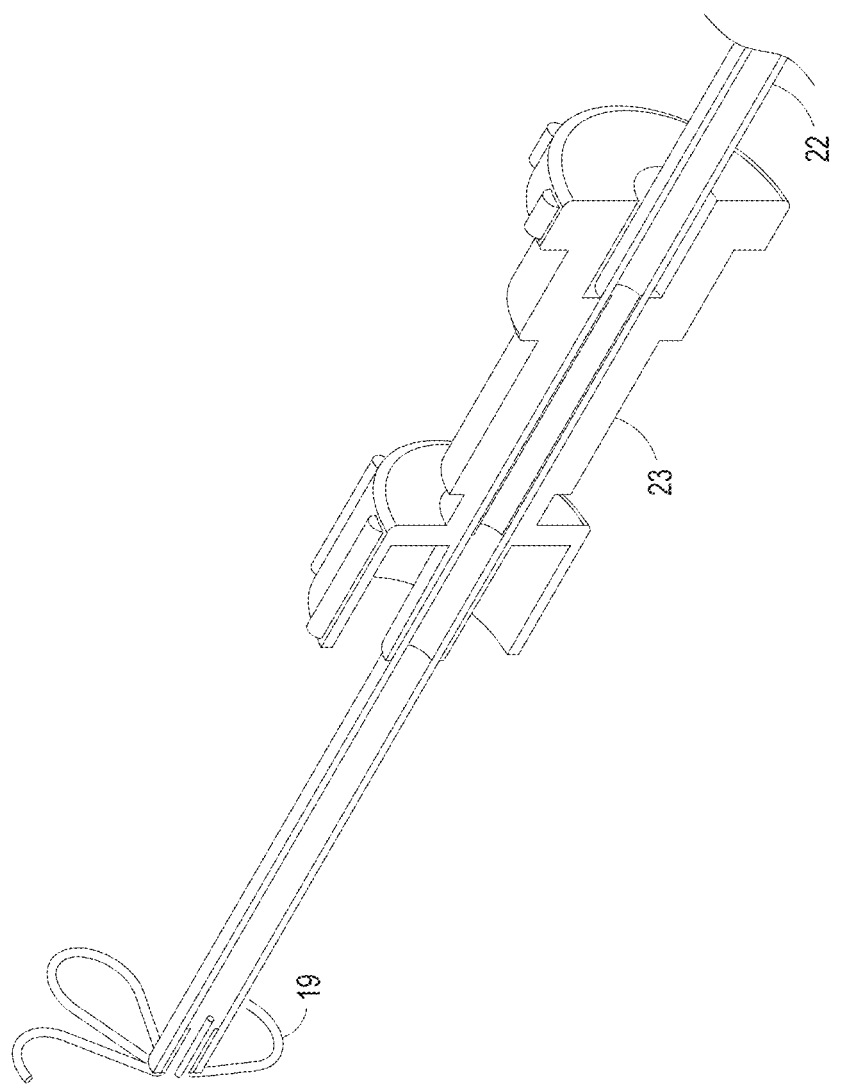

In some embodiments, as illustrated in FIGS. 28-29 for example, an optional suction catheter 2 can function to aspirate thrombus within the ALTC Device 8. The suction catheter 2 can include in some embodiments a distal funnel tip 9, elongate shaft body 16, and proximal connector with seal 3. FIG. 30 illustrates a close-up view of the funnel tip 9 which can be attached at the suction catheter shaft 16 distal end to aid in retrieving the thrombus and allow efficient suction. The funnel tip 9 can be made of, for example either polymeric and/or metallic materials. It can be tubular in shape, woven or braided, in some embodiments. Funnel tip 9 can be in various configurations to allow better retrieval and suction. In some embodiments, the funnel tip 9 has a funnel shape with a first, larger distal diameter, a transition section, and a second, smaller proximal diameter as illustrated. The suction catheter shaft 16 creates a pathway for the aspirated thrombus to travel proximally and exit the body and in some embodiments into the optional filter collection chamber. The shaft can be of various diameters, lengths and/or geometries to aid in the removal of materials such as blood clots. The suction catheter shaft can be made from suitable materials such as and not limited to Nylon, Polyurethane, Pebax, Polyethylene, PET, PTFE, ePTFE, PEEK, and polypropylene. In some embodiments, the suction catheter Shaft distal end is expandable so to accommodate large amount of blood clots. The suction catheter 2 can attach to the proximal end of filter collection chamber 5 to enable thrombus aspiration (or removal). In some embodiments, the suction catheter shaft 16 is deflectable at one, two, or more locations along the shaft length to accommodate various tortuous paths such as entry into the right atrium, right ventricle, main pulmonary artery, and left and right pulmonary artery. A proximal flush port 13 is also illustrated.

Figure 41:
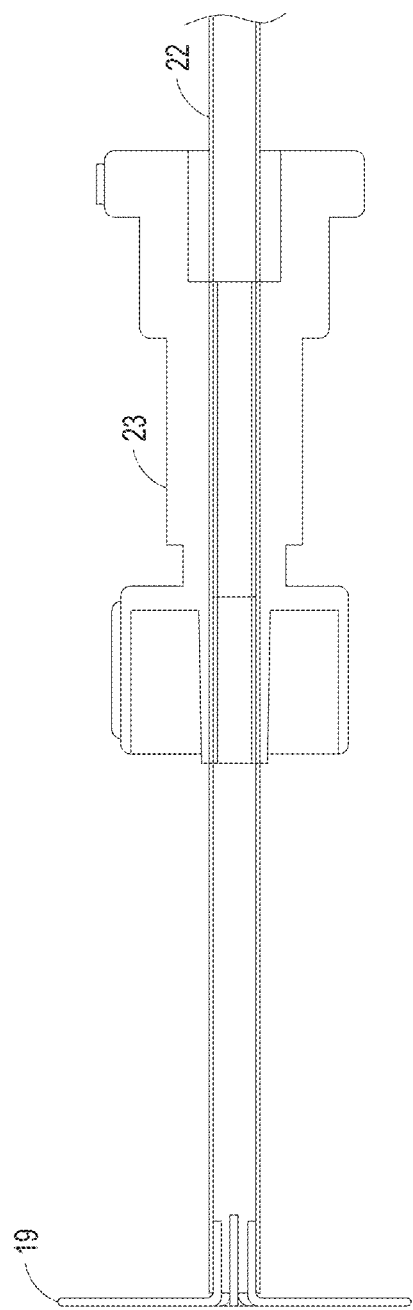

In some embodiments, a mechanical thrombectomy tool such as macerator 19 shown in FIGS. 32-41 for example, can function to disrupt and break up the thrombus within the ALTC Device 8. The macerator 20 can include a disruptor 19, shaft 22 and proximal connector with seal 21. Adjustable Touhy knob 23 distally is also shown just proximal to disruptor 19. The disruptor 19 can be attached to the distal end of the shaft 22. The macerator 20 can have various end effector tip configurations as illustrated in FIGS. 35-41 depending on the desired clinical result to break up the thrombus within the ALTC Device 8, including a bulbous shape (FIG. 36), proximal and distal bulbs with a narrow waist (FIG. 37), a plurality of proximal and distal bulbs with a narrow waist each offset by an angle, such as about 90 degrees (FIG. 38), a flower petal design with petals radiating radially outwardly from a central hub (FIG. 39), a hemi-petal design (FIG. 40), or a substantially linear design orthogonal from the longitudinal axis of the shaft 22 (FIG. 41). The disruptor 19 collapses during insertion through the suction catheter 2 system and expands once exiting the catheter. The disruptor 19 can be made of, for example, metallic materials such as stainless steel, Nitinol, cobalt chrome, etc. The macerator can be activated either by manual rotation, manipulation and/or a motorized handle.

To macerate the thrombus, the macerator 19 is inserted through the suction catheter 2 and position within the ALTC Device 8. A manual technique applies to the luer connector 21 of the macerator 19 by rotating the luer connector 21 causing the disruptor 20 to rotate thereby breaking up the thrombus. Alternatively, the macerator 19 can be used with a motorized handle (not shown). Traversing the disruptor 20 axially through the entire length of the ALTC device 8 can aid in breaking up the thrombus.

The filter collection chamber 5 (FIG. 42) can function to suction and collect the blood clots. The filter collection chamber 5 can include, for example, a collection chamber 325, filter 324, plunger 323, inflow port 327 and outflow port 326. The filter collection chamber 5 can have an outflow port 326 attaching to the suction catheter 2 connector and an inflow port 327 where a syringe or a similar device can attach for aspiration. The collection chamber 325 has a filter system 324 residing inside the chamber 325 to allow filtering the blood and thrombus. The chamber 325 also has a plunger 323 for use in injecting fluid such as saline to fill the chamber 325 and push filtered blood back into the vasculature. The plunger 323 can serve as a seal on one side of the chamber.

Figure 42:
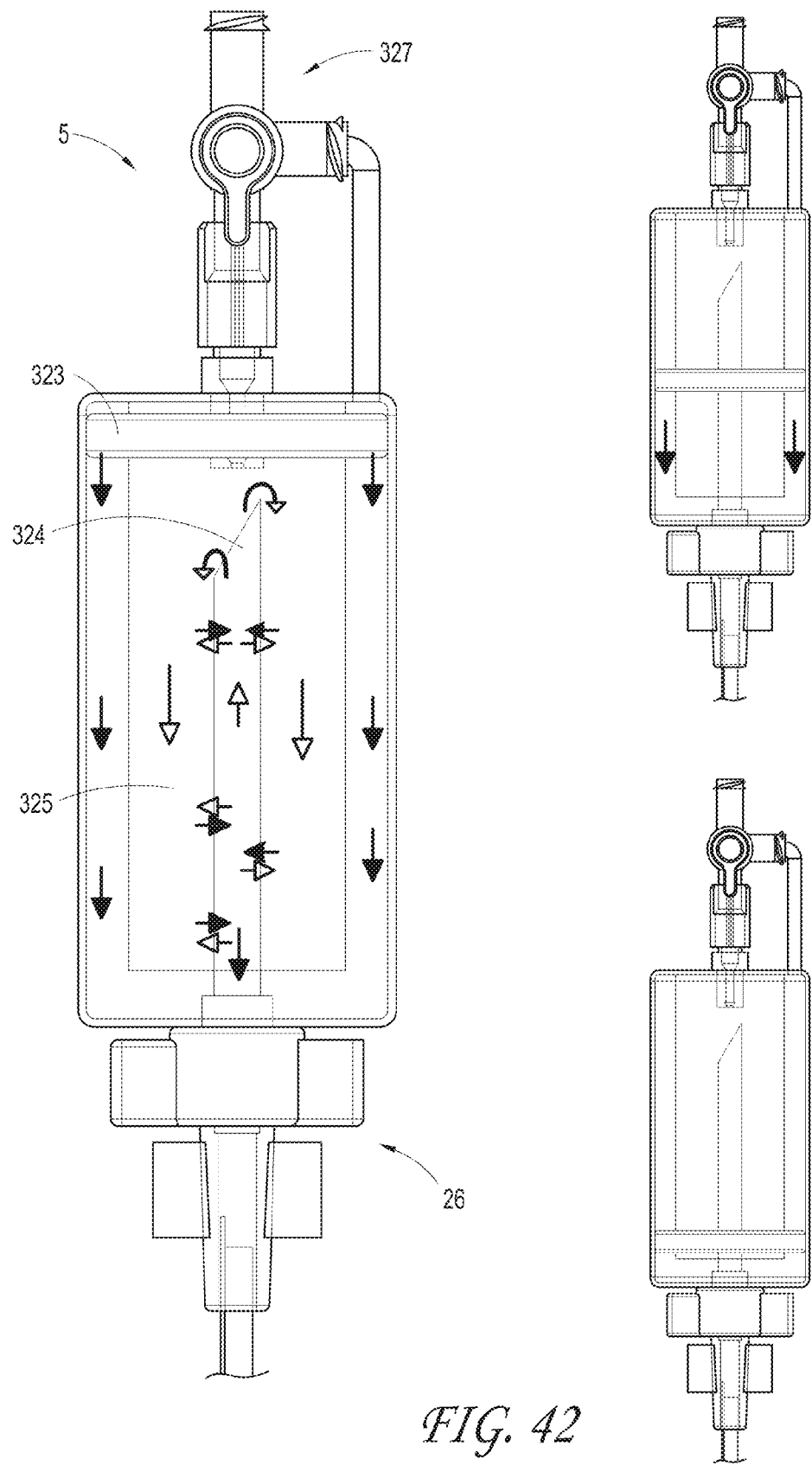
FIG. 42 illustrates a filter collection chamber that can include an inflow port to connect to a syringe, an outflow port to connect to the suction catheter, a plunger, a filter to filter blood clot or debris and retain in the chamber and a chamber to collect blood clot or debris, according to some embodiments of the invention.

To aspirate the thrombus from the system, the suction catheter 2 is attached to the filter collection chamber 5 (FIG. 42). A large syringe attaches to the proximal end of the filter collection chamber 5. Applying suction using the syringe causes the thrombus and blood clots to migrate into the filter collection chamber 5. Once all the thrombus is contained within the chamber 5, close stopcock, detach the syringe and fill with saline and reattach the syringe to the filter collection chamber 5. Alternatively, an extension tube and external saline filled syringe can be used to fill saline into the suction syringe. Injecting via the syringe will push saline into the chamber 325 causing the plunger 323 to push the blood back into the vasculature. The chamber 325 will return the blood and leave the thrombus inside the chamber 325. Alternatively, the filter collection chamber 5 can be detached without returning filtered blood to the system. Once the thrombus is removed, retract the suction catheter 2 inside the outer sheath 1. Retract the ALTC Device 8 into the outer sheath 1 and remove the entire system from the body.

Catheter systems as described herein can be utilized for a variety of indications depending on the desired clinical result. In some embodiments, the use is not limited to venous systems and can apply to other arterial, venous, or nonvascular areas such as neurovascular, peripheral vascular, cardiovascular, temporary embolic protection device for a cardiovascular procedure such as valve replacement, carotid protection, pulmonary protection during deep vein thrombectomy or embolectomy), or retrieval of an implant, medical device, or other material.

Figure 43:
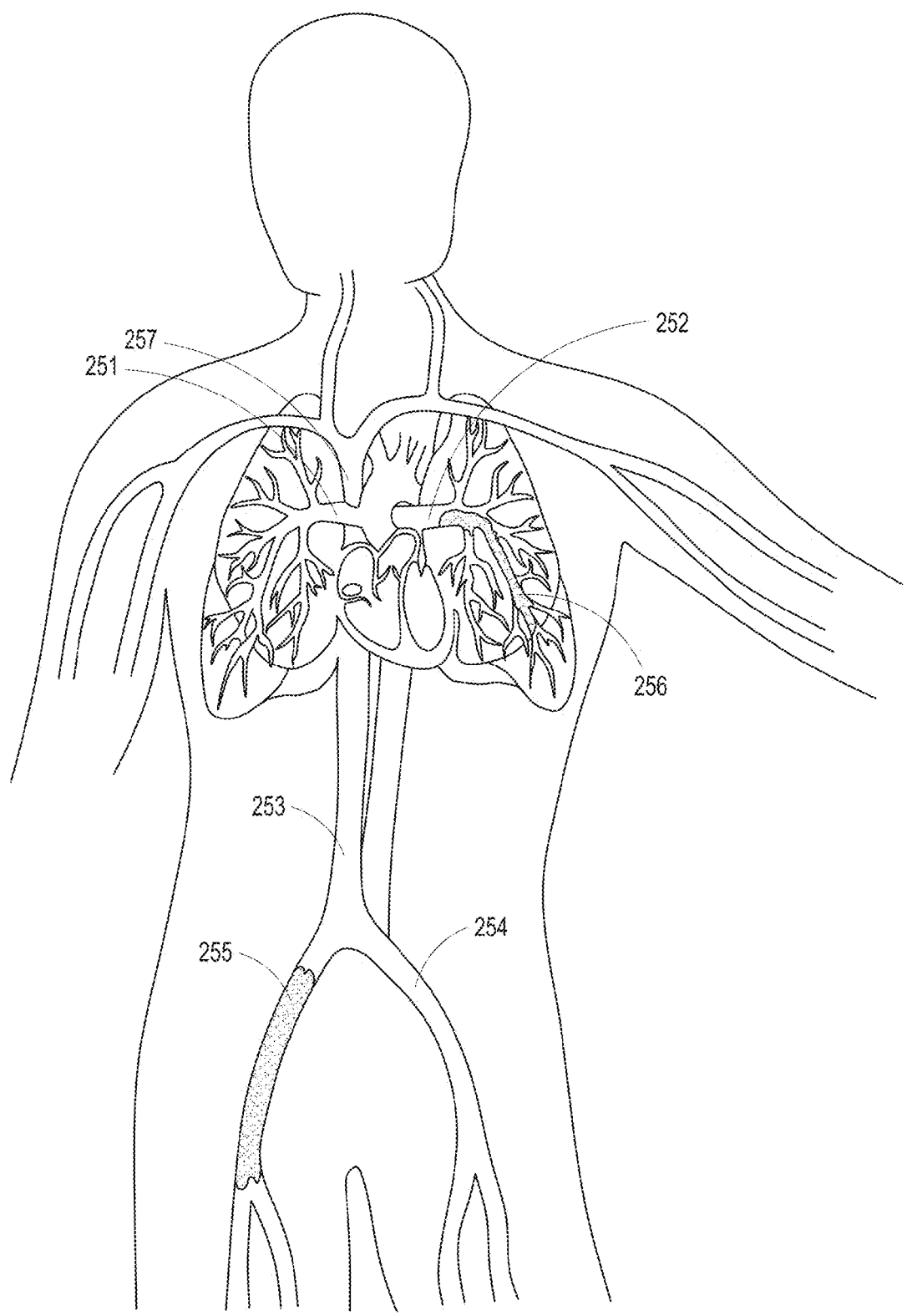
FIG. 43 illustrates a blood clot lodging in the left side of pulmonary system, according to some embodiments of the invention.

FIG. 43 illustrates a blood clot lodging in the left side of the pulmonary system. Shown is the right pulmonary artery 251, left pulmonary artery 252, inferior vena cava 253, left iliac artery 254, right iliac artery 255, a pulmonary embolus 256 in the left pulmonary artery 252 distally, and the superior vena cava 257.

Figure 44B:
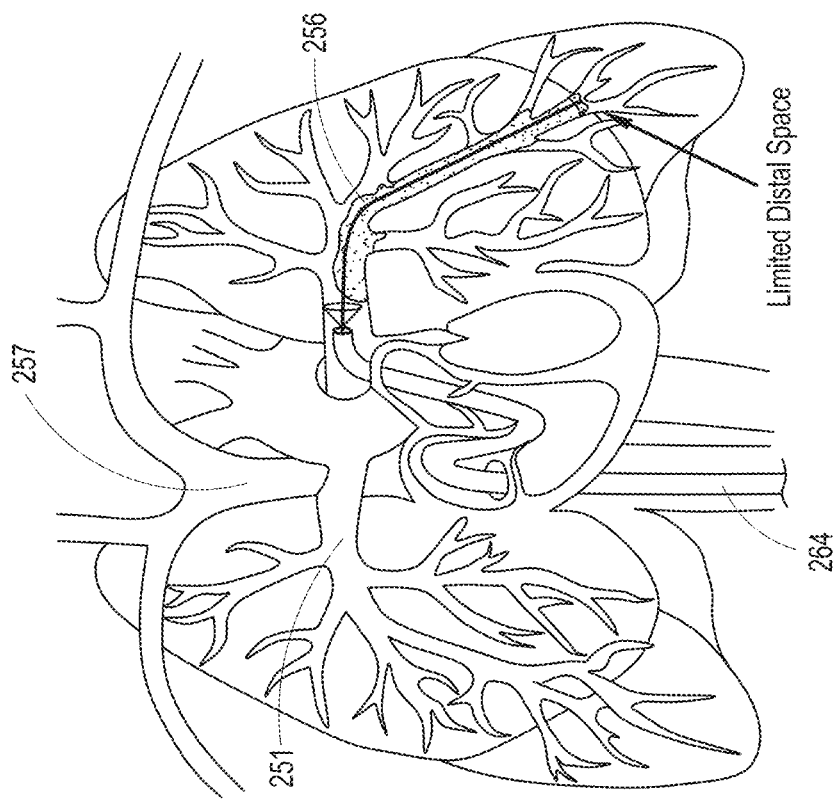
FIGS. 44A and 44B illustrate blood clots residing in the left side pulmonary system and the capture device respectively, according to some embodiments of the invention.
Figure 44A:
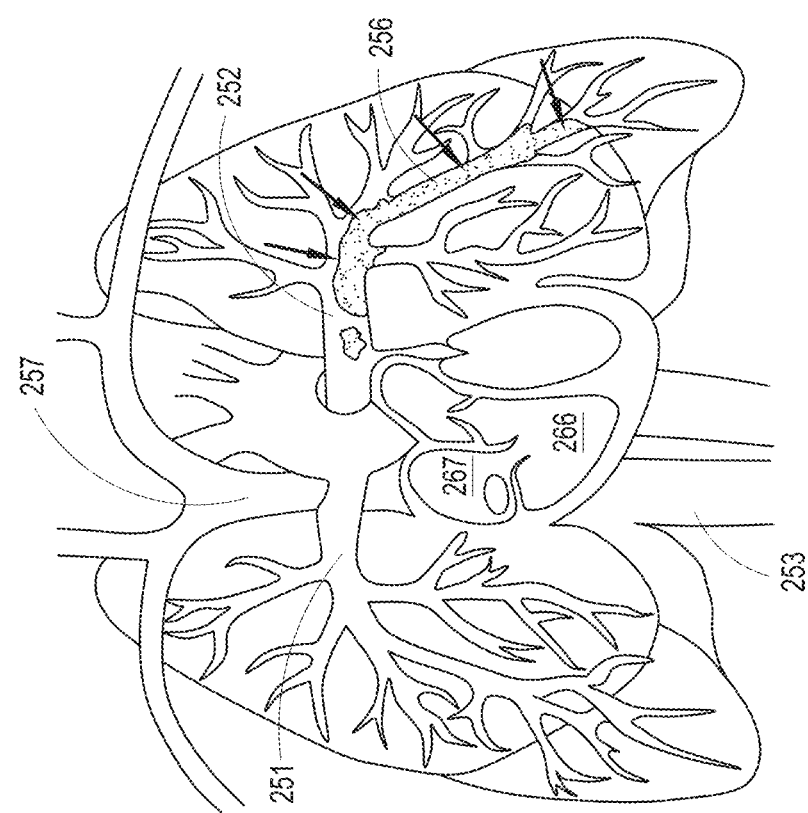

FIGS. 44A and 44B illustrate blood clots residing in the left side pulmonary system and the capture device respectively, according to some embodiments of the invention. In addition to the anatomical features illustrated in FIG. 43, also shown is the guide catheter 264, right ventricle 266, and right atrium 267. As shown in FIG. 44B, capture devices as described and illustrated herein can advantageously be utilized when there is very limited distal space, as the device is functional throughout a wide working axial range as discussed elsewhere herein.

Figure 45:
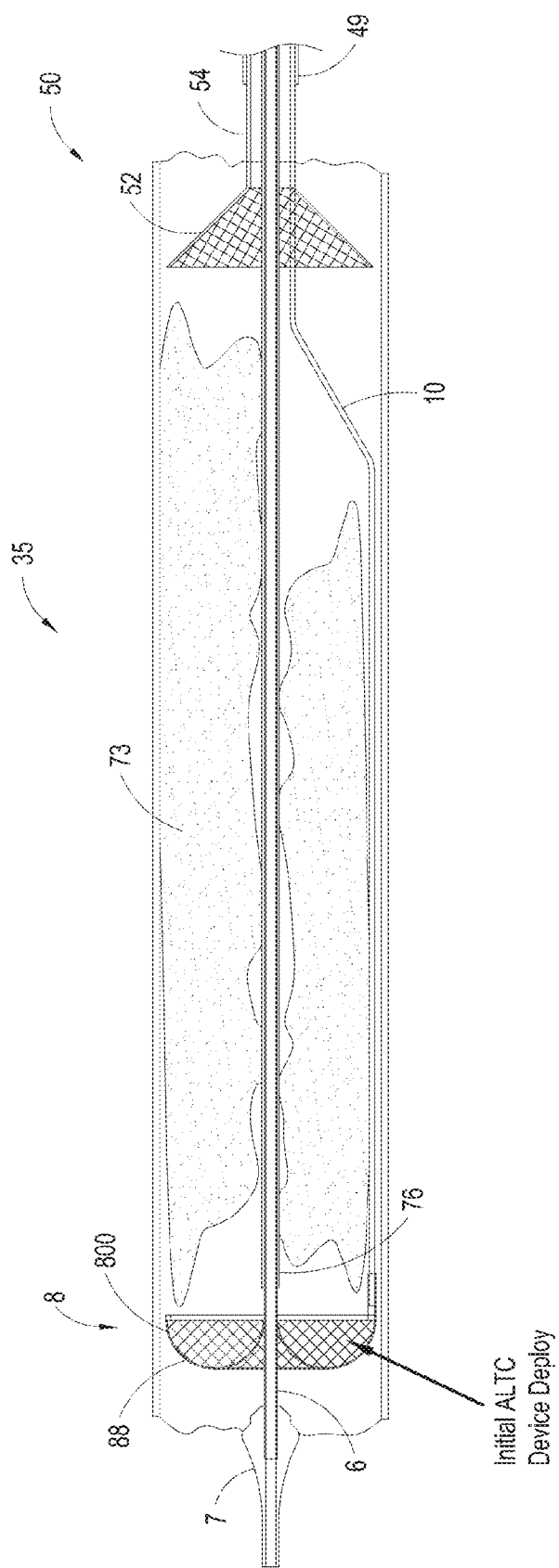
FIG. 45 illustrates the initial deployment configuration of the axial lengthening thrombus capture device positioned distal to the thrombus occluded area and a funnel tip positioned proximal to the thrombus occlusion, according to some embodiments of the invention.
Figure 46:
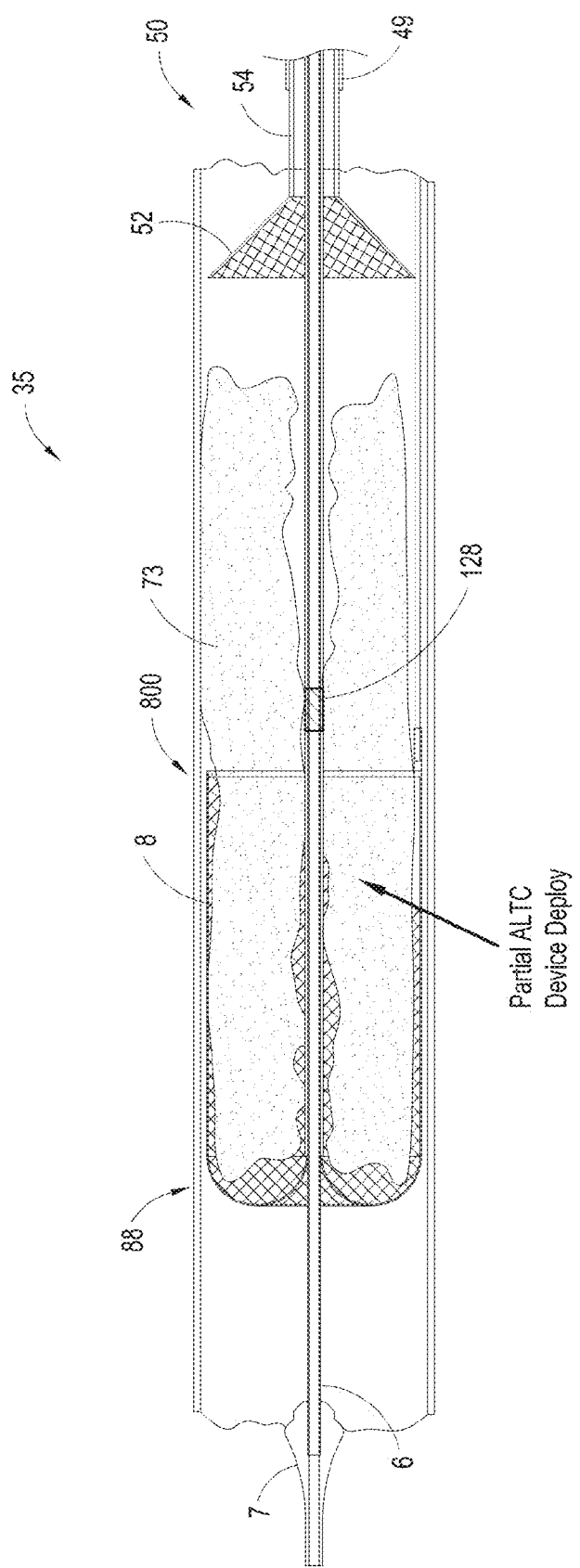
FIG. 46 illustrates the axial lengthening thrombus capture device lengthening proximally to capture the thrombus, according to some embodiments of the invention.
Figure 47:
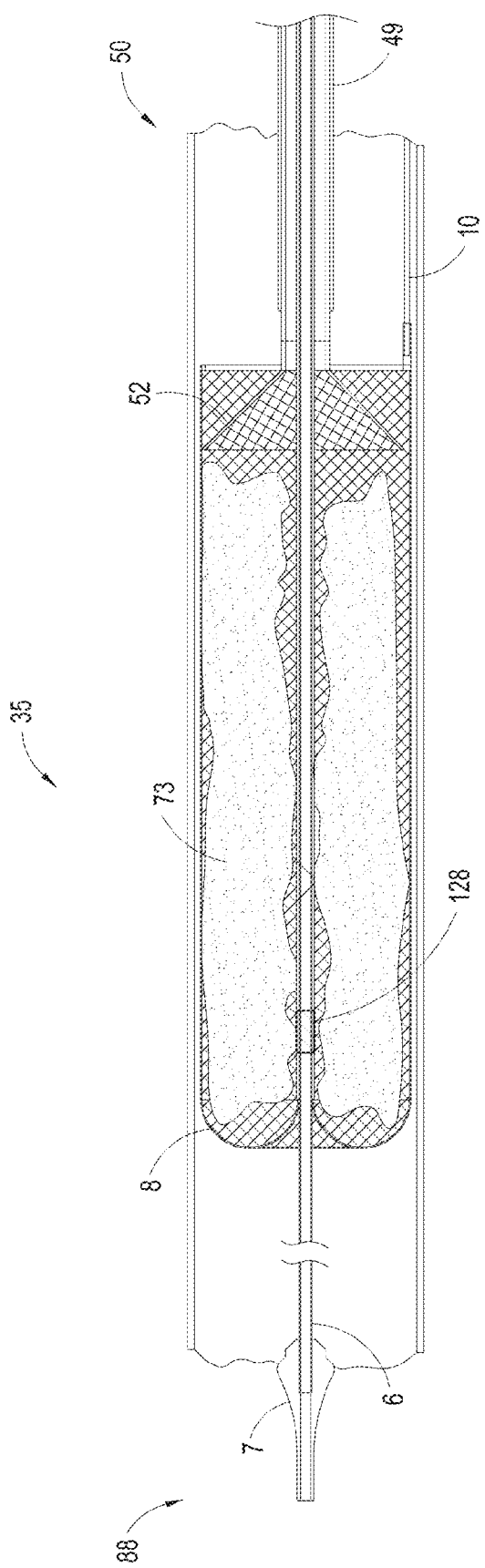
FIG. 47 illustrates the axial lengthening thrombus capture device completely capturing the thrombus, and a funnel tip is inside the axial lengthening thrombus capture device.

FIGS. 45-47 illustrate capture of a thrombus within a vessel, according to some embodiments. FIG. 45 illustrates the initial deployed configuration of the axial lengthening thrombus capture device (e.g., tubular mesh) 8 with end 800, dynamic fold point 88, and reserve radially compressed segment (not shown) terminating proximally at point 128 where the radially compressed segment is fixably attached to the outer sidewall of the guidewire lumen 6 is shown. The expanded segment of the tubular mesh 8 is positioned distal to the thrombus 73 occluded area and the expanding guide catheter 50 including distal funnel tip 52 with proximal expandable section, inner catheter 54 and outer catheter 49, or in some embodiments suction catheter funnel tip positioned proximal to the thrombus occlusion 73, according to some embodiments of the invention. In some embodiments, expanding guide catheter 50 as described elsewhere herein or a suction catheter can be utilized depending on if suction is desired. Also shown proximally is inner sheath 54 and outer sheath 49 of expanding guide catheter 50. Actuation of capture pullwire 10 alone or with capture catheter 12 such as axially in an appropriate direction (or capture catheter coupled to the outer sheath (not shown) in embodiments with a sleeve as previously described) can result in axial lengthening or shortening of the ALTC device 8 depending on the desired clinical result. FIG. 46 illustrates the axial lengthening tubular mesh 8 expandable segment lengthening proximally to capture the thrombus, according to some embodiments of the invention, with the associated radially compressed segment shortening reciprocally. FIG. 47 illustrates the axial lengthening thrombus capture device completely capturing the thrombus, and the expanding guide catheter funnel tip or alternatively the suction catheter funnel tip is inside the axial lengthening thrombus capture device. Subsequent suction via the suction catheter 2 in embodiments where suction is utilized can be performed to remove the blood clot or thrombus. The ALTC Device can lengthen to have a maximal length that covers the entire length of catheter system from, e.g., about 0.5 cm to about 125 cm. In some embodiments, the ALTC device may lengthen to about or at least about 2, 3, 4, 5, 6, 7, 8, 9, 10, 11, 12, 13, 14, 15, 20, or more centimeters. Depending on vessel diameter, the outer diameter of the ALTC device can range from, in some embodiments, about 1 millimeter up to about 80 millimeters. For example, large vessels such as the inferior vena cava, superior vena cava, descending, and ascending aorta, the diameter can range up to about 60, 70, 80, 90, 100 millimeters or more. Small vessels in the neurovascular system can be, for example, as small as about or less than about 5, 4.5, 4, 4.5, 3, 2.5, 2, 1.5, 1, 0.5, or less millimeters in diameter. The diameter of the ALTC device can achieve the similar effect of reducing or stretching the ALTC device diameter. In some embodiments, suction is not utilized or required, and the ALTC device envelops the clot, which can be mechanically pulled back into the capture catheter. In some embodiments, the ALTC device can be utilized to treat, for example, a clot in the carotid or cerebral arterial or venous circulation. The vessels to be treated could include, for example, the Circle of Willis, left or right common carotid or internal carotid arteries, anterior cerebral arteries, anterior communicating arteries, middle cerebral artery, posterior communicating arteries, carotid siphon, basilar arteries, vertebral arteries, or ophthalmic arteries for example, or any branches thereof. In some embodiments, the ALTC device can be utilized to treat, for example, a femoral vein, a brachial vein, a pulmonary vein, a breast vein, a cerebral vein, a brain sinus vein, a renal vein, a portal vein, a jugular vein, or another vein.

Figure 48A:
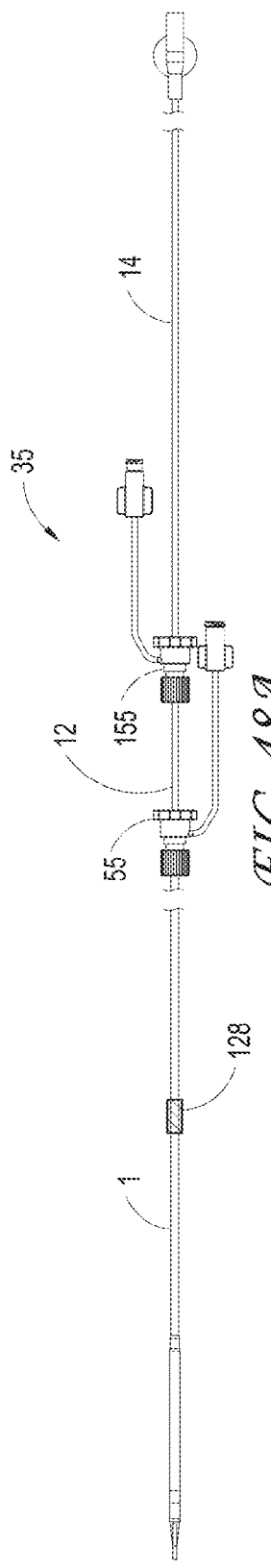
FIG. 48A illustrates the delivery configuration of the capture catheter device, according to some embodiments of the invention.
Figure 48B:
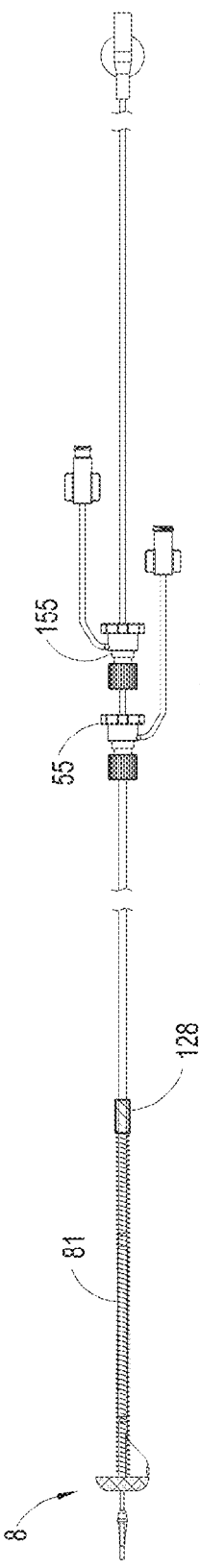
FIG. 48B illustrates the initial deployment position of the axial lengthening thrombus capture device, according to some embodiments of the invention.
Figure 48C:
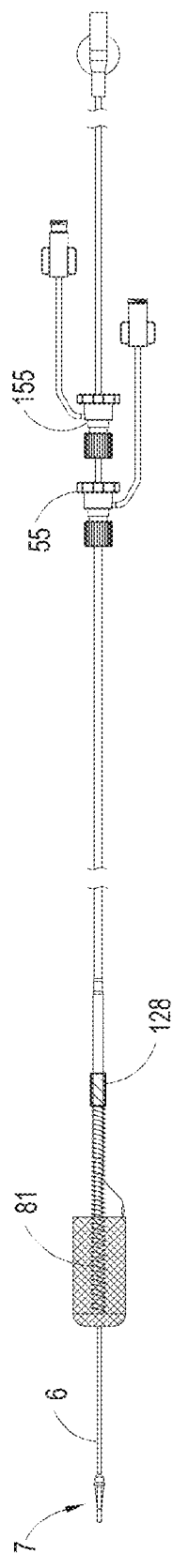
FIG. 48C illustrates the lengthening of the axial lengthening thrombus capture device, according to some embodiments of the invention.
Figure 48D:
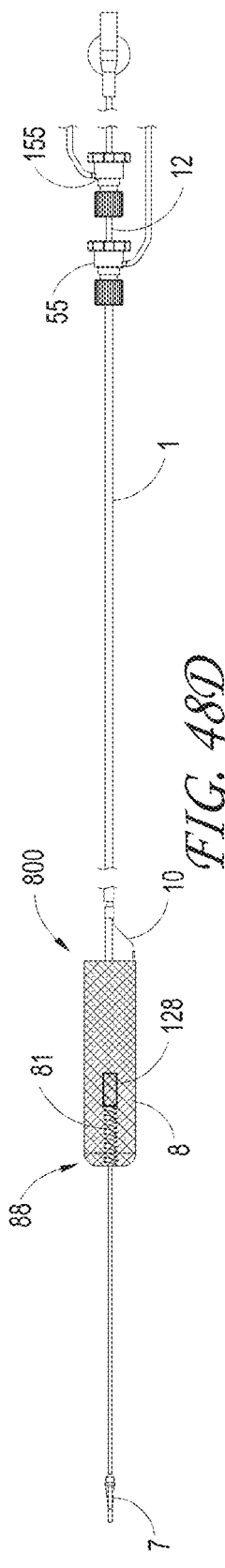
FIG. 48D illustrate the final deployment of the axial lengthening thrombus capture device, according to some embodiments of the invention.

FIG. 48A illustrates another delivery configuration of the clot capture system 35 that can include features as previously described, according to some embodiments of the invention. FIG. 48B illustrates the initial deployment position of the axial lengthening thrombus capture device, according to some embodiments of the invention, and reversible coupling of the hub 55 of the capture catheter 155 to the hub 55 of the outer sheath. FIG. 48C illustrates the further lengthening of the expanded segment of the axial lengthening thrombus capture device, according to some embodiments of the invention, with reciprocal shortening of the reserve compressed segment 81. As illustrated, the guidewire tube 6 with nose tip 7 is maintained in position while the capture catheter reversibly coupled to the outer sheath can be withdrawn proximally. FIG. 48D illustrate the final deployment of the axial lengthening thrombus capture device at its maximal working length, according to some embodiments of the invention.

In some embodiments, systems and devices as disclosed herein can involve a general percutaneous technique, a cut-down procedure, or minimally invasive technique such as transapical, thoracoscopic, laparoscopic, or other techniques, for example, and not limited to transfemoral, transradial and/or internal jugular venous access. The technique can also apply to the arterial system, including neurovascular, cardiovascular, and peripheral vascular applications, as well as for use as an embolic protection device such as for a cardiovascular procedure such as valve replacement or repair for example. In some embodiments, a thrombectomy system can be delivered downstream of the aortic root, such as prior to the aortic arch, and a variable-length shape memory mesh structure such as an ALTC device with an open proximal end and closed distal end expanded prior to the index cardiovascular procedure, to capture downstream emboli, calcifications, or other debris. In some embodiments, the system can be deployed to prevent embolization during a deep vein thrombectomy or pulmonary embolectomy, for example. In another embodiment, the system can be deployed to prevent embolization or retrieval during acute ischemic stroke. Systems and methods as disclosed herein can also be utilized in non-vascular anatomy such as the biliary tree to capture gallstones, common bile duct stones, and pancreatic duct stones, for example, in the ureters or bladder to capture kidney stones, or in the fallopian tubes to capture ova or other materials, or in the gastrointestinal tract such as the esophagus, stomach, duodenum, jejunum, ileum, or colon to capture, for example, foreign bodies. Described herein are some embodiments of using the venous system to access the pulmonary artery to treat pulmonary embolism. The technique can also apply to other areas of the vasculature. Initial puncture to access the femoral vein. A short access guidewire is inserted into the femoral vein. Next, an appropriate 5F or 6F introducer sheath is inserted. The guidewire is exchanged for a 180 cm, 260 cm or 300 cm guidewire and advance pass the inferior vena cava, right atrium, right ventricle and the pulmonary artery to access the occluded treatment area. A longer length introducer/guiding catheter may be necessary to cross the tricuspid and pulmonary valve. Once the guidewire passes through the occluded treatment area, the 5F or 6F introducer sheath is exchanged for a long guiding catheter and position proximally near the occluded area. The catheter system 35 is inserted over the wire and through the guiding catheter and advance distally to the occluded area. The catheter system 35 can also utilize the outer sheath deflectable features to navigate through the vasculature without the use of a guiding catheter. Next, the catheter system's nose tip 7 passes through the occluded treatment area and positioned distal to the occluded treatment area. The Outer Sheath 1 is retracted to deploy the thrombus capture guide 11. The outer sheath 1 is retracted past the thrombus and positioned proximal to the thrombus (occluded area). The Suction Catheter 2 advances distally outside the Outer Sheath 1 and positions proximally to the occluded area, if suction is utilized.

To retrieve and capture materials such as blood clots or thrombus, the Thrombus Capture Guide 11 retracts by pulling the Capture Pullwire 10 proximally while push/pull Capture Catheter 12 to axially lengthen the ALTC Device 8 over the thrombus without substantially decreasing the device diameter. As needed, advancing the Capture Catheter shaft 12 distally while pulling the Capture Pullwire will allow the ALTC Device 8 to axially lengthen to capture the thrombus. Furthermore, the expandable Funnel Tip 9 of the Suction Catheter 2 (or the funnel tip of the expanding guide catheter) can be positioned at the proximal end of the occluded area to support and minimized thrombus movement. This maneuver continues until all thrombus is inside the ALTC Device 8. Once the thrombus is completely within the ALTC Device 8, pulling the ALTC Device 8 away from the occluded area can restore immediate blood flow while containing the thrombus inside the ALTC Device 8.

In some embodiments, the capture catheter shaft 12 and the guidewire tube 6 are configured to be positioned side-by-side adjacent (e.g., offset and not coaxial, and not passing within the opening 802 or other radially expanded portion of the tubular mesh 6) to the ALTC Device 8 and capture guide (shown, for example, in FIGS. 49A and 49B). Also illustrated is the dynamic fold point 88, reserve radially compressed segment 81 and compressed end at 128 fixed to the outer wall of the guidewire tube 6.

FIGS. 50A-50G illustrate the retrieval of thrombus into the expanding guide catheter wherein the ALTC device lengthens distally and creates additional space and the thrombus is redistributed and enable better retrieval into the expanding guide catheter. The funnel tip 52 and expanding section 53 of the expanding guide catheter also facilitate the ease of thrombus retrieval. For example, when the ALTC Device (e.g., tubular mesh 8) captures the blood clot inside, the ALTC Device 8 can advantageously stretch axially and compress radially beyond its working length (e.g., when the reserve radially compressed segment has been completely expanded, and/or by distal advance of the guidewire tube 6), effectively squeezing the blood clot radially to decrease its diameter/width. Fresh blood clots are typically soft and deformable. Applying axial stretching to the ALTC device can squeeze out the fluid that is within the blood clot, thereby reducing the size of blood clot and allowing blood clots to be removed from the vascular system more easily. The ability of the ALTC Device to lengthen dynamically also provides another clinically effective way to remove the large clot burden by redistributing the volume of blood clot or thrombus, as shown, for example, in FIG. 50A-50G. For example, with respect to current interventional devices such as filters and baskets, when blood clots or thrombus is collected and retrieved into a catheter such as a guiding catheter or sheath, the blood clot or thrombus can gather together or pooled at base of the filter or basket into a large "ball-like" shape and prevent the large "ball-like" thrombus to enter the lumen of the guiding catheter or sheath. A similar effect can occur when aspiration/suction is attempted using a smaller inner diameter guide catheter. However, the ALTC device can lengthen serially from the distal end to create additional length and space within the ALTC Device (as shown, for example, in FIGS. 50B, 50D, and 50F). By lengthening the ALTC Device's distal end, the blood clot or thrombus is redistributed within the ALTC device thereby reducing the ball-like size of the blood clot, thrombus, or other material for better retrievable inside the guiding catheter lumen (FIGS. 50C, 50E, 50G). These steps can be repeated for about or at least about 2, 3, 4, 5, or more cycles until all the blood clot and thrombus is retrieved in the catheter in a compacted form. Furthermore, the use of an expanding guide catheter with an expandable distal section in concert with the ALTC device can allow more efficient blood clot or thrombus removal, as illustrated, for example, in FIGS. 50A and 50C. The effectiveness of the ALTC Device 8 can be further demonstrated in an extreme vascular condition where there is minimal to no distal space available for conventional thrombectomy catheters to fully axially expand in order to be functional. The distal space beyond the distal end of the thrombectomy system can be in some cases less than about 3 cm, 2 cm, 1 cm, 5 mm, or less. In other words, the ALTC Device 8 can be delivered in a first, radially compressed configuration, and compressed by the outer sheath. Upon removal of the outer sheath, the ALTC Device 8 can transform into a radially expanded configuration and configured to capture thromboemboli even though the device may be in an axially compressed configuration. The ALTC Device 8 can then be axially expanded, such as, for example, at least about 1.25×, 1.5×, 2×, 2.5×, 3×, 3.5×, 4×, 4.5×, 5×, 5.5×, 6×, 6.5×, 7×, 8×, 9×, 10×, or more with respect to its fully functional axially compressed length while still maintaining a constant or substantially constant radially expanded diameter through a working range, such as between about 1 cm and about 50 cm, between about 1 cm and about 20 cm, between about 1 cm and about 10 cm, between about 1 cm and about 5 cm, or between about 1 cm and about 3 cm in some embodiments. In some embodiments, the ALTC device 8 has an open proximal end during delivery, and/or throughout its working axial length. The Thrombus Capture Guide 11 can advantageously deploy initially in the tight space while the ALTC device body remains inside the Capture Catheter shaft 12. Subsequently, the Thrombus Capture Guide retracts proximally to begin deploying the ALTC Device 8. The potential axially expanded length of the ALTC Device 8 is not necessarily limited and in some embodiments could extend to the entire length of the catheter system. The ALTC Device 8 can be collapsed and contained within the Capture Catheter shaft 12 and Outer Sheath 1 during introduction into the vasculature and expands when the Outer Sheath 1 retracts proximally to deploy the ALTC Device 8. The Capture Catheter shaft 12 can be made from suitable materials such as and not limit to Nylon, Polyurethane, Pebax, Polyethylene, PET, PTFE, ePTFE, PEEK, polypropylene. It is also advantageous and possible in some embodiments that the Capture Catheter shaft 12 is deflectable at various locations and multiple deflectable directions along the shaft length to accommodate various tortuous paths such as entry into the right atrium, right ventricle, main pulmonary artery, left and right pulmonary artery as previously described.

Figure 51:
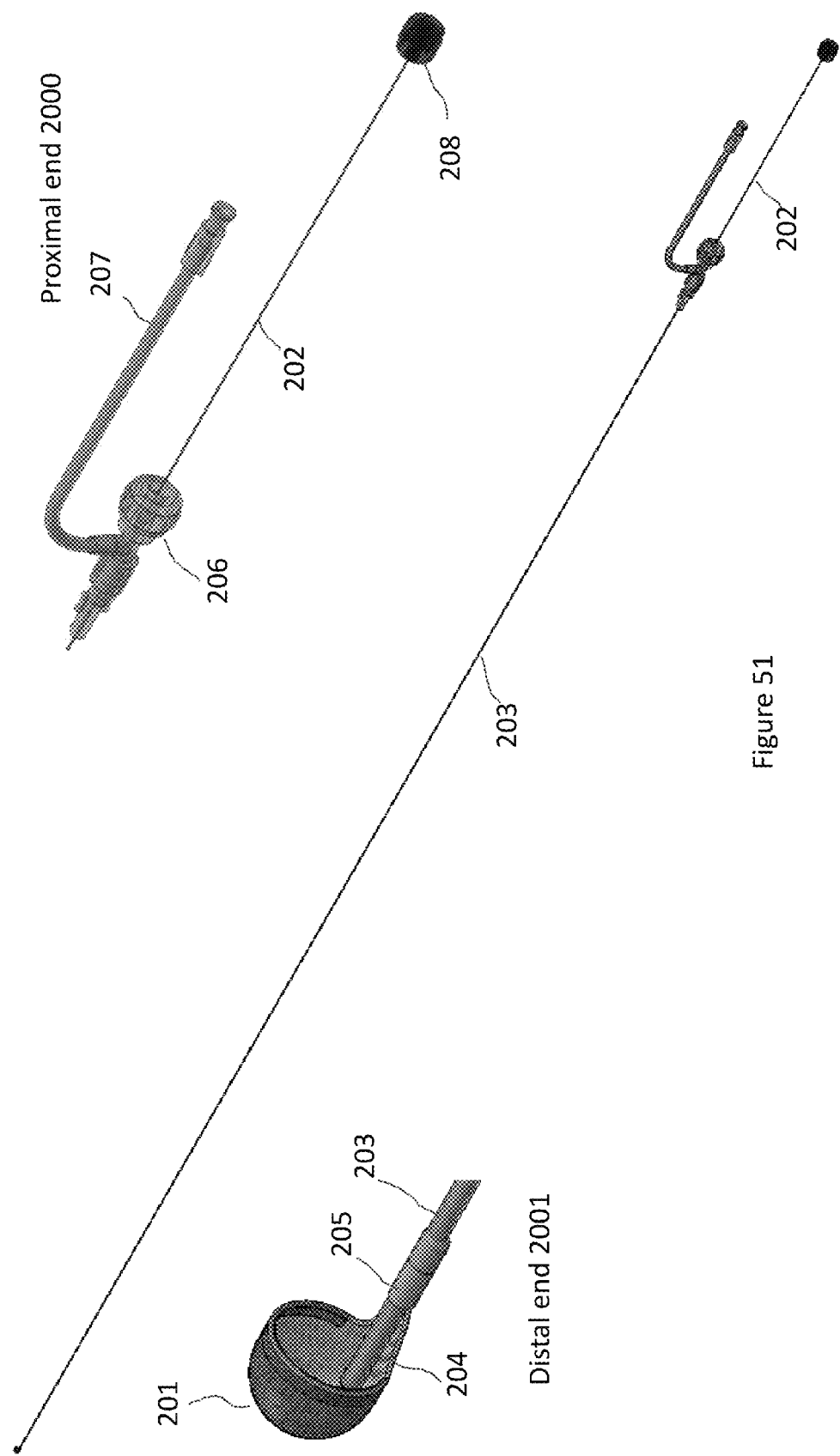
FIG. 51 illustrates an embodiment of a system for removing blood clots.

A perspective view of another embodiment of a capture system is shown in FIG. 51. FIG. 51 also illustrates non-limiting examples of various possible elements that can be included in a material capture system, according to some embodiments of the invention. As illustrated in FIG. 51, included in some embodiments are any number of, such as one, two, or more of the following components: a thrombus capturing device or ALTC device 201 having any of the features described herein, e.g., a pusher wire or inner pusher 202, a first tubular member such as an outer sheath 203, a loop or capture guide 204, and a coupler 205. The ALTC device 201 can attach to the capture guide 204. In some embodiments, the capture guide 204 comprises a metallic material, such as Nitinol. The capture guide 204 can be in the form of, for example, a loop, as shown, or any closed shape including an oval, ellipse, or polygon. The capture guide 204 can be in the form of an open shape such as any linear or non-linear segment. The ALTC device 201 and the capture guide 204 can be coupled such as being sutured together. The ALTC device 201 and the capture guide 204 can be encapsulated in a low durometer polymeric material. The capture guide 204 can be coupled to the outer sheath 203 via the coupler 205. The proximal end of the ALTC device 201 (not shown) can be coupled to the inner pusher 202.

The outer sheath 203 can, in some embodiments, be an elongate tubular member with a central lumen therethrough, and have a proximal end 2000 and a distal end 2001, both shown in FIG. 51. The distal end 2001 of the outer sheath 203 can be operably connected to a capture device (e.g., tubular mesh as described herein), which can be movably axially with respect to the outer sheath 203. The proximal end 2000 can include any number of, such as one, two, or more of the following components: a hemostasis assembly 206, a flush port 207, and a collapsed segment 208. The outer sheath 203 extends proximally and can be coupled to the hemostasis assembly 206. The inner pusher 202 extends proximally and can be coupled to a luer. In some embodiments, the inner pusher 202 can have a lumen to allow passage of a guidewire. In some embodiments, the inner pusher 202 is a solid shaft.

Figure 52:
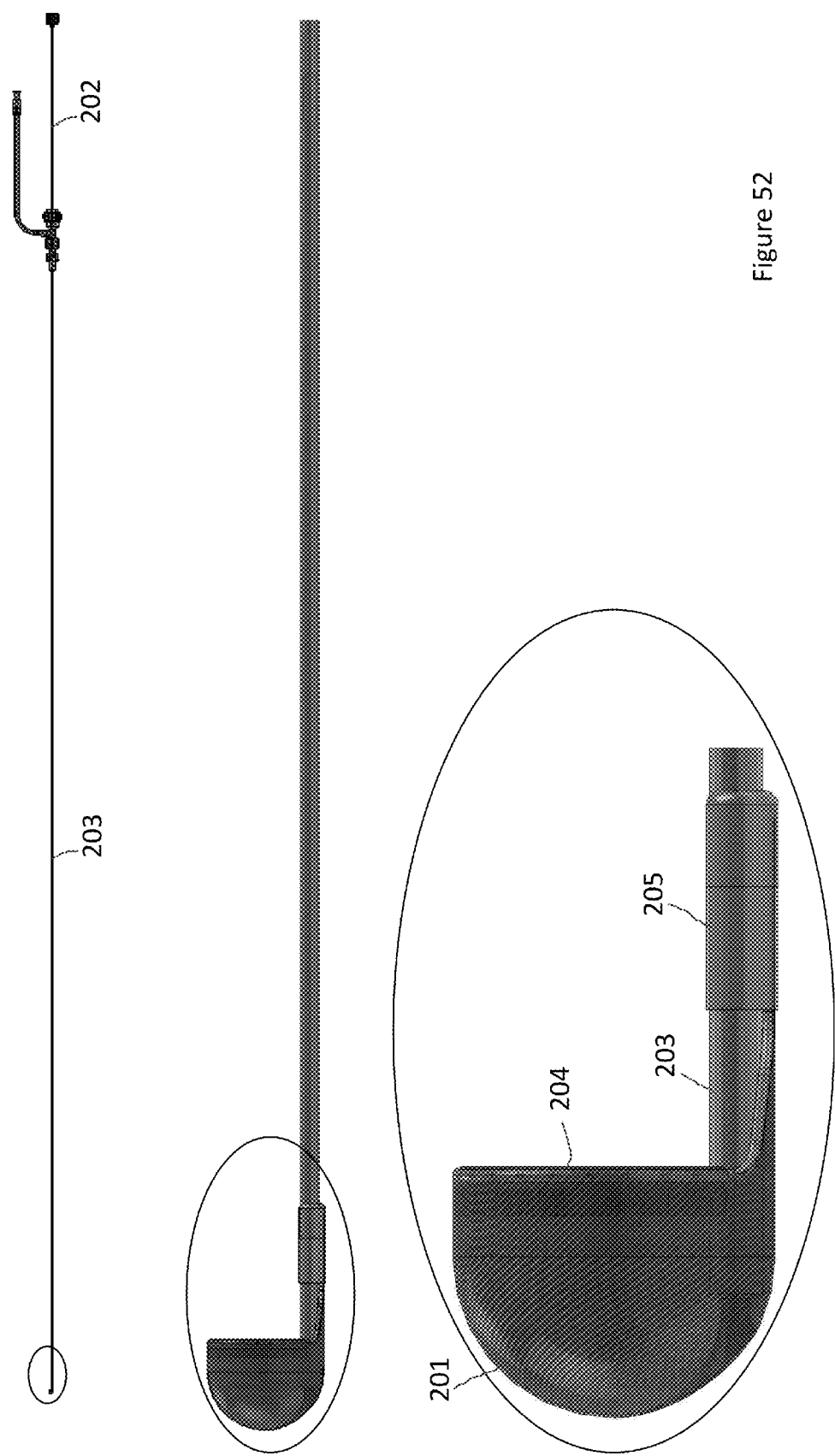
FIG. 52 illustrates the distal end of the capture device of the system of FIG. 51 in the deployed configuration.

FIG. 52 shows the distal end 2001 of the ALTC device 201 in a deployed configuration. In some embodiments, the ALTC device 201 in the initial deployed configuration has a low profile. A portion of the ALTC device 201 is extended while the remaining length of the ALTC device 201 is collapsed and contained within the outer sheath 203 as previously described. In some methods of use, the ALTC device 201 can be collapsed and tracked through a sheath or guide catheter (not shown) to the intended treatment area. In some embodiments, the guide catheter can be retracted proximally to initially deploy the ALTC device 201 and the capture guide 204. For instance, the retraction of the guide catheter can cause the capture guide 204 to expand. The capture guide 204 can include a compressed or constrained configuration while within the guide catheter. During the initial deployment, the capture guide 204 is released from a constrained position to a neutral position. In the neutral position, the capture guide 204 creates a perimeter for the ALTC device 201. In the case of a loop or other circular configuration, the capture guide 204 can create a constant diameter. In the case of other shapes or configurations, the capture guide 204 can create a constant cross-section. Alternatively or in combination, in other methods of use, the ALTC device 201 can be advanced distally from the guide catheter to deploy the ALTC device 201.

In some cases, only a small fractional portion of the ALTC device 201, such as less than about 50%, 45%, 40%, 35%, 30%, 25%, 20%, 15%, 10%, 5%, or less of the axial length of the device can be initially deployed and fully functional. The small portion can correspond to an amount of the ALTC device 201 which allows the capture guide 204 to assume the neutral position. During the deployment of the capture guide 204, a length of the ALTC device 201 can be retained within the outer sheath 203. The ALTC device 201 can follow a curve from the capture guide 204 to the outer sheath 203. Retracting the outer sheath 203 can lengthen the ALTC device 201 while maintaining a constant diameter or cross-section provided by the capture guide 204.

FIG. 53 illustrates an embodiment of an ALTC device 201 in the initially deployed configuration. As illustrated in FIG. 53, the ALTC device 201 can be in some embodiments a generally tubular structure, and in some cases a net-like mesh structure that is collapsible within the outer sheath 203. The ALTC device 201 is expandable to the diameter or cross-section provided by the capture guide 204. The ALTC device 201 can be axially lengthened or shortened, such as within a working range, by releasing the ALTC device 201 from the outer sheath 203. The ALTC device 201 can be axially lengthened or shortened while maintaining or substantially maintaining the diameter or cross-section provided by the capture guide 204. The ALTC device 201 can be deployed to form a generally tubular or cylindrical shape of varying axial lengths. The ALTC device 201 can be axially lengthened or shortened to retrieve and capture foreign or otherwise unwanted materials within the body, including the vascular system such as blood clots, thrombus and/or foreign materials. In some embodiments, an outer sheath is not present and a loader can be utilized to prepare the ALTC device 201 for delivery in a low crossing-profile configuration.

As shown, for example, in FIGS. 54 and 55, the ALTC device 201 can be axially lengthened. FIG. 54 illustrates the ALTC device 201 in a second configuration. The ALTC device 201 is in the second configuration wherein the deployed and expanded ALTC device 201 is longer than the initial deployed configuration in the axial direction. The remaining collapsed ALTC device 201 length resides inside the outer sheath 203 and is shorter than the initial deployed configuration. The outer sheath 203 can be retracted to axially lengthen the ALTC device 201. As the outer sheath 203 is retracted, the capture guide 204 is retracted since the capture guide 204 is coupled to the outer sheath 203 via the coupler 205. As the capture guide 204 is retracted, the ALTC device 201 is advance from the collapsed portion 208 to the expanded portion. The outer sheath 203 can be retracted proximally to axially lengthen the ALTC device 201. Alternatively or in combination, in other methods of use, the capture guide 204 can be retracted to axially lengthen the ALTC device 201, such as be retracting the outer sheath 203. The diameter or cross-section of the ALTC device 201 can remain constant or substantially constant between the initial deployed configuration and the second configuration.

Alternatively or in combination, in other methods of use, the inner pusher 202 is advanced distally to advance the proximal end of the ALTC device 201. As described herein, the proximal end of the ALTC device 201 is coupled to the inner pusher 202. In the second configuration, the inner pusher 202 is advanced distally to release a portion of ALTC device 201 from the outer sheath 203.

FIG. 55 illustrates an embodiment of an ALTC device 201 in a third configuration. The ALTC device 201 is in the third configuration wherein the deployed and expanded ALTC device 201 is longer than the second configuration in the axial direction. The remaining collapsed ALTC device 201 length resides inside the outer sheath 203 and is shorter than the second configuration. The outer sheath 203 can be retracted proximally to axially lengthen the ALTC device 201. The diameter or cross-section of the ALTC device 201 can remain constant or substantially constant between the second configuration and the third configuration. Alternatively or in combination, in other methods of use, in the third configuration, the inner pusher 202 is advanced distally to a greater extent. In the third configuration, the inner pusher 202 is advanced distally to release a longer portion of ALTC device 201 from the outer sheath 203.

FIG. 56 illustrates an embodiment of the material capture, e.g., basket mesh element 209. The basket mesh element 209 can be a component of the ALTC device 201. The basket mesh element 209 can be a structural mesh that provides an appropriate shape as described herein. The basket mesh element 209 can comprise Nitinol or other materials. The basket element can be braided, weave, wireform or laser cut. The basket mesh element 209 can include a first end that couples to the capture guide 204. The basket mesh element 209 can be coupled to the capture guide 204 via a suture or other mechanical means including welding, clips, flanges, adhesive, lamination, etc. The basket mesh element 209 and the capture guide 204 can be encapsulated within a low durometer polymeric material. The second end of the basket mesh element 209 can be coupled to the inner pusher 202. The second end can be folded inward to couple to the inner pusher 202. The second end can be inverted to couple to the inner pusher 202. The second end 202 can form a tube within a tube configuration of the ALTC device 201.

FIG. 57 illustrates an embodiment of the ALTC device 201. The ALTC device 201 has an expanded portion when the ALTC device 201 is deployed (e.g., initial deployed configuration, second configuration, third configuration, etc.). The expanded portion has a constant diameter or cross-section as described herein. The expanded portion, or a portion thereof, is coupled to the capture guide 204. The expanded portion is coupled to the outer sheath 203 via the capture guide 204 and the coupler 205. The ALTC device 201 has a collapsed portion 208. The collapsed portion 208 can reside within the lumen of the outer sheath 203. The collapsed portion 208 can be retained within the outer sheath 203 when the expanded portion is in the deployed configuration. The collapsed portion 208, or a portion thereof, can be coupled to the inner pusher 202. The collapsed portion 208 is everted as shown. During axial lengthening of the ALTC device 201, a portion of the collapsed portion 208 can roll-out at a distal region to transition between the collapsed portion 208 and the expanded portion.

FIGS. 58A and 58B illustrate embodiments of the capture guide 204.

FIG. 58A illustrates the capture guide 204. FIG. 58B illustrates the capture guide 244, which can include any of the features of capture guide 204. The capture guide 204 can form a continuous shape. The capture guide 204 can include leg elements 210. The leg elements 210 can transition the capture guide 204 from an axial direction to a perimeter shape. The perimeter shape can be circular as shown in FIG. 58A. The capture guide 204 can form a continuous loop. The capture guide 244 can include a non-continuous perimeter. As shown in FIG. 58B, the capture guide 244 can include a non-continuous loop. The capture guide 204, 244 can be made of a metallic material. In some embodiments, the capture guide 204, 244 is formed of a shape-memory material. In some embodiments, the capture guide 204, 244 is formed from Nitinol. The capture guide 204, 244 can be formed of a spring-like material such as a metal. The capture guide 204, 244 can be circular, elliptical, semi-circular, or any combination thereof. The capture guide 204, 244 can include a pre-shaped curve. The pre-shaped curve can be formed during the manufacturing of the capture guide 204, 244. The pre-shaped curve can be a neutral or expanded shape of the capture guide 204, 244. Upon release of a constraint, the capture guide 204, 244 will assume the pre-shaped curve. The capture guide 204, 244 can have any curved shape. The capture guide 204, 244 can have a single radius of curvature or multiple portions having different radii of curvature. The capture guide 204, 244 can be considered spring loaded based in part of the material and the shape of the capture guide 204, 244. In some embodiments, the anchors can include non-continuous shapes, such as hooks with sharp or atraumatic segments or tips in some cases.

The capture guide 204, 244 can have two or more leg elements 210. The leg elements 210 can be adjacent or adjoining within the guide catheter during delivery. The leg elements 210 can be relatively parallel or side-by-side during delivery in the collapsed configuration. The collapsed leg elements 210 can define a different diameter or cross-section as compared to the fully expanded or neutral configuration of the capture guide 204, 244. In some embodiments, the collapsed leg elements 210 enable the capture guide 204, 244 to have a smaller diameter or cross-section while collapsed within the guide catheter. For example, when the capture guide 204, 244 is fully expanded, the circular portion of the capture guide 204, 244 defines a diameter. For non-circular capture guide 204, 244, the capture guide 204, 244 can define a cross-section when fully expanded. Upon collapsing the leg elements 210, the circular portion of the capture guide 204, 244 defines a diameter that is smaller than the previous expanded configuration. The capture guide 204 can comprise one segment as shown in FIG. 58A with two ends that form a continuous loop configuration. The capture guide 244 can comprise multiple segments as shown in FIG. 58B and form a non-continuous loop.

During expansion, the leg elements 210 can bias the capture guide 204, 244 outward to assume the neutral configuration of the capture guide 204, 244. The leg elements 210 can be positioned at an angle relative to each other in the neutral configuration of the capture guide 204, 244. The leg elements 210 can include one or more bends to facilitate folding of the capture guide 204, 244. The one or more bends can enable the capture guide 204, 244 to fold in a low profile configuration along the longitudinal axis of the guide catheter.

Figure 59:
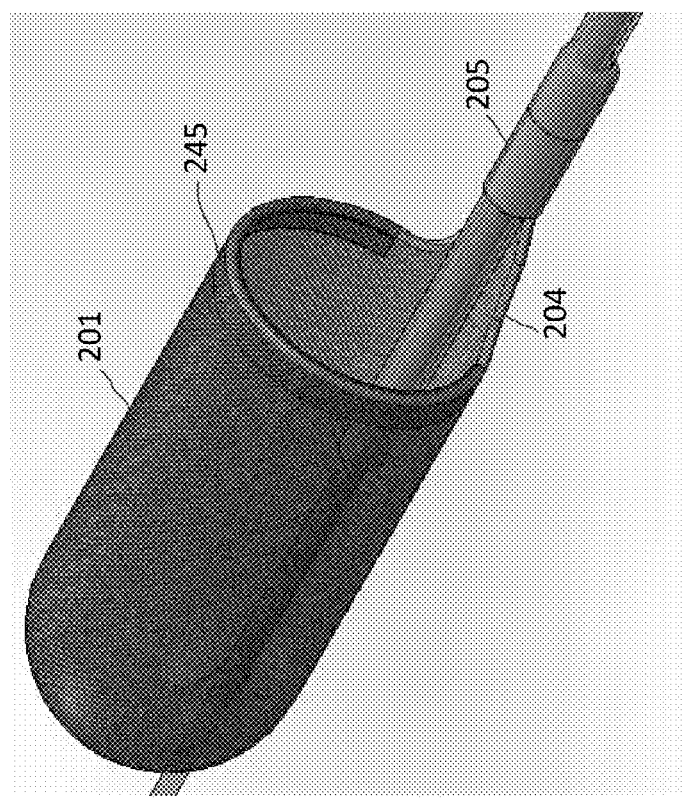
FIG. 59 illustrates a view of a capture device opening for a system for neuro thrombus.

FIG. 59 shows one aspect of the opening of the ALTC device 201. The end of the ALTC device 201, or a portion thereof, attaches to the capture guide 204. While the capture guide 204 is shown in FIG. 59, any capture guide or feature thereof can be coupled to the end of the ALTC device 201. The end of the ALTC device 201 and the capture guide 204 form an assembly. The assembly can be encapsulated within a low durometer polymeric material to form a polymeric coating or ring 245. The polymeric coating can encapsulate the assembly completely or a portion thereof. In the illustrated embodiment, the polymeric coating encapsulates a portion of the end of the ALTC device 201 and the capture guide 204. The polymeric coating can encapsulate the rounded portion of the capture guide 204 having a constant or substantially constant diameter. The polymeric coating can encapsulate the entire ALTC device 201, or any portion thereof. The area where the polymeric coating is void/not present can allow for easy movement. For instance, the area between the leg elements can be void. The void area can facilitate collapse of the capture guide 204. In some embodiments, the polymeric coating can be selectively applied. In some embodiments, the polymeric coating can form a ring or a portion of a ring. The polymeric coating can be applied to the outside of the material capture element, e.g., basket mesh element 208. The polymeric coating can be applied to the inside of the basket mesh element 208. The polymeric coating can be applied to the entire basket mesh element 208 to encapsulate the basket mesh element 208.

Figure 60:
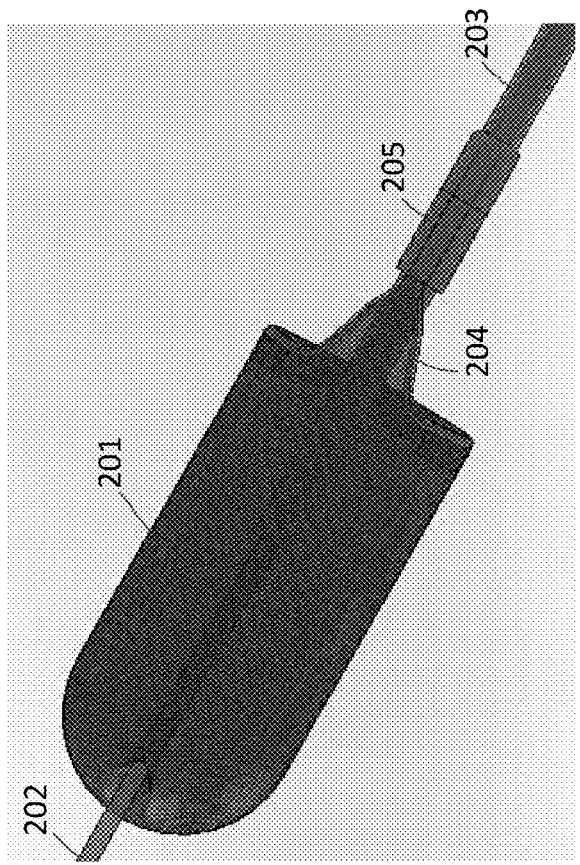
FIG. 60 illustrates another view of a capture device opening of FIG. 59.

FIG. 60 shows one aspect of the opening of the ALTC device 201. The ALTC device 201 can include a central, longitudinal axis. The outer sheath 203 can include a longitudinal axis. The inner pusher 202 can extend along the longitudinal axis of the outer sheath 203. The central, longitudinal axis of the ALTC device 201 can be offset from the longitudinal axis of the outer sheath 203. The central, longitudinal axis of the ALTC device 201 can be offset from the longitudinal axis of the inner pusher 202. The capture guide 204 can define the offset. For instance, the central, longitudinal axis of the ALTC device 201 can include the central point of the circle created by the capture guide 204. The central point of the capture guide 204 can be offset from the outer sheath 203. As described herein, the end of the ALTC device 201 is coupled to the inner pusher 202. The ALTC device 201 axially lengthens by releasing a portion of the ALTC device 201 from the outer sheath 203. The ALTC device 201 that is released follows a portion of the inner pusher 202 as shown in FIG. 59. The released portion of the ALTC device 201 curves outward and assumes the diameter of the capture guide 204. The ALTC device 201 can form an everted shape with a portion of the ALTC device 201 collapsed near the inner pusher 202 and a portion of the ALTC device 201 expanded to the diameter or cross-section of the capture guide 204. In some embodiments, the shape of the ALTC device 201 can resemble a tube within a tube. In some embodiments, the ALTC device 201 can be considered telescoping.

A perspective view of another system is shown in FIG. 61. FIG. 62 shows the proximal end of the system and FIG. 63 shows the distal end of the system. FIG. 64 shows a subassembly of the system. FIGS. 61-64 also illustrates non-limiting examples of various possible elements that can be included in a material capture system, according to some embodiments of the invention. As illustrated in FIG. 61, included in some embodiments are any number of, such as one, two, or more of the following components: an anchor assembly 221, a corewire and basket assembly 222, an anchor and pusher assembly 223, a proximal catheter assembly 224, and a distal catheter assembly 225. The anchor assembly 221 can include about or at least about one, two, three, four, five, or more anchors 241 configured to secure a clot. The anchor and pusher assembly 223 includes one or more anchors 241 and the anchor pusher 240. The anchors can be coupled to the pusher as described herein. The corewire and basket assembly 222 can include a corewire 242 and the ALTC device 201. The proximal catheter assembly 224 can include a shaft with one, two, or more lumens, e.g., the dual lumen shaft 243. FIG. 61 illustrates a dual lumen shaft 243 of the system. The dual lumen shaft 243 can be attached to the hemostasis housing 206 described herein. The dual lumen shaft 243 can be coupled to the capture guide 204 via the coupling 205. The illustrated embodiment shows a dual lumen shaft, but other configurations are contemplated. In some embodiments, the shaft has a single lumen. In some embodiments, the shaft is a multi-lumen shaft. The shaft can have about or more than about one lumen, two lumens, three lumens, four lumens, five lumens, six lumens, seven lumens, etc.

FIG. 62 illustrates the proximal end of the system including the corewire and basket assembly 222, the anchor and pusher assembly 223, and the proximal catheter assembly 224. The corewire and basket assembly 222 and the anchor and pusher assembly 223 can reside in separate lumens of the dual lumen shaft 243. The system can include the corewire 242. The corewire 242 can include any of the features or function as the inner pusher 202. The corewire 242 can be coupled to a pusher lock 246. The anchor pusher 240 can extend through the pusher lock 246. The pusher lock 246 can be movable along the shaft of the anchor pusher 240. In some embodiments, the pusher lock 246 can limit the expansion of the anchors 241. In some embodiments, the pusher lock 246 can provide a tactile response when the anchors 241 are deployed by abutting the anchor and pusher assembly 223 with the pusher lock 246.

FIG. 63 illustrates the distal catheter assembly 225. The distal catheter assembly 225 can include any of the features described herein. The distal catheter assembly 225 can include the ALTC device 201. The distal catheter assembly 225 can include the coupler 205 between the outer shaft 203 and the capture guide 204.

FIG. 64 illustrates the anchor assembly 221. The anchor assembly 221 can comprise one or more anchors 241. The anchor assembly 221 can comprise about or at least about one anchor, two anchors, three anchors, four anchors, five anchors, six anchors, seven anchors, eight anchors, nine anchors, ten anchors, or more than ten anchors 241. The illustrated embodiment shows three anchors, but other configurations are contemplated. The anchor assembly 221 can include the anchor pusher 240. The anchor pusher 240 can include an elongate member comprising a shaft. The anchor pusher 240 can be extended proximally within the dual lumen shaft 243. The anchor pusher 240, or a portion thereof, can pass proximally through the proximal catheter assembly 224. The anchor pusher 240, or a portion thereof, can pass proximally through the pusher lock 246. The anchor pusher 240, or a portion thereof, can be connected to the luer hub. The anchor assembly 221 can be contained in the dual lumen shaft 243. The one or more anchors 241 can be coupled at a distal end of the anchor pusher 240. The one or more anchors 241 can be one anchor or a plurality of anchors 241. The anchors can be connected to the anchor pusher 240 in series, and regularly or irregularly spaced apart. In some embodiment, the diameter of the anchor 241 when expanded is smaller than the diameter of the capture guide 204 when expanded. In some embodiment, the diameter of the anchor 241 when expanded is smaller than the ALTC device 201 when expanded. The anchor 241 can be designed to fit within the ALTC device 201 when the ALTC device 201 is expanded. In some embodiments, the anchors can form symmetric or asymmetric loop shapes to circumscribe and stabilize a portion of the clot. In some embodiments, the anchors can be an mesh or braided element. In some embodiments, the anchor can be a balloon. In some embodiment, there can be a combination of braided mesh and balloon. In some embodiments, the anchors 241 can have a portion that extend radially outwardly from the elongate member in which they are attached.

Figure 65:
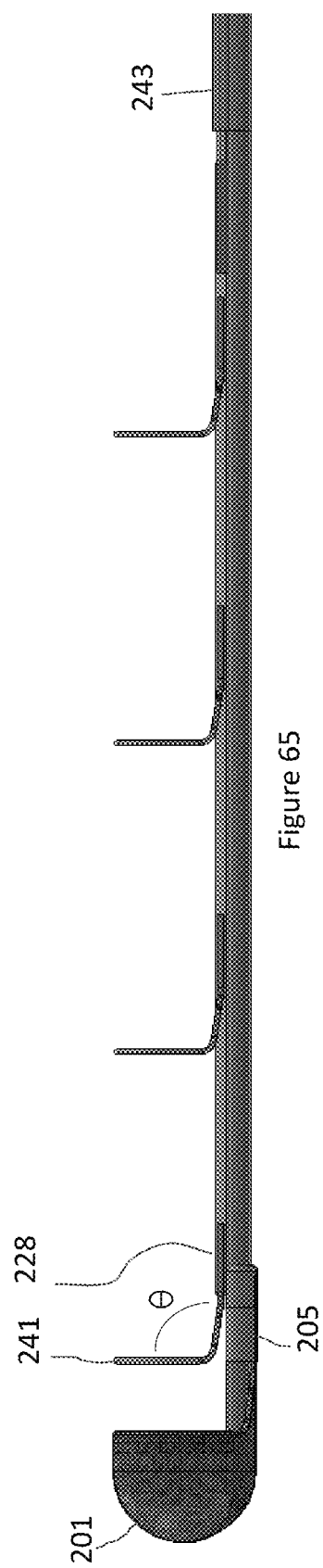
FIG. 65 illustrates a side view of a distal end of the capture device and anchors of the system of FIG. 61.

FIG. 65 illustrates a side view of the distal end of the ALTC device 201 and the anchors 241. The anchors 241 can include or be similar to any of the features of capture guide 204, 244 described herein. Each anchor 241 can form a continuous shape, or a discontinuous shape in other embodiments. Each anchor 241 can include leg elements 228. The leg elements 228 can transition the anchor 241 from an axial direction to a perimeter shape. The perimeter shape can be circular as shown in FIG. 64. The anchor 241 can form a continuous loop. The anchor 241 can include a non-continuous perimeter such as a non-continuous loop. The anchor 241 can be made of a metallic material. In some embodiments, the anchor 241 is formed of a shape-memory metal such as Nitinol. The anchor 241 can be circular, elliptical, semi-circular, or any combination thereof. Each anchor 241 can include a pre-shaped curve. Two or more anchors 241 can have the same pre-shaped curve. Two or more anchors 241 can have a different pre-shaped curve. The pre-shaped curve can be formed during the manufacturing of the anchors 241. The pre-shaped curve can be a neutral or expanded shape of the anchors 241. Upon release of a constraint, the anchors 241 can assume the pre-shaped curve. The pre-shaped curve of the anchors 241 can be similar to the pre-shaped curve of the capture guide 204. The anchors 241 can have a different radius of curvature from the capture guide 204. As described herein, the anchors 241 can have a smaller diameter than the capture guide 204. Alternatively, the anchors can have the same or larger diameter than the capture guide. In some embodiments, the anchors include barbed elements to attach to a clot. In some embodiments, the anchors are atraumatic and do not include any barbed or other sharp surfaces.

The anchor 241 can have two or more leg elements 228. The leg elements 228 can be adjacent or adjoining within the guide catheter during delivery, and relatively parallel to the. The leg elements 228 can be relatively parallel or side-by-side during delivery in the collapsed configuration. The collapsed leg elements 228 can define a different diameter or cross-section as compared to the fully expanded or neutral configuration of the anchor 241. In some embodiments, the collapsed leg elements 228 allow the anchor 241 to have a smaller diameter or cross-section while collapsed within the guide catheter. For example, when the anchor 241 is fully expanded, the circular portion of the anchor 241 defines a diameter. For non-circular anchors 241, the anchor 241 can define a cross-section when fully expanded. Upon collapsing the leg elements, the circular portion of the anchor 241 defines a diameter that is smaller than the previous expanded configuration. The anchor 241 can comprise one segment as shown in FIG. 64 that forms a continuous loop configuration. The anchor 241 can comprise multiple segments similar to capture guide 244 shown in FIG. 58B. The anchors 241 have a outwardly curving shape relative to the two or more leg elements 228.

The anchor 241 can include an expanded position as shown in FIG. 65. In the case of a shape memory material the expanded position can be a neutral position of the material. The anchor 241 can be configured to fold or bend during delivery. The anchor 241 can assume a low-profile configuration during delivery. The expanded anchor 241 can have any shape including round, circular, elliptical, etc. The anchors 241 expand to their pre-formed shape upon removal of a constraint, such as outer sheath 203, delivery catheter, or other constraining structure.

The expanded position of an anchor 241 can be defined by angle theta θ. In some embodiments, the angle theta is measured from the leg element 228 to the circular portion of the anchor 241. In some embodiments, the angle theta is measured from the horizontal to the vertical extension of the anchor 241. In some embodiments, the angle theta is measured from the dual lumen shaft 243 to the expanded portion of the anchor 241. In some embodiments, the angle theta determines the vertical or substantially vertical orientation of the anchor 241. Each anchor 241 of a plurality of anchors 241 can have the same angle theta. If the anchors 241 are arranged in a series, the angle theta can be uniformly the same. Two or more anchors 241 can have the same angle theta, or angles that are within about 30, 25, 20, 15, 10, 5, 4, 3, 2, 1, or less degrees of each other.

Each anchor 241 of a plurality of anchors 241 can have a different angle theta. Two or more anchors 241 can have the different angle theta. If the anchors 241 are arranged in a series, the series of anchors 241 can also have different variations in the angle theta. For example, the first anchor 241 can have a first angle theta such as about or at least about 45 degrees, such as between about 0 and 90 degrees, between about 15 and 75 degrees, or between about 30 and 60 degrees in some cases. The next or immediately adjacent anchor 241 can have a second angle theta such as 135 degrees. The next or immediately adjacent anchor 241 can have a third angle theta such as 45 degrees. The series can continue to alternate between 45 degrees and 135 degrees or other desired angles. In some embodiments, the series of anchors can have different diameter.

In some embodiments, two or more anchors 241 can form a mirror image. In some embodiments, two or more anchors 241, 241 can extend from the dual lumen shaft 243 such that the circular portion of one anchor 241 substantially projects onto the circular portion of the other anchor 241. In some embodiments, two or more anchors 241 can be identical or substantially identical in orientation. In some embodiments, two or more anchors 241 can be coaxial. In some embodiments, two or more anchors 241 have different orientations relative to the dual lumen shaft 243. In some embodiments, two or more anchors 241 are not coaxial. In some embodiments, a first anchor 241 has a first axis extending through the circular portion of the first anchor 241 and the second anchor 241 has a second axis extending through the circular portion of the second anchor 241. In some embodiments, the first axis and the second axis can be skewed. In some embodiments, the first axis and the second axis are perpendicular. In some embodiments, the first axis and the second axis are parallel. In some embodiments, the first axis and the second axis are coaxial.

In some embodiments, the angle theta can range from 5 degrees to 175 degrees. Examples of the angle theta include 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, etc., and ranges incorporating any two of the aforementioned values. Examples of the angle theta can be in the range of 0-20 degrees, 20-40 degrees, 40-60 degrees, 60-80 degrees, 80-100 degrees, 100-120 degrees, 120-140 degrees, 140-160 degrees, 160-180 degrees, etc. In some embodiments, the angle theta can be approximately 90 degrees. In such embodiment, the anchor 241 can be approximately vertical relative to the dual lumen shaft 243. In some embodiments, the angle theta can be approximately 45 degrees. In such embodiment, the anchor 241 can form an acute angle relative to the dual lumen shaft 243. In some embodiments, the angle theta can be approximately 135 degrees. In such embodiment, the anchor 241 can form an obtuse angle relative to the dual lumen shaft 243.

The anchor and pusher assembly 223, or a portion thereof, can be moved within the dual lumen shaft 243. In some embodiments, the anchor and pusher assembly 223 can be moved coaxially within a lumen of the dual lumen shaft 243. The anchor and pusher assembly 223 can be moved independently from the corewire and basket assembly 222. In some embodiments, the anchor and pusher assembly 223 can be moved simultaneously with the corewire and basket assembly 222. In some embodiments, the anchor and pusher assembly 223 can be advanced distally or proximally relative to the dual lumen shaft 243. In some embodiments, the anchor and pusher assembly 223 does not impact the movement of the ALTC device 201. The one or more anchors 241 can be moved independently of the ALTC device 201. As described herein, the one or more anchors 241 can be moved relative to a stationary ALTC device 201. As described herein, the ALTC device 201 can be moved relative to a stationary anchor 241.

Figure 66:
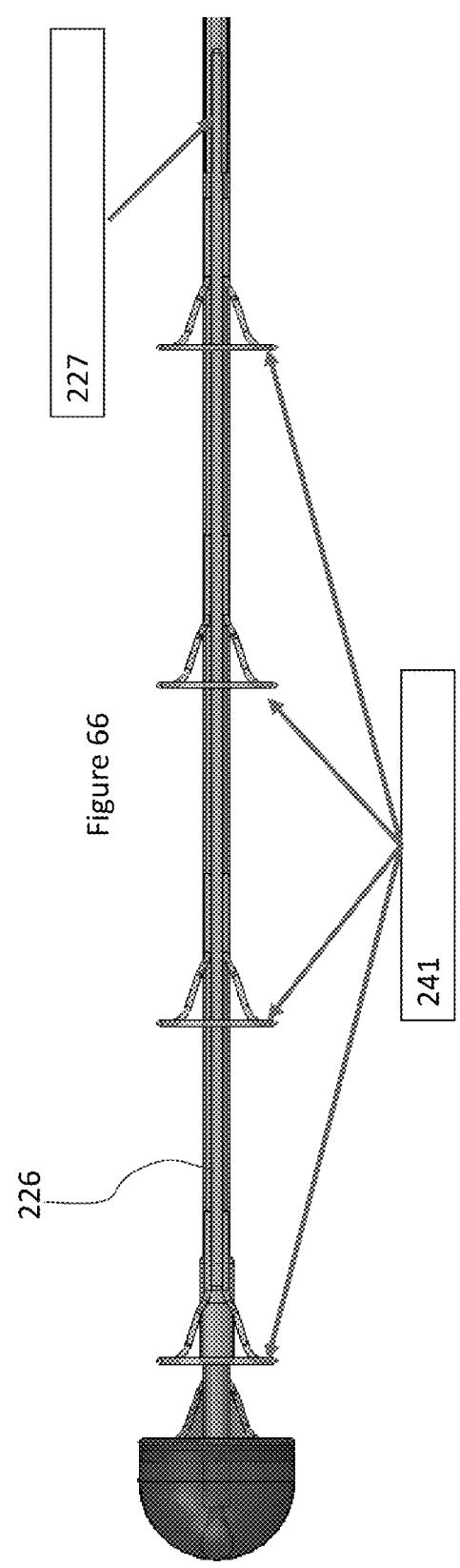
FIG. 66 illustrates a top view of a distal end of the capture device and anchors of the system of FIG. 61.

FIG. 66 illustrates a top view of the distal end of the ALTC device 201 and the anchors 241. The one or more anchors 241 can be coupled to a distal pusher 226. In some embodiments, the leg extensions 228 of the anchors 241 are coupled to the distal pusher 226. In some embodiments, the angle theta is measured from the distal pusher 226 to the expanded portion of the anchor 241. In the illustrated embodiment, each anchor 241 is coupled to the distal pusher 226. The movement of the distal pusher 226 causes simultaneous movement of all anchors 241 coupled thereto. In alternative embodiments, two or more distal pushers 226 are provided. Each of the two or more distal pushers 226 controls the movement of one or more anchors 241. The two or more distal pushers 226 can move independently such that two or more anchors 241 can move independently. Other configurations are contemplated. The distal pusher 226 can be coupled to a crescent pusher 227. In some embodiments, the crescent pusher 227 can provide rigidity to the distal pusher 226. The distal pusher 226 and the crescent pusher 227 can be affixed via welding, adhesive, mechanical interference, etc.

Figure 67:
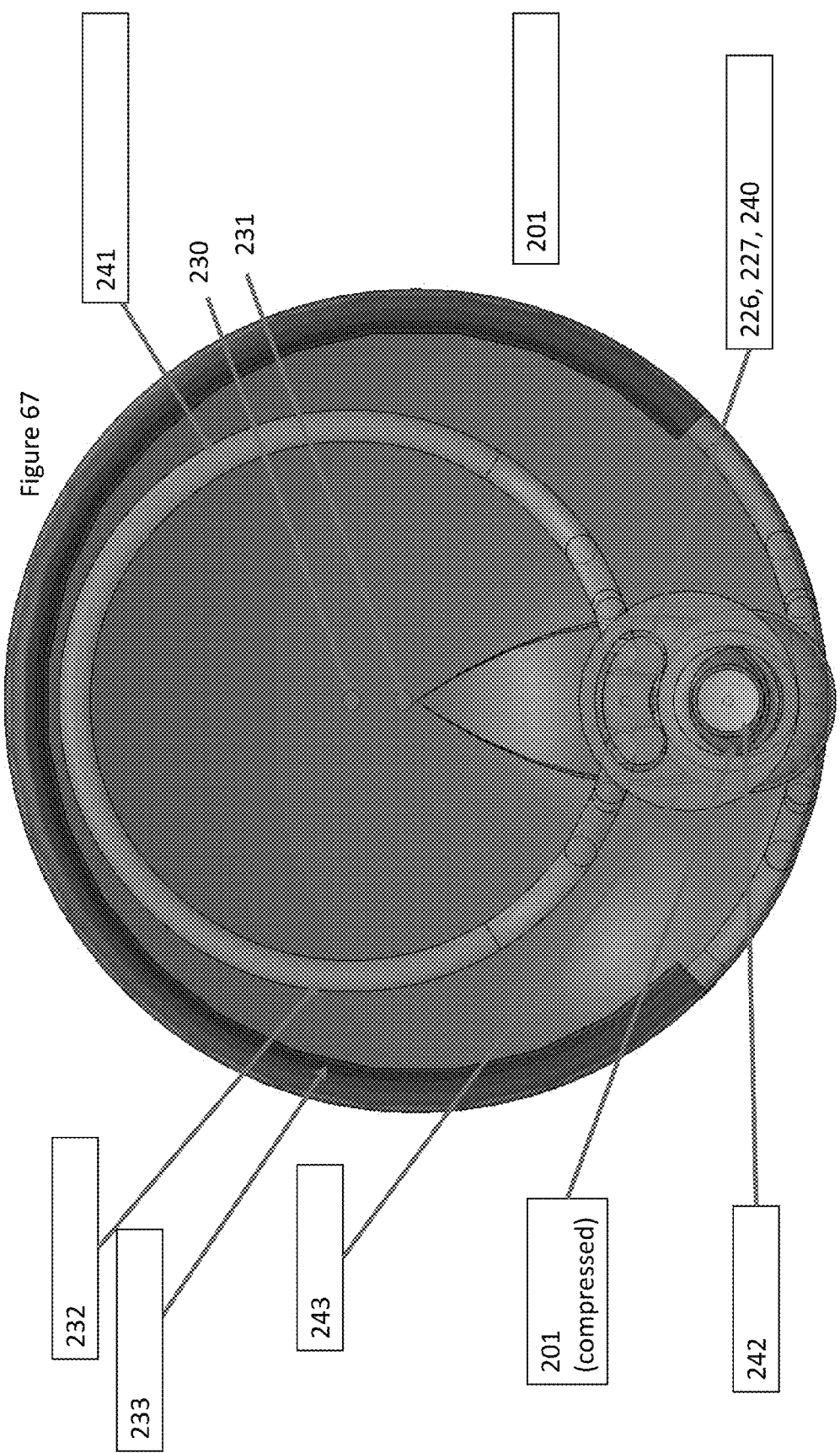
FIG. 67 illustrates a front view of a distal end of the capture device of the system of FIG. 61.

FIG. 67 illustrates a front view of the distal end of the ALTC device 201 and the anchors 241. The dual lumen shaft 243 is shown in cross section. In some embodiments, the dual lumen shaft 243 provides a lumen for the anchor and pusher assembly 223 and a lumen for the corewire and basket assembly 222. The two lumens can be separated such that movement of one assembly does not impact the movement of the other assembly. Other configurations are contemplated.

The corewire and basket assembly 222 includes the corewire 242. The corewire 242 is shown disposed in one lumen of the dual lumen shaft 243. The corewire 242 can include any of the feature or functions of the inner pusher 202 described herein. The compressed basket or compressed ALTC device 201 is disposed in the same lumen of the dual lumen shaft 243 as the corewire 242. The compressed ALTC device 201 can have any of the features or function as the collapsed segment 208 described herein. The outer shaft of the dual lumen shaft 243 is shown.

The anchor and pusher assembly 223 can include the distal pusher 226 and the crescent pusher 227 described herein. The crescent pusher 227 can be coupled to the anchor pusher 240, described herein. In some embodiments, the distal pusher 226, the crescent pusher 227, and the anchor pusher 240 are integrally or monolithically formed. In some embodiments, the distal pusher 226 is a portion of the anchor pusher 240. The crescent shape of the crescent pusher 227 may prevent rotation of the crescent pusher 227 within the dual lumen shaft 243. The crescent pusher 227 is shown a lumen of the dual lumen shaft 243.

The anchors 241 can be coupled to the anchor pusher 240, such that movement of the anchor pusher 240 causes movement of the one or more anchors 241. The anchors 241 can be coupled to the distal pusher 226, such that movement of the distal pusher 226 causes movement of the one or more anchors 241. In some embodiments, the anchors 241 can be welded to the distal pusher 226. The anchors 241 are arranged such that the anchors 241 are coaxial along central longitudinal axis 230. As shown in the illustrated embodiment, only one anchor is visible from the front view due to the coaxial nature of the anchors 241.

The ALTC device 201 is expanded as shown in FIG. 67. The outer diameter 232 of the anchor 241 can be smaller than the inner diameter 233 of the basket or ALTC device 201 in order for the ALTC device 201 to capture the anchors 241. The ALTC device 201 can capture one or more anchors depending on the axial length of the ALTC device 201. The axial length of the ALTC device 201 is adjustable based on the release of the ALTC device 201 from the dual lumen shaft 243. As a longer portion of the ALTC device 201 is released, the ALTC device 201 axially lengthens. As described herein, the ALTC device 201 remains at a constant diameter or cross-section as the ALTC device 201 lengthens. The capture guide 204 maintains the shape of the expanded ALTC device 201 as the ALTC device 201 axially lengthens. The capture guide 204 is smaller in diameter than the outer diameter 232 of the anchor 241.

The capture guide 204 can function as a centering device to center the system within the vessel. The capture guide 204 can be a similar diameter or cross-sectional shape as the vessel. In some methods of use, the capture guide 204 is smaller than the diameter of the blood vessel when the capture guide 204 is expanded. In some methods of use, the capture guide 204 is approximately equal to the diameter of the blood vessel when the capture guide 204 is expanded. In some methods of use, the ALTC device 201 is smaller than the diameter of the blood vessel when the ALTC device 201 is expanded. In some methods of use, the ALTC device 201 is approximately equal to the diameter of the blood vessel when the ALTC device 201 is expanded. In some methods of use, the ALTC device 201 contacts the vessel wall of the blood vessel. In some methods of use, the ALTC device 201 does not contact the vessel wall.

The capture guide 204 can include the central longitudinal axis 231. In some embodiments, the dual lumen shaft 243 can be offset from the central longitudinal axis 231. In some embodiments, the dual lumen shaft 243 can be coaxial with the central longitudinal axis 231 (not shown). The anchor 241 can include the central longitudinal axis 230. In some embodiments, the dual lumen shaft 243 can be offset from the central longitudinal axis 230. In some embodiments, the dual lumen shaft 243 can be coaxial with the central longitudinal axis 230 (not shown). In some embodiments, the central longitudinal axis 230 of the anchor 241 can be offset from the central longitudinal axis 231 of the capture guide 204. In some embodiments, the central longitudinal axis 230 of the anchor 241 can be coaxial with the central longitudinal axis 231 of the capture guide 204 (not shown). In some embodiments, the dual lumen shaft 243 can be positioned near an edge of the capture guide 203. Other configurations are contemplated.

FIGS. 68A-69C illustrate capture of a clot within a vessel, according to some embodiments. FIG. 68A illustrates the ALTC device 201 in the initially deployed configuration. As illustrated in FIG. 68A, the ALTC device 201 can be in some embodiments a generally semi-spherical mesh structure when initially deployed. The mesh structure is initially collapsible within a guide catheter or outer sheath 203. The guide catheter delivers the ALTC device 201 to the desired location within the body of the patient. The capture guide 204 is released from the constrained condition within the guide catheter or outer sheath 203. The capture guide 204 expands to have a cross-sectional shape. In some embodiments, the capture guide expands to a round or circular shape.

The ALTC device 201 is expandable to the diameter or cross-section provided by the capture guide 204. In some methods of use the ALTC device 201 is expanded by removal of a constraint. The ALTC device 201 can be released from a guide catheter. The guide catheter can be retracted to allow the capture guide 204 to expand. In some methods of use, the ALTC device 201 can be released from within the dual lumen shaft 243 by retraction of the dual lumen shaft. As described herein, one end portion of the ALTC device 201 is coupled to the capture guide 204. The ALTC device 201 can include a tubular mesh with a distal end. The ALTC device 201 can include a dynamic fold point as described herein such that the tubular mesh becomes everted upon release from the dual lumen shaft 243. The ALTC device 201 can include a reserve radially compressed segment within the dual lumen shaft terminating proximally at a point coupled to the inner pusher 202. In some methods of use, the expanded segment of the ALTC device 201 is positioned distal to the blood clot. The outer sheath 203 is positioned proximally, within, or adjacent to the blood clot.

FIG. 68B shows the ALTC device 201 in the initially deployed configuration. As described herein, the corewire and basket assembly and the anchor and pusher assembly can be independently actuated. The first anchor 241 can be released when the outer sheath 203 retracts proximally. The first anchor 241 can include a shape memory material such that the first anchor 241 assumes an expanded configuration. The first anchor 241 can expand such that the first anchor 241 is defined by the angle theta. The first anchor 241 expands from a low profile configuration to an expanded configuration. The low profile configuration can enable the anchor 241 to reside within the outer sheath 203 during delivery. In some additionally or alternative methods of use, the first anchor 241 can be released when the anchor pusher 240 advances distally.

The released anchor can be firmly secured to the clot. In some methods of use, the first anchor 241 can become entangled in the clot. In some methods of use, the first anchor 241 can reside against the clot. In some methods of use, the first anchor 241 can be designed to push the clot. In some methods of use, the first anchor 241 can be designed to perform a sweeping motion through the clot. The sweeping motion can be over an arc of the angle theta, or a portion thereof. The sweeping motion can break the clot, or a portion thereof.

FIG. 68C shows the ALTC device 201 in the initially deployed configuration. The second anchor 241 can be released when the outer sheath 203 retracts proximally. In some methods of use, the second anchor 241 can be released when the anchor pusher 240 advances distally. The second anchor 241 can include a shape memory material such that the second anchor 241 assumes an expanded configuration. The second anchor 241 can expand such that the second anchor 241 is defined by the angle theta. As described herein, the first anchor 241 and the second anchor 241 can have the same or different orientation for the angle theta.

FIG. 68D shows the ALTC device 201 in the initially deployed configuration. In some methods of use, the third anchor 241 can be released when the outer sheath 203 retracts proximally. In additional or alternative embodiments, the third anchor 241 can be released when the anchor pusher 240 is advanced distally. The third anchor 241 can include a shape memory material such that the third anchor assumes an expanded configuration. The third anchor 241 can expand such that the third anchor 241 is defined by the angle theta. As described herein, the first anchor 241, the second anchor 241 and the third anchor 241 can have the same or different orientation for the angle theta.

The first anchor 241, the second anchor 241 and the third anchor 241 can be designed to be secured to the clot. The arrangement of the anchors 241 can be designed to facilitate engagement with the clot. For instance, the number of anchors, the spacing of the anchors, the cross-section dimension of the anchors, the shape of the anchors, the orientation of the anchors relative to the anchor pusher, the angle theta, the shape of the leg extension, the rapidness of the shape memory material to assume the neutral shape, the stiffness of the material, as well as other factors can be optimized to facilitate engagement of the anchors 241 with the clot.

The ALTC device 201 and the anchors 241 can retract proximally to remove the clot. In some methods of use, the ALTC device 201 can catch emboli or debris that dislodges during removal of the clot. In some methods of use, the ALTC device 201 is positioned downstream in a vessel to catch debris. The curved distal end of the ALTC device 201 can function as a net. In some methods of use, the anchors 241 can disrupt the clot to enable easier removal of the clot. In some methods of use, the sweeping motion of deploying the anchors 241 can break apart the clot.

FIGS. 69A-69C illustrates the axial lengthening sequence of the ALTC device 201, according to some embodiments. The dual lumen sheath 243 can be retracted to axially lengthen the ALTC device 201. As the dual lumen sheath 243 is retracted, the capture guide 204 is retracted since the capture guide 204 is coupled to the dual lumen sheath 243 via the coupler 205. As the capture guide 204 is retracted, the collapsed portion 208 becomes the expanded portion. The dual lumen sheath 243 can be retracted proximally to axially lengthen the ALTC device 201. Alternatively or in combination, in other methods of use, the capture guide 204 can be retracted to axially lengthen the ALTC device 201, such as be retracting the dual lumen sheath 243. The diameter or cross-section of the ALTC device 201 remains constant between the initial deployed configuration shown in FIG. 69A and the expanded configurations shown in 69B and 69C. In additional or alternative methods of use, the corewire 242 can be actuated to axially lengthen the ALTC device 201. The corewire 242 can be positioned within the dual lumen shaft 243. Actuation of the corewire 242 such as axially in the appropriate direction will release the constrained portion of the ALTC device 201. The movement of the corewire 242 can result in axial lengthening or shortening of the ALTC device 201.

FIG. 69A illustrates the system after deployment of the anchors 241. In some methods of use, the anchors 241 are deployed before axial lengthening of the ALTC device 201. In some methods of use, one or more steps of releasing an anchor and axially lengthening can occur in any order. In some methods of use, the first anchor is deployed and then the ALTC device 201 is axially lengthened to cover the first anchor. In some methods of use, the first and second anchors are deployed before the ALTC device 201 is axially lengthened to cover the first anchor or the second anchor. In some methods of use, the first, second, and third anchors are deployed before the ALTC device 201 is axially lengthened to cover the first anchor, the second anchor, or the third anchor. In some embodiments, two or more steps can occur simultaneously. In some methods of use, the first anchor is deployed and the ALTC device 201 is axially lengthened to cover the first anchor simultaneously. In some methods of use, the first and second anchor are deployed and the ALTC device 201 is axially lengthened to cover either the first anchor or the second anchor simultaneously. In some methods of use, the first, second, and third anchors are deployed and the ALTC device 201 is axially lengthened to cover the first anchor, the second anchor, or the third anchor simultaneously.

FIG. 69B illustrates the axial lengthening of the expanded portion of the ALTC device 201. The ALTC device 201 is lengthening proximally to capture the clot secured by the first anchor 241. The compressed or constrained segment of the ALTC device 201 is shortening within the dual lumen shaft 243 reciprocally. The dual lumen sheath 243 can be retracted to axially lengthen the ALTC device 201, as described herein. The ALTC device 201 can encapsulate the first anchor 241. The first anchor 241 can be sized to fit within the ALTC device 201 once the ALTC device 201 is axially lengthened.

FIG. 69C illustrates the axial lengthening of the expanded portion of the ALTC device 201. The ALTC device 201 is lengthening proximally to capture the clot secured by the first anchor 241, the second anchor 241, and the third anchor 241. The compressed or constrained segment of the ALTC device 201 is shortening within the dual lumen shaft 243 reciprocally. FIG. 69C illustrates the axial lengthening ALTC device 201 is sufficient to completely capture the clot. The ALTC device 201 and the anchors 241 can retract proximally to remove the clot.

The ALTC device 201 can be axially lengthened, such as within a working range, by releasing the ALTC device 201 from the sheath, which can have one, two, or more lumens in the sheath 243. The ALTC device 201 can be axially lengthened or shortened while maintaining or substantially maintaining the diameter or cross-section provided by the capture guide 204. The ALTC device 201 can be axially lengthened or shortened to retrieve and capture foreign or otherwise unwanted materials within the body, including the neurovascular system such as blood clots, thrombus and/or foreign materials.

The ALTC device 201 described herein can be sized to fit within a vessel of the neurovascular system, including any vessel noted elsewhere herein. As one example, the ALTC device 201 can be used to treat arteries, veins, and non-vascular lumens or regions. In some embodiments, the device can be configured to treat cerebral venous sinus thrombosis and cavernous sinus thrombosis. A thrombus, commonly called a clot, is the product of blood coagulation due to aggregated platelets and red blood cells connected by a fibrin protein to block a blood vessel. The thrombus can travel (embolize), such as propagating toward the heart, lungs or other organs. The removal of thrombus can reduce the risk of a stroke, myocardial infarction, and/or pulmonary embolisms. The ALTC device 201 can lengthen to have a maximal length that covers the entire length of anchors 241, e.g., from about 0.01 mm to about 100 mm. Depending on vessel diameter, the outer diameter of the ALTC device 201 can range from, in some embodiments, from about 0.01 millimeter up to about 10 millimeters. The diameter of the ALTC device can achieve the similar effect of reducing or stretching the ALTC device diameter. In some embodiments, suction is not utilized or required, and the ALTC device envelops the clot, which can be mechanically pulled back into the capture catheter. In some embodiments, the mechanical thrombectomy systems and methods as disclosed herein can be used in combination with, and/or coated with a therapeutic agent such as, for example, one or more anti-thrombotic or anti-platelet agents such as heparin, hirudin, warfarin, dabigatran, and/or enoxaparin; tPA, streptokinase, or urokinase, an anti-proliferative agent such as paclitaxel (Taxol), rapamycin (Sirolimus), zotarolimus, or tacrolimus; and the like depending on the desired clinical result.

Figure 70B:
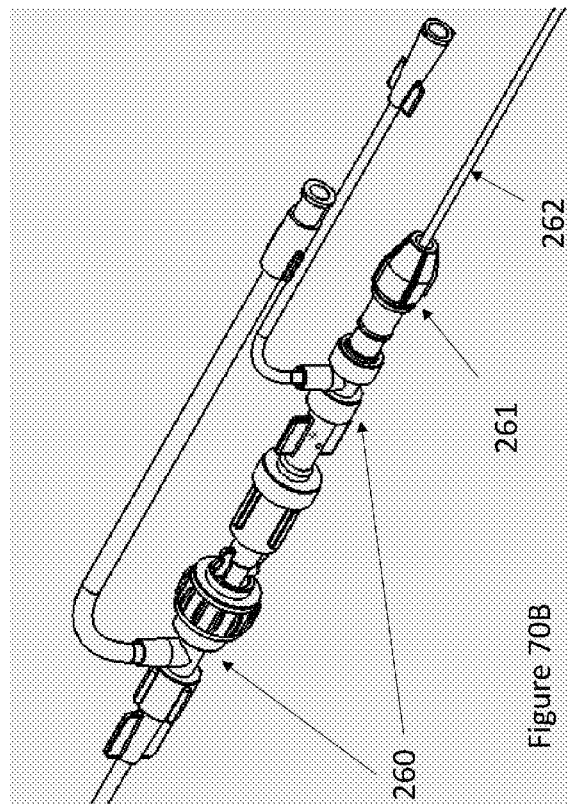
FIGS. 70A and 70B illustrate views of an embodiment of a pusher lock system.
Figure 70A:
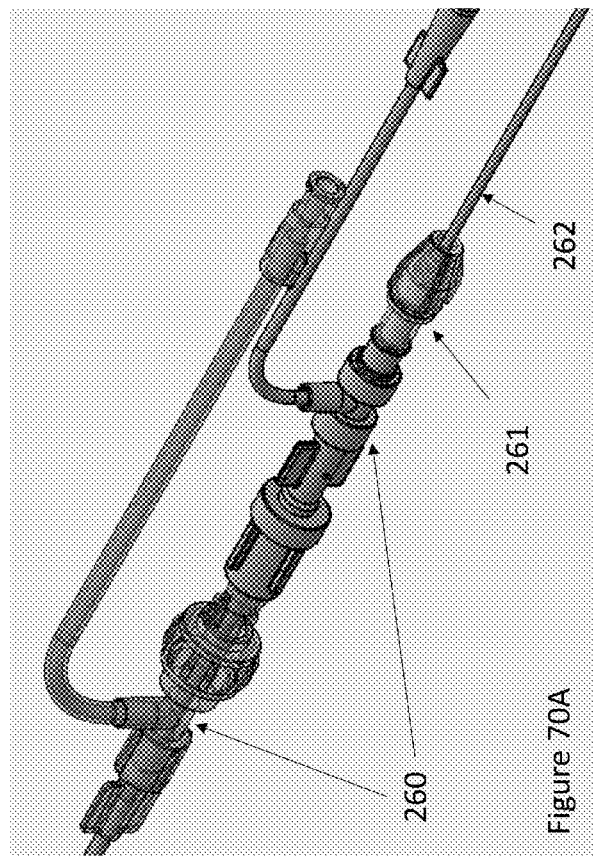
Figure 71C:
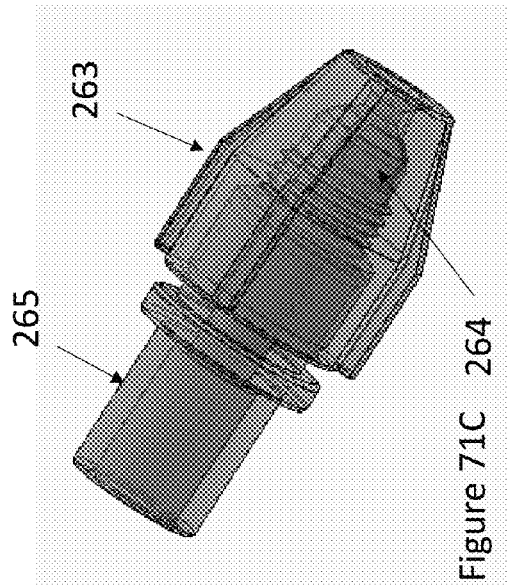
FIGS. 71A-71D illustrate views of a pusher lock of the pusher lock system of FIG. 70A.
Figure 71D:
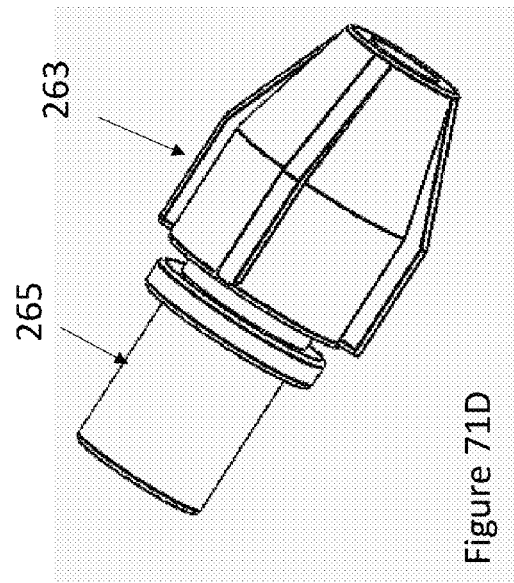
Figure 71A:
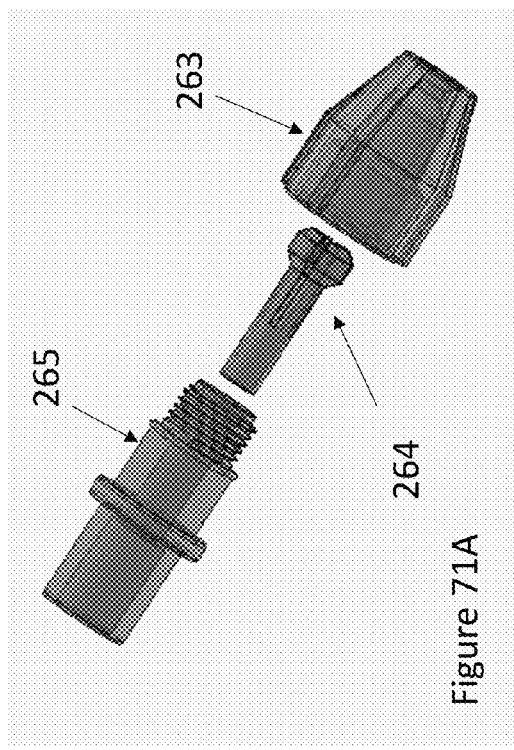
Figure 71B:
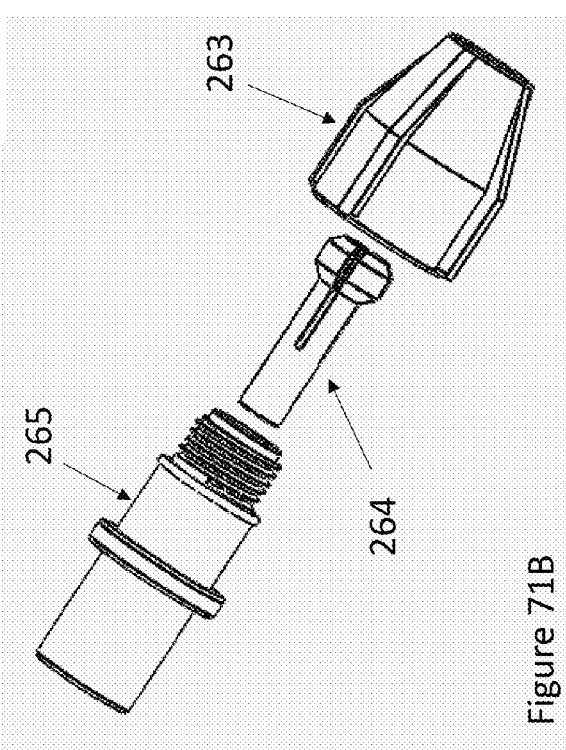

FIGS. 70A and 70B illustrate views of an embodiment of a pusher lock system. The pusher lock system can be utilized with any of the system described herein. FIG. 70A also illustrates non-limiting examples of various possible elements that can be included in a material capture system, according to some embodiments of the invention. As illustrated in FIG. 70A, included in some embodiments are any number of, such as one, two, or more of the following components: a hemostasis seal 260, a pusher lock 261, and a pusher 262. The hemostasis seal 260 can include a plurality of seals at spaced apart locations in the pusher lock system. The hemostasis seal 260 can be similar to the seals shown in FIGS. 21E and 21F. The pusher lock 261 can include any of the features of pusher lock 246 described herein. The pusher 262 can include any of the features of the inner pusher 202.

The pusher 262 can include any of the features of the corewire 242 described herein. The pusher 262 can include any of the features of the anchor pusher 240 described herein.

Referring first to the system shown in FIGS. 70A-B, the pusher 262 can include any of the features of the inner pusher 202 described herein. The pusher 262 can extend from the proximal end to the distal end. In some embodiments, the pusher extends from the nosetip of the catheter to the proximal end. In some embodiments, the pusher 262 is a single shaft. In some embodiments, the pusher 262 comprises one or more subcomponents. The pusher 262 can include an inner guidewire lumen shaft extending from the distal end toward the proximal end. The pusher 262 can include a pusher tube extending from the proximal end. The inner guidewire lumen shaft can be attached to a pusher tube to form a unitary structure. Other configurations are contemplated. The pusher 262 can comprise any material suitable to axially lengthen the ALTC device 201, as described herein. In some embodiments, the pusher 262 or a component thereof, comprises a metal such as stainless steel or titanium. In some embodiments, pusher tube can comprise stainless steel.

The pusher 262 can be positioned coaxially within a shaft. In some embodiments, the pusher 262 is placed within a middle shaft. The guidewire lumen shaft and the pusher tube assembly are positioned coaxially within the middle shaft. The pusher tube is extended beyond the middle shaft. The pusher tube can slide coaxially with respect to the middle shaft to either lengthen or shorten the ALTC device 201. During clinical use, if there is no locking mechanism for the pusher 262, the user can inadvertently actuate the pusher tube or the middle shaft prematurely, which will deploy the ALTC device 201. The pusher lock 261 helps to secure the pusher tube to the middle shaft during insertion of the catheter. The pusher lock 261 can be unlocked after unsheathing the ALTC device 201. The pusher lock 261 can be unlocked when the user is ready for lengthening the ALTC device 201.

In some alternative and additionally embodiments, the guidewire lumen shaft and the pusher tube assembly are positioned coaxially within the outer sheath 203. The pusher tube is extended beyond the outer sheath 203. The pusher tube can slide coaxially with respect to the outer sheath 203 to either lengthen or shorten the ALTC device 201. In some embodiments, the pusher tube extends beyond the outer sheath 203, as shown in FIG. 51. During clinical use, if there is no locking mechanism for the pusher 252, the user can inadvertently actuate the pusher tube or the outer sheath 203 prematurely, which will deploy the ALTC device 201. The pusher lock 251 helps to secure the pusher tube to the outer sheath 203 during insertion of the catheter. The pusher lock 261 can be unlocked after unsheathing the ALTC device 201. The pusher lock 261 can be unlocked when the user is ready for lengthening the ALTC device 201.

Referring now to the system shown in FIG. 62, the pusher 262 can include any of the features of the corewire 242 described herein. The pusher 262 can include any of the features of the anchor pusher 240 described herein. The pusher 262 can extend from the proximal end to the distal end. The pusher 262 can include an inner guidewire lumen shaft extending from the distal end toward the proximal end. The pusher 262 can include a pusher tube extending from the proximal end. Other configurations are contemplated.

The pusher 262 is positioned coaxially within a shaft. In some embodiments, the pusher 262 is placed within a middle shaft of the dual lumen shaft 243. The guidewire lumen shaft and the pusher tube assembly are positioned coaxially within the middle shaft. The pusher tube is extended beyond the middle shaft. The pusher tube can slide coaxially with respect to the middle shaft to either lengthen or shorten the ALTC device 201. During clinical use, if there is no locking mechanism for the pusher 262, the user can inadvertently actuate the pusher tube or the middle shaft of the dual lumen shaft 243 prematurely, which will deploy the ALTC device 201. The pusher lock 261 helps to secure the pusher tube to the middle shaft during insertion of the catheter. The pusher lock 261 can be unlocked after unsheathing the ALTC device 201. The pusher lock 261 can be unlocked when the user is ready for lengthening the ALTC device 201.

In some alternative or additional embodiments, the pusher 262 is placed within an upper shaft of the dual lumen shaft 243. The guidewire lumen shaft and the pusher tube assembly are positioned coaxially within the upper shaft. The pusher tube is extended beyond the upper shaft. The pusher tube can slide coaxially with respect to the upper shaft to deploy the anchors 241. During clinical use, if there is no locking mechanism for the pusher 262, the user can inadvertently actuate the pusher tube or the dual lumen shaft 243 prematurely, which will deploy the anchors 241. The pusher lock 261 helps to secure the pusher tube to the dual lumen shaft 243 after during insertion of the catheter. The pusher lock 261 can be unlocked after unsheathing the ALTC device 201. The pusher lock 261 can be unlocked after unsheathing the first anchor 241. The pusher lock 261 can be unlocked when the user is ready to deploy the anchors 241.

The method can include one or more of the following steps in any order. The delivery catheter can be prepared. The delivery catheter can be prepared at the bedside of a patient. The delivery catheter can be prepared according to one or more instructions. In some methods of use, the pusher lock 261 can be locked in position. The pusher lock 261 can be locked in position on the pusher 262. In some embodiments, the pusher lock 261 is locked in position by rotating the lock cap 263. In some embodiments, the pusher lock 261 can be locked by rotating clockwise. In some embodiments, the pusher lock 261 can be locked by rotating counterclockwise.

In some methods of use, a guidewire is positioned within a patient. In some methods of use, the inner guidewire lumen shaft of the pusher 262 can be guided over the guidewire. In some methods of use, the pusher tube of the pusher 262 can be guided over the guidewire. In some methods of use, the system is advanced over the guidewire. In some methods of use, the delivery catheter is advanced to the intended area for treatment. In some methods of use, the delivery catheter is retracted. In some methods of use, the outer sheath 203 is retracted to deploy the ALTC device 201.

In some methods of use, the pusher lock 251 is unlocked. In some methods of use, the pusher lock 261 is unlocked by rotating the lock cap 263 counterclockwise. In some methods of use, the pusher lock 261 is unlocked by rotating the lock cap 263 in an opposite direction. Upon unlocking the pusher lock 261, the ALTC device 201 can be lengthened. In some methods of use, the ALTC device is lengthened by axially actuating the middle shaft. In some methods of use, the ALTC device is lengthened by axially actuating the pusher tube. In some methods of use, the ALTC device is lengthened by axially actuating the outer sheath. In some methods of use, the ALTC device is lengthened by axially actuating the dual lumen shaft. The pusher lock 261 can be used to affix the pusher tube to the middle shaft as needed.

FIGS. 71A-71D illustrate views of a pusher lock 261 of the pusher lock system of FIG. 70A. As illustrated in FIG.

71A-71D, included in some embodiments are any number of, such as one, two, or more of the following components: the lock cap 263, a collet 264, and a lock body 265. The lock cap 263 and the lock body can include mating threads. In the illustrated embodiment, the lock cap 263 includes female threads and the lock body 265 includes male threads. The collet 264 is disposed between the lock cap 263 and the lock body 265. The pusher 252, or a portion thereof, is designed to be placed within the collet 264. The pusher 252 can extend through an opening in the lock cap 263, through the collet 264, and through an opening in the lock body 265. The lock cap 263 also includes a ramped surface designed to interact with the collet. As the lock cap 262 is rotated, the collet 264 can be brought into engagement with the ramped surface. Further rotation can cause the collet to collapse or tighten onto the pusher 252. Other configurations are contemplated.

Figure 72:
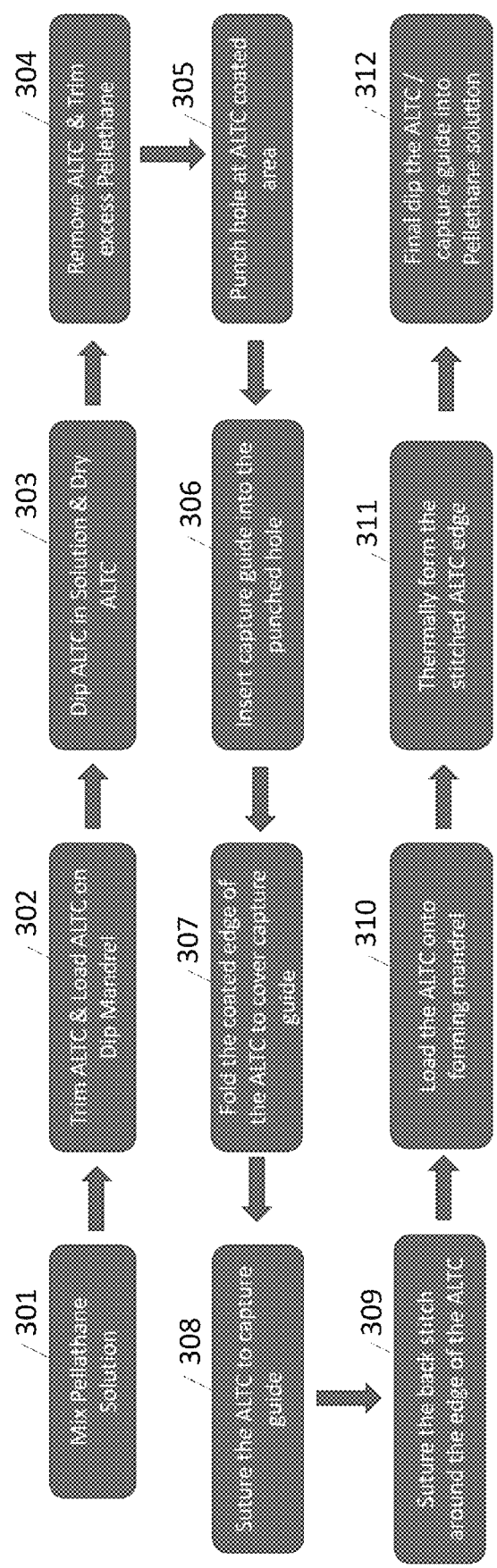
FIG. 72 illustrates a method of assembly an ALTC device to a capture guide.

FIG. 72 illustrates a flow chart of an embodiment of a method 300. In some embodiments, the method can assemble the end of the ALTC device 201 to the capture guide 204. The method can include one or more of the following steps, in any order. The step 301 can include mixing a thermoplastic and/or polyurethane, e.g., Pellethane solution. The solution is mixed using, e.g., a thermoplastic polyurethane, e.g., Pellethane and, e.g., a cyclic ester such as Tetrahydrofuran (THF). The mixture of Pellethane and Tetrahydrofuran (THF) ratio can range from, e.g., between about 1:1 and about 1:20 of Pellethane to THF. The ratio of Pellethane to Tetrahydrofuran can be, for example, about, at least about, or no more than about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1.19; 1:20, or ranges including any two of the aforementioned values. The step 302 can include trimming the ALTC device 201. The end of the ALTC device 201 can be squared trim. The step 302 can include loading the ALTC device 201 on the dipping mandrel. The dipping mandrel can be made of polymeric and/or metallic materials such as HDPE, PTFE, stainless steel, etc. The mandrel can be non-coated or coated to allow ease of manufacturing. The step 303 can include dipping the ALTC device 201 in the solution. The ALTC device mounted on a dipping mandrel is slowly dipped into the Pellethane/THF solution. The step 303 can include drying the ALTC device 201. The ALTC device 201 can hang to allow to dry, or dried using other mechanisms. The step 304 can involve removing the ALTC device 201. The step 304 can involve trimming the excess Pellethane. The dipped end of the ALTC device 201 can encapsulate and fix the wire ends of the basket mesh element 209 from movement. The dipped end can prevent the wire ends of the basket mesh element 209 from being exposed. The ALTC device 201 is removed from the dipping mandrel. The excess Pellethane is trimmed close to the edge of the ALTC device 201.

The step 305 can include punching or otherwise creating one or more apertures in the Pellethane coating. The dipped area of ALTC device 201 can be punched to create holes at predetermine location to allow placement of the capture guide. Other methods of making holes in the coating are contemplated. The step 306 can include inserting the capture guide 204 into the punched hole. The capture guide 204 is inserted into the punched hole. The capture guide 204 can be woven through two or more holes. The capture guide can be threaded from one side of the ALTC device 201 to the other side of the ALTC device 201. The step 307 can include folding the edge of the ALTC device to cover the capture guide 204. The dipped coat edge of the ALTC device 201 is folded to cover the wire loop of the capture guide 204. The folding can protect and prevent the encapsulated wire ends of the basket mesh element 209 from protruding. The step 308 can include suturing the ALTC device 201 and the capture guide 204. The ALTC device 201 is sutured to the capture guide 204 using suture materials. Suture materials can include, for example, PET, PTFE, HMWPE, or other materials known in the art. The step 309 can include suturing around the edge of the ALTC device. The step 309 can include suture the back stitch around the edge.

The step 310 can include loading the ALTC device onto the forming mandrel. When the suturing is completed, the ALTC device 201 in then loaded onto the forming mandrel. The step 311 can include thermally forming the stitched ALTC edge. The step 311 can include thermally forming the stitched ALTC device edge using appropriate heating. The forming mandrel can be either polymeric or metallic materials such as PTFE, stainless steel, etc. The step 312 can include dipping the ALTC device and capture device. The ALTC device and capture device can be dipped in the Pellethane solution from step 301. The ALTC device and capture device can be dipped in another solution. The dipping process can include dipping the ALTC device 201 and capture guide 204 into the Pellethane/THF solution. The dipping can secure the assembly of the ALTC device 201 and capture device 204. The step 312 can include loading the assembly of the ALTC device 201 and capture device 204 onto the dipping mandrel. The dipping mandrel can be the same dipping mandrel of steps 302, 303. The dipping mandrel can be a different mandrel. The dipping mandrel for this step 312 can be made of polymeric and/or metallic materials such as HDPE, PTFE, stainless steel, etc. The mandrel for this step 312 can be non-coated or coated to allow ease of manufacturing. In some methods of use, a film or sheet of material can be used in addition or in place of one or more dipping steps. The film can be an extruded polymeric film. The sheet can be a sheet of low durometer polymer such as pellethane, polyurethane, tecothane, etc. The film or sheet can be used and place over the end of the ALTC device. In some methods of use, a film or sheet of material can be used in addition thermally forming the edge of the ALTC device 201. The film or sheet can be thermally fused. The film or sheet can be laminated together. Other manufacturing methods are contemplated.

Various other modifications, adaptations, and alternative designs are of course possible in light of the above teachings. Therefore, it should be understood at this time that the inventions may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described. Any methods disclosed herein need not be performed in the order recited. The methods disclosed herein include certain actions taken by a practitioner; however, they can also include any third-party instruction of those actions, either expressly or by implication. For example, actions such as "inserting a catheter transfemorally" includes "instructing the insertion of a catheter transfemorally." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A clot capture system, comprising:
   an outer sheath comprising a central lumen;
   a dual lumen shaft configured to be positioned within the central lumen of the outer sheath;
   an inner pusher configured to be positioned within a first lumen of the dual lumen shaft;
   an anchor pusher configured to be positioned within a second lumen of the dual lumen shaft;
   an anchor coupled to the anchor pusher;
   a shape memory tubular body comprising a first end, a second end, and an axial length therebetween, the first end having an opening and a capture guide attached to a portion of the opening,
   wherein the shape memory tubular body and the anchor are compressed in a first configuration,
   wherein the shape memory tubular body is transformable to a second configuration in which the first end and the capture guide are radially expanded but the second end and a majority of the shape memory tubular body remains compressed within the first lumen of the dual lumen shaft and the shape memory tubular body has a first expanded axial length with a first cross-section, wherein the first cross-section is substantially similar to a cross-section of the capture guide,
   wherein the shape memory tubular body is transformable to a third configuration in which the shape memory tubular body has a second expanded axial length greater than the first expanded axial length, wherein the shape memory tubular body encapsulates the anchor in the third configuration.

2. The clot capture system of claim 1, comprising two anchors.

3. The clot capture system of claim 2, wherein the two anchors have a central longitudinal axis that is coaxial.

4. The clot capture system of claim 1, comprising three anchors.

5. The clot capture system of claim 1, wherein the cross-section of the shape memory tubular body is round.

6. The clot capture system of claim 1, wherein the anchor comprises nitinol.

7. The clot capture system of claim 1, wherein the anchor forms an angle with the anchor pusher when expanded, wherein the angle is approximately 90 degrees.

8. The clot capture system of claim 1, wherein the anchor forms an angle with the anchor pusher when expanded, wherein the angle is approximately 45 degrees.

9. The clot capture system of claim 1, wherein the anchor forms an angle with the anchor pusher when expanded, wherein the angle is between 5 degrees and 135 degrees.

10. The clot capture system of claim 1, wherein a diameter of the anchor is less than a diameter of the shape memory tubular body when expanded.

11. The clot capture system of claim 1, wherein a portion of the anchor pusher is crescent shaped.

12. The clot capture system of claim 1, wherein the capture guide comprises nitinol.

13. The clot capture system of claim 1, wherein the capture guide comprises a central longitudinal axis and wherein the dual lumen shaft is offset from the central longitudinal axis.

14. The clot capture system of claim 1, wherein the second end of the shape memory tubular body is coupled to the inner pusher.

15. A method of using a clot capture system, comprising:
    positioning the system of claim 1 near a blood clot;
    transforming the shape memory tubular body to the second configuration;
    expanding the anchor; and
    transforming the shape memory tubular body to the third configuration to encapsulate the anchor.

16. The method of claim 15, wherein expanding the anchor comprises securing the anchor within the blood clot.

17. The method of claim 15, wherein transforming the shape memory tubular body to the third configuration to encapsulate the anchor further comprises encapsulating the blood clot.

18. The method of claim 15, wherein the blood clot is a neurological blood clot.

19. A clot capture system, comprising:
    an inner pusher element;
    a shape memory tubular body comprising a first end, a second end, and an axial length therebetween, the first end having an opening and a capture guide attached to at least a portion of the opening, the second end coupled to the inner pusher element,
    wherein the shape memory tubular body and the capture guide are compressed in a first configuration,
    wherein the shape memory tubular body is transformable to a second configuration in which the first end and the capture guide are radially expanded but the second end and a majority of the shape memory tubular body remains compressed and the shape memory tubular body has a first expanded axial length with a first cross-section, wherein the first cross-section is substantially similar to a cross-section of the capture guide,
    wherein the shape memory tubular body is transformable to a third configuration in which the shape memory tubular body has a second expanded axial length greater than the first expanded axial length.

20. The clot capture system of claim 19, wherein the capture guide forms a continuous loop.

21. The clot capture system of claim 19, wherein the capture guide forms a non-continuous loop.

22. A method of using a clot capture system, comprising:
    positioning the system of claim 19 near a blood clot in the first configuration;
    transforming the shape memory tubular body to the second configuration; and
    transforming the shape memory tubular body to the third configuration to encapsulate the blood clot.

23. The method of claim 22, wherein the blood clot is within the central nervous system.

24. A clot capture system, comprising:
a first tubular member comprising a central lumen;
a second tubular member;
a plurality of axially spaced-apart anchors extending radially outwardly from the first tubular member or the second tubular member; and
a shape memory tubular body comprising a first end, a second end, and an axial length therebetween, the first end having an end opening, the second end attached to the second tubular member,
wherein at least part of the shape memory tubular body is compressed within the central lumen of the first tubular member in a first delivery configuration,
wherein the shape memory tubular body is transformable to a second configuration in which the first end is radially expanded while the second end and a majority of the shape memory tubular body remains compressed within the central lumen of the first tubular member and the second end is positioned proximal to the first end and the shape memory tubular body has a first expanded axial length,
wherein the shape memory tubular body is transformable to a third configuration via movement of the first tubular member with respect to the second tubular member in which the shape memory tubular body has a second expanded axial length greater than the first expanded axial length, wherein a width of the shape memory tubular body along the second expanded axial length is substantially the same as a width of the shape memory tubular body along the first expanded axial length.

* * * * *